(12) United States Patent
Pedersen et al.

(10) Patent No.: US 8,703,125 B2
(45) Date of Patent: Apr. 22, 2014

(54) MODULATION OF THE VPS10P-DOMAIN RECEPTOR FAMILY FOR THE TREATMENT OF MENTAL AND BEHAVIOURAL DISORDERS

(75) Inventors: Simon Glerup Pedersen, Risskov (DK); Ulrich Bølcho, Harlev (DK); Kimmo Jensen, Århus V (DK); Anders Nykjær, Risskov (DK)

(73) Assignee: H. Lundbeck A/S, Valby (DK)

( * ) Notice: Subject to any disclaimer, the term of this patent is extended or adjusted under 35 U.S.C. 154(b) by 18 days.

(21) Appl. No.: 13/140,515

(22) PCT Filed: Dec. 17, 2009

(86) PCT No.: PCT/DK2009/050341
§ 371 (c)(1),
(2), (4) Date: Nov. 17, 2011

(87) PCT Pub. No.: WO2010/069331
PCT Pub. Date: Jun. 24, 2010

(65) Prior Publication Data
US 2012/0052075 A1    Mar. 1, 2012

(30) Foreign Application Priority Data
Dec. 19, 2008  (DK) .................................. 2008 01825

(51) Int. Cl.
*A61K 39/395* (2006.01)
*C07K 16/28* (2006.01)

(52) U.S. Cl.
USPC .................. 424/130.1; 424/143.1; 530/387.1; 530/388.22

(58) Field of Classification Search
None
See application file for complete search history.

(56) References Cited

FOREIGN PATENT DOCUMENTS

WO    2004/056385 A2    7/2004
WO    2008/074329 A2    6/2008

OTHER PUBLICATIONS

Pardridge, W.M. (2007). Drug targeting to the brain. Pharmaceutical Research. 24(9):1733-1744.*
Duman R.S., 2002, Pathophysiology of depression: the concept of synaptic plasticity, Eur Psychiatry, 17(Suppl. 3):306-310.
Caljon, G. et al. (2011) "*Using Microdialysis to Analyse the Passage of Monovalent Nanobodies Through the Blood-Brain Barrier*," Br. J. Pharmacol. 165:2341-2353.
Carrano, A. et al. (2012) "*Neuroinflammation and Blood-Brain Barrier Changes in Capillary Amyloid Angiopathy*," Neurodegenerative Dis. 10:329-331.
Chacko, A.-M. et al. (2013) "*Targeted Delivery of Antibody-Based Therapeutic and Imaging Agents to CNS Tumors: Crossing the Blood-Brain Barrier Divide*," Expert Opin. Drug Deliv. (2013) 10(7):907-926.
Chen, K.S. et al. (2012) "*Monoclonal Antibody Therapy for Malignant Glioma*," In: Glioma: Immunotherapeutic Approaches, Yamanaka, R. (Ed.), Landes Bioscience and Springer Science+Business Media, pp. 121-141.
Gosselet, F. et al. (2011) "[*Role of the Blood-Brain Barrier in Alzheimer's Disease*]" Med. Sci. (Paris) 27(11):987-992 (French).
Gosselet, F. et al. (2011) "[*Role of the Blood-Brain Barrier in Alzheimer's Disease*]" Med. Sci. (Paris) 27(11):987-992 (English Abstract Only).
Jordao, J.F. et al. (2010) "*Antibodies Targeted to the Brain with Image-Guided Focused Ultrasound Reduces Amyloid-β Plaque Load in the TgCRND8 Mouse Model of Alzheimer's Disease*," PloS One 5(5):e10549; pp. 1-8.
Kinoshita, M. et al. (2006) "*Noninvasive Localized Delivery of Herceptin to the Mouse Brain by MRI-Guided Focused Ultrasound-Induced Blood-Brain Barrier Disruption*," Proc. Natl. Acad. Sci. (U.S.A.) 103:11719-11723.
Liao, P.H. et al. (2012) "*Sufficient Virus-Neutralizing Antibody in the Central Nerve System Improves the Survival of Rabid Rats*," J. Biomed. Sci. 19:61, pp. 1-10.
Muruganandam, A. et al. (2002) "*Selection of Phage-Displayed Llama Single-Domain Antibodies That Transmigrate Across Human Blood-Brain Barrier Endothelium*," FASEB J. 16:240-242.
Park, J. et al. (2012) "*The Kinetics of Blood Brain Barrier Permeability and Targeted Doxorubicin Delivery Into Brain Induced by Focused Ultrasound*," J. Controlled Release 162:134-142.
Poduslo, J. F. et al. (2001) "*Permeability of Proteins at the Blood-Brain Barrier in the Normal Adult Mouse and Double Transgenic Mouse Model of Alzheimer's Disease*," Neurobiol. Dis. 8:555-567.
Poetsch, V. et al. (2010) "*Serum-Derived Immunoglobulins Neutralize Adverse Effects of Amyloid-β Peptide on the Integrity of a Blood-Brain Barrier in vitro Model*," J. Alzheimer's Dis. 21:303-314.
Raymond, S.B. et al. (2008) "*Ultrasound Enhanced Delivery of Molecular Imaging and Therapeutic Agents in Alzheimer's Disease Mouse Models*," PLoS One 3(5) e2175; pp. 1-7.
Sharma, H.S. et al. (2012) "*The Blood-Brain Barrier in Alzheimer's Disease: Novel Therapeutic Targets and Nanodrug Delivery*," Int. Rev. Neurobiol. 102:47-90.
Skrlj, N. et al. (2013) "*Recombinant Single-Chain Antibody with the Trojan Peptide Penetratin Positioned in the Linker Region Enables Cargo Transfer Across the Blood-Brain Barrier*," Appl. Biochem. Biotechnol. 169:159-169.

(Continued)

*Primary Examiner* — Christine J Saoud
*Assistant Examiner* — Jon M Lockard
(74) *Attorney, Agent, or Firm* — Mary Catherine Di Nunzio

(57) ABSTRACT

The present invention relates to methods for modulating the activity of one or more Vps10p-domain receptors selected from the group consisting of Sortilin, SorLA, SorCS1, SorCS2 and SorCS3, in an animal and methods for preparation of a medicament for the treatment of mental and behavioral disorders. The modulation is carried out by inhibiting or promoting the binding of ligands to the Vps10p-domain receptor. In vitro and in vivo methods for screening for agents capable of modulation of said Vps10p-domain receptor activity are also provided. The invention further-more relates to methods of altering expression of said receptors in vivo.

8 Claims, 31 Drawing Sheets

(56) References Cited

OTHER PUBLICATIONS

Figure 1:
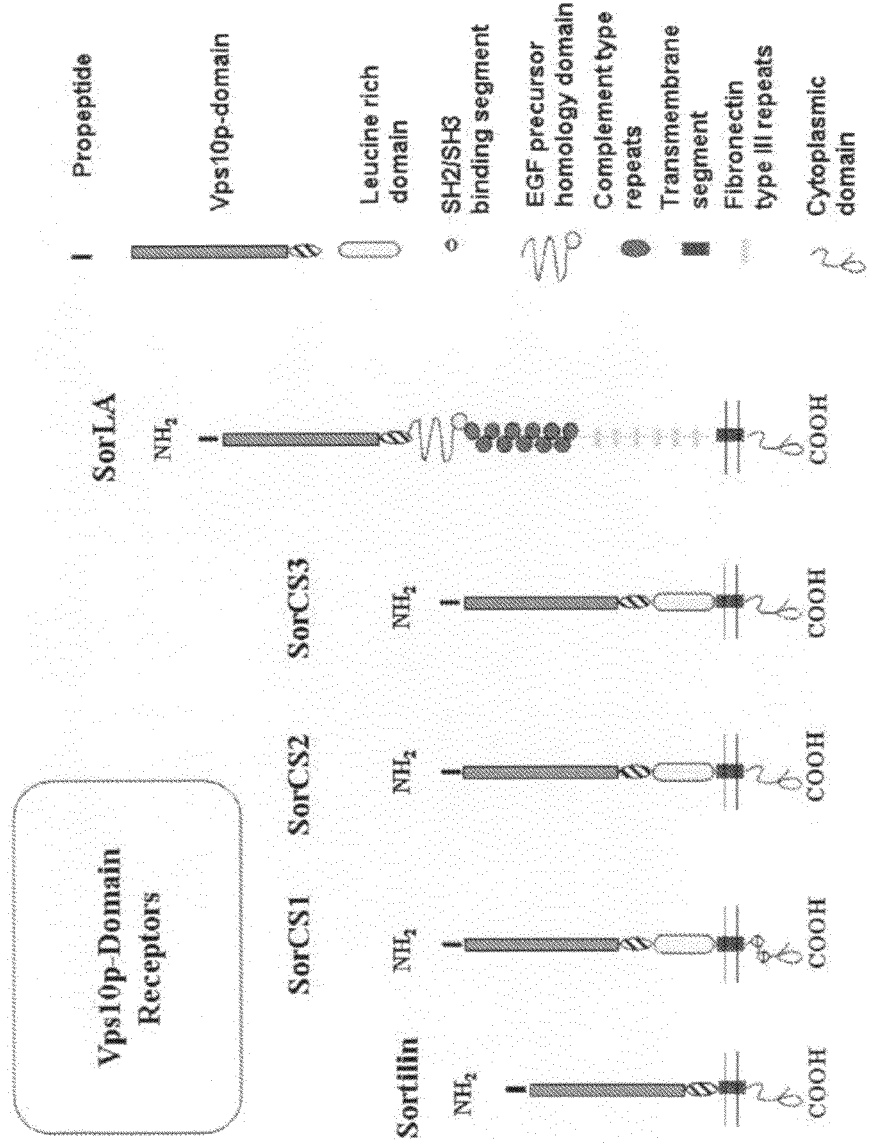

Yu, Y.J et al. (2013) "*Developing Therapeutic Antibodies for Neurodegenerative Disease*," Neurotherapeutics 10:459-472.
Watts. R.J. et al. (2013) "*Bispecific Antibodies for Delivery Into the Brain*," Curr. Opin. Chem. Biol. 17:393-399.
Guido Hermey et al., 2006, "Tumour necrosis factor α-converting enzyme mediates ectodomain shedding of Vps10p-domain receptor family members" Biochem. J., vol. 395, pp. 285-293.
English Translation of Office Action issued Jun. 5, 2013 in CN Application No. 200980157083.2 filed Dec. 17, 2009.
International Search Report and Written Opinion issued Jun. 21, 2011 in International Application No. PCT/DK2009/050341.

* cited by examiner

S2: Fraction enriched in Golgi, ER and endosomes
P2: Synaptosomal fraction
LS1: Crude synaptic vesicle fraction
LP1: Crude synaptic membrane fraction
SVP: Synaptic vesicles
SPM: Synaptic plasma membrane
PSDII: Post-synaptic density

MODULATION OF THE VPS10P-DOMAIN RECEPTOR FAMILY FOR THE TREATMENT OF MENTAL AND BEHAVIOURAL DISORDERS

CROSS-REFERENCE TO RELATED APPLICATIONS

The present application is a §371 U.S. National Stage Application of International Application No. PCT/DK2009/050341, filed Dec. 17, 2009, which claims the benefit of priority under 35 U.S.C. §119(a)-(d) of Danish Patent Application No. PA200801825, filed Dec. 19, 2008. Each of these applications is hereby incorporated by reference in its entirety.

This application contains a Sequence Listing, submitted in electronic form as filename 0719_Sequence_listing_as-_filed.txt, of size 82.4 kilobytes, created on Jun. 10, 2011. The sequence listing is hereby incorporated by reference in its entirety.

All patent and non-patent references cited in the application, or in the present application, are hereby incorporated by reference in their entirety.

FIELD OF INVENTION

The present invention relates to the modulation of the Vps10p-domain receptors for the treatment of mental and behavioural disorders. The invention further relates to identification of ligands capable of acting as modulators of signalling through the Vps10p-domain receptors. The agents are thus selected from antagonists/inhibitors and agonists depending on the specific type of mental and behavioural disorder. The present invention also relates to the preparation and use of such ligands for treating mental and behavioural disorders. The invention also relates to the use of Vps10p-domain receptor transgenic animals as animal models of mental and behavioural disorders.

BACKGROUND OF INVENTION

Mental and behavioural disorders are among the leading causes of disability, accounting for more than 37 percent of years of life lived with disability (YLD) amongst adults aged 15 years and older worldwide, and as illness likely to represent an increasingly greater health, societal and economic problem in the coming years (Lopez and Murray 1998). Mental and behavioural disorders is defined in ICD10, Chapter V, Blocks F00-F99 (Mental and behavioural disorders) from World Health Organization, and includes for example depression and major depressive disorders, obsessive compulsive disorder, schizophrenia, visual and auditory halucinations, eating disorder, anxiety disorders, and bipolar disorder (manic depressive illness). These disorders are common, severe, chronic, and often life-threatening illness. Suicide is estimated to be the cause of the death in up to 15% of the individuals with disorders such as major depressive disorders and bipolar disorder, and many other deleterious health-related effects have been recognized (Michelson, Stratakis et al. 1996; Musselman, Evans et al. 1998; Ciechanowski, Katon et al. 2000; Schulz, Beach et al. 2000; Kupfer 2005). It is increasingly being recognized that these disorders are systemic diseases with deleterious effects on multiple organ systems. For example, major depressive disorder represents a major risk factor for both the development of cardiovascular disease, as well as for death after an index myocardial infarction (Musselman, Evans et al. 1998). A recent study has suggested that the magnitude of the increased mortality risk conferred by high depressive symptoms was similar to that of stroke and congestive heart failure (Schulz, Beach et al. 2000).

Altered neuronal activity and in particular impairment in synaptic plasticity is believed to underlie the pathophysiology of mental and behavioural disorders such as but not limited to schizophrenia, depression, and bipolar disorder (Manji, Drevets et al. 2001; Lu and Martinowich 2008). It is believed that distinct neuronal activities in the mammalian central nervous system underlie the variety of specific brain functions observed in animals and humans. Subcellular mechanisms may shape the activity of individual neurons, which may again be integrated into functional cell assemblies (Buzsaki and Draguhn 2004). The function of these cell assemblies may be further integrated into functionally meaningful mechanisms, which manifest as various forms of behavior. Certain subcellular mechanisms are critical for shaping the neuronal activity, including the intrinsic excitability of single neurons, as well as basic synaptic properties, and synaptic plasticity. All these mechanisms can coincide across neuronal networks to generate the brain oscillations that are typical for mammalian brain function (Buzsaki and Draguhn 2004). In humans, if these precisely controlled brain oscillations break down, it may lead to severe mental and behavioural symptoms, which today are difficult to treat. In this context, neuronal activity covers the electrical activity in subcellular compartments, in single neurons or assemblies thereof, including the supra- or subthreshold synaptic responses and plasticity thereof, the membranal excitability in cells in neuronal tissues, the changes in intracellular ion concentrations, or transmembranal ion currents, measured by single cell imaging or single-channel, excised-patch, or whole-cell patch-clamp recordings, or by intra- or extracellular recordings, in vitro or in vivo, and behavioral correlates thereof.

Molecular mechanisms of synaptic plasticity involve initially the modification of existing synaptic proteins resulting in altered synaptic function. It also depends on second messenger neurotransmitters regulating gene transcription and changes in the levels of key proteins at the synapses. This activity-dependent mechanism takes longer and lasts longer, and is believed to be a fundamental mechanism for long-lasting memory storage and processing in the brain. Long lasting changes in the efficacy of synaptic connections between two neurons can involve the strengthening (denoted long-term potentiation or LTP) or weakening of synaptic contacts (denoted long-term depression or LTD). Traditionally, LTP has been regarded as the main mediator of spatial memory storage in the hippocampus, whereas LTD has been assigned a role in signal-to-noise regulation and in erasing memories. However, accumulating evidence suggest that LTD also has a role in learning and memory (Kemp and Manahan-Vaughan 2007). Importantly, the induction of LTD seems to be related to the development of mood disorders. For example, LTD is facilitated in animals exposed to mild naturalistic stress and in animal models of depression (Xu, Anwyl et al. 1997; Holderbach, Clark et al. 2007).

Neurotrophic factors are small soluble proteins that function as key regulators of neuronal activity including synaptic plasticity and neuronal survival through the interaction with cell surface receptor tyrosine kinases. For example, activity-dependent secretion of brain-derived neurotrophic factor (BDNF) is a key step in the induction of long-term synaptic modification (Poo 2001). In the hippocampus, BDNF is known to play an important role in the induction of early-phase LTP through its regulated release from the presynaptic side and its subsequent interaction with the receptor tyrosine kinase TrkB on the postsynaptic side (Nagappan and Lu 2005). Similarly, the release of the proform of BDNF (proBDNF) and the cleavage by extracellular proteinases into mature BDNF is required for the induction of late-phase LTP (Pang, Teng et al. 2004). On the other hand, the interaction of uncleaved proBDNF with the receptor p75$^{NTR}$ results in the induction of LTD (Woo, Teng et al. 2005). Along these lines, BDNF +/− mice and knock-in mice with defective BDNF secretion show a clear behavioral phenotype including anxiety and cognitive dysfunction (Chen, Jing et al. 2006; Einat and Manji 2006).

BDNF also modulates neuronal activity in general, for example, the activity of GABAergic neurons. GABA (gamma-amino butyric acid) is the major inhibitory neurotransmitter in the mammalian brain. GABA is released from approximately 20% of the neurons in the cerebral cortex (Somogyi, Tamas et al. 1998), and mediates fast synaptic inhibition via ubiquitously expressed GABA$_A$ receptors at synaptic contacts (Farrant and Nusser 2005). By rapidly opening Cl− channels associated with the GABA$_A$ receptor, GABA orchestrate the rhythms of the cortical networks, which is believed to underlie important functions such as sensory processing, memory formation and higher cognitive functions. As the brain rhythms break down in disorders such as epilepsy, depression, and schizophrenia, a defective GABA system is thought to play a fundamental role in the development and maintenance of these incurable mental and behavioural disorders (Lewis, Hashimoto et al. 2005). GABA$_A$ receptor-mediated inhibition can be modulated by several mechanisms, including changes in the firing rate of GABAergic interneurons, the kinetics of quantal release, alterations in synaptic cleft morphology postsynaptic modification at the GABA$_A$ receptor level (Ben-Ari and Cossart 2000), and shift in the electrochemical gradients for the permanent anions (Kaila 1994). Mature BDNF modulates GABAergic synaptic transmission via several—if not all—of these mechanisms. BDNF reduces GABA release probability at the terminals (Frerking, Malenka et al. 1998; Olofsdotter, Lindvall et al. 2000), attenuates GABA$_A$ receptor surface expression (Henneberger, Juttner et al. 2002; Hewitt and Bains 2006), and abates the driving force of Cl− electrochemical potential via inhibition of KCC2 (K—Cl cotransporter 2) (Rivera, Li et al. 2002). The modulating effect of BDNF on GABAergic transmission has also been shown in the dentate gyrus. The frequency of mIPSCs (Olofsdotter, Lindvall et al. 2000) and sIPSCs (Holm et al., submitted manuscript) are attenuated by endogenous and exogenous BDNF. Finally, mature BDNF reduces the excitability of basket cells suggesting that this mechanism participates in the reduction of sIPSCs via TrkB receptors (Holm et al., submitted manuscript).

Sortilin

Sortilin, the archetypal member of the Vps10p-domain receptor family is occasionally also referred to as neurotensin receptor 3 (NTR3), Glycoprotein 95 (Gp95) or 100 kDa NT receptor. Human Sortilin is accessed in Swiss Prot under ID No. Q99523. Sortilin, (SEQ ID NO. 1) is a type I membrane receptor expressed in a number of tissues, including the brain, spinal cord, testis, liver and skeletal muscle (Petersen, Nielsen et al. 1997; Hermans-Borgmeyer, Hermey et al. 1999). Sortilin belongs to a family of receptors comprising Sortilin, SorLA (Jacobsen, Madsen et al. 1996), SorCS1, SorCS2 and SorCS3.

All the receptors in this family share the structural feature of an approximately 600-amino acid N-terminal domain with a strong resemblance to each of the two domains, which constitute the luminal portion of the yeast sorting receptor Vps10p (Marcusson, Horazdovsky et al. 1994). The Vps10p-domain (Vps10p-D) that among other ligands binds neurotrophic factors and neuropeptides (Mazella, Zsurger et al. 1998; Munck Petersen, Nielsen et al. 1999; Nykjaer, Lee et al. 2004; Westergaard, Sorensen et al. 2004; Teng, Teng et al. 2005), constitutes the entire luminal part of Sortilin (sSortilin) and is activated for ligand binding by enzymatic propeptide cleavage (Mazella, Zsurger et al. 1998; Munck Petersen, Nielsen et al. 1999). Sortilin is a multifunctional type-1 receptor capable of endocytosis as well as intracellular sorting (Marcusson, Horazdovsky et al. 1994; Mazella, Zsurger et al. 1998; Munck Petersen, Nielsen et al. 1999), and as shown recently, it also engages in signaling by triggering proneurotrophin-induction of p75$^{NTR}$-mediated neuronal apoptosis (Nykjaer, Lee et al. 2004; Teng, Teng et al. 2005; Jansen, Giehl et al. 2007; Nakamura, Namekata et al. 2007). Sortilin is synthesized as a proprotein, which is converted to mature Sortilin by enzymatic cleavage and removal of a short N-terminal propeptide. Only the mature receptor binds ligands and interestingly, all its known ligands, e.g. Neurotensin (NT), lipoprotein lipase, the proforms of nerve growth factor-β (proNGF) and brain derived neurotrophic factor (proBDNF), receptor associated protein (RAP), and its own propeptide, compete for binding (Munck Petersen, Nielsen et al. 1999; Nielsen, Jacobsen et al. 1999; Nykjaer, Lee et al. 2004; Teng, Teng et al. 2005), indicating that the diverse ligands target a shared or partially shared binding site. NT is a tridecapeptide, which binds to Sortilin, SorLA and the two G-protein coupled receptors NTR1 and NTR2 (Tanaka, Masu et al. 1990; Cha-Ion, Vita et al. 1996; Mazella, Zsurger et al. 1998; Jacobsen, Madsen et al. 2001). The physiological role of NT in relation to Sortilin has not been fully elucidated (Vincent, Mazella et al. 1999), still NT is an important tool, as it inhibits all other ligands from binding to the Sortilin Vps10p-D. Sortilin has been the suggested to be involved in the regulation of extracellular BDNF availability, possibly by the intracellular sorting of proBDNF (Chen, Ieraci et al. 2005). In fact, Sortilin was suggested to have reduced affinity for the Val66Met variant of BDNF previously associated with poor memory function, anxiety-related behavior, and bipolar disorder (Neves-Pereira, Mundo et al. 2002; Egan, Kojima et al. 2003; Chen, Jing et al. 2006).

SorLA

Sorting protein-related receptor abbreviated SorLA (Swiss prot ID no Q92673), also known as LR11, is a 250-kDa type-1 membrane protein and the second member identified in the Vps10p-domain receptor family. SorLA, like sortilin, whose lumenal domain consists of a Vps10p domain only, is synthesized as a proreceptor that is cleaved by furin in late Golgi compartments. It has been demonstrated that the truncation conditions the Vps10p domain for propeptide inhibitable binding of neuropeptides and the receptor-associated protein. It has been demonstrated (Jacobsen, Madsen et al. 2001) that avid binding of the receptor-associated protein, apolipoprotein E, and lipoprotein lipase not inhibited by propeptide occurs to sites located in other lumenal domains. In transfected cells, about 10% of fullength SorLA is expressed on the cell surface capable mediating endocytosis. The major pool of receptors is found in late Golgi compartments, and interaction with newly synthesized ligands has been suggested. SorLA is highly expressed in distinct cell types throughout the nervous system both during development and in the adult organism (Kanaki, Bujo et al. 1998; Motoi, Aizawa et al. 1999; Offe, Dodson et al. 2006). Interestingly, SorLA levels are reduced in the sporadic form of Alzheimer's disease (Scherzer, Offe et al. 2004; Dodson, Gearing et al. 2006; Sager, Wuu et al. 2007) and inherited mutations in the SorLA gene are genetically linked to late-onset Alzheimer's disease (Rogaeva, Meng et al. 2007). Importantly, SorLA has been shown to mediate high affinity binding and sorting of amyloid precursor protein, and to confer protection against Abeta generation (Andersen, Reiche et al. 2005; Offe, Dodson et al. 2006; Spoelgen, von Arnim et al. 2006; Rogaeva, Meng et al. 2007).

SorCS1-3

SorCS1 (Swiss prot ID no Q8WY21), SorCS2 (Swiss prot ID no Q96PQ0) and SorCS3 (Swiss prot ID no Q9UPU3) constitute a subgroup of mutually highly similar proteins containing both a Vps10p-D and a leucine-rich domain bordering the transmembrane domain (Westergaard, Sorensen et al. 2004; Westergaard, Kirkegaard et al. 2005). SorCS1-3 are all prominently expressed throughout the nervous system (Hermey, Riedel et al. 1999; Hermey, Riedel et al. 2001; Hermey, Schaller et al. 2001; Rezgaoui, Hermey et al. 2001; Hermey, Keat et al. 2003) but are differentially expressed and regulated by synaptic plasticity (Hermey, Plath et al. 2004). Similar to SorLA and Sortilin, SorCS1 binds to its propeptide but no binding to either RAP or NT was observed (Hermey, Keat et al. 2003). SorCS1 and SorCS3 both binds to platelet-derived growth factor-BB while no SorCS2 ligand has been described (Hermey, Sjogaard et al. 2006). SorCS3 also binds to the prodomain of proNGF but unlike Sortilin and SorLA, it does not require propeptide cleavage in order to bind ligands (Westergaard, Kirkegaard et al. 2005). SorCS1 may play an important role outside the nervous system as a region on the gene was identified as a type 2 diabetes quantitative trait locus in mice (Clee, Yandell et al. 2006), and variations in the human SorCS1 gene are associated with diabetes-related traits (Granhall, Park et al. 2006; Goodarzi, Lehman et al. 2007). Interestingly, single nucleotide polymorphisms (SNP) in the SorCS2 gene are found to be associated with a particular high risk of developing bipolar disorder (Baum, Akula et al. 2008).

STATE OF THE ART

Although a number of drugs are already available for the treatment of mental and behavioural disorders, all have complex indirect mechanism of action, and are aimed at alleviating the symptoms rather than at treating the underlying cause of the disease. Instead, it is generally believed that drugs that target the signaling pathways that regulate synaptic plasticity should be developed as long-term treatments for mental and behavioural disorders (Manji, Drevets et al. 2001). In fact, chronic administration of antidepressants and lithium exert major effects on such signalling pathways likely by increasing the expression of neurotrophic factors, notably BDNF (Manji, Drevets et al. 2001; Duman and Monteggia 2006; Martinowich, Manji et al. 2007). Extensive experimental and clinical data suggest a central function for BDNF in mental and behavioural disorders. For example, polymorphisms in the BDNF gene correlate with mental and behavioural disorders such as schizophrenia, depression, and bipolar disorder (Neves-Pereira, Mundo et al. 2002; Schumacher, Jamra et al. 2005). In addition, BDNF serum levels are decreased in depressive and manic episodes of patients suffering from bipolar disorder but increased in schizophrenic patients (Gama, Andreazza et al. 2007). Also, BDNF levels are lower in post-mortem brain tissue from depressed patients compared to normal human subjects but higher in those who were taking antidepressants at the time of death (Chen, Dowlatshahi et al. 2001). Furthermore, direct hippocampal infusions of BDNF produce antidepressant effects in rodents (Siuciak, Lewis et al. 1997; Shirayama, Chen et al. 2002).

SUMMARY OF THE INVENTION

The present inventors have studied the effect of modulating the activity of Vps10p-domain receptors on the induction of synaptic plasticity and on the behavior of transgenic mice. The members of this family of receptors are Sortilin, SorLA, SorCS1, SorCS2 and SorCS3 (FIG. 1).

In brief, the inventors demonstrate that Vps10p-domain receptors interact directly with components of the BDNF system and function as important modulators of synaptic plasticity as well as neuronal activity, notably NMDA-receptor dependent LTD and LTP in addition to GABAergic activity. It is further shown how modulation of Vps10p-domain receptors in vivo affects animal behavior in experimental models of memory, and anxiety-related and depressive behavior. Earlier work on the Vps10p-domain receptors and their interaction with components of the BDNF system has focused on the effect on cell death.

Figure 2:
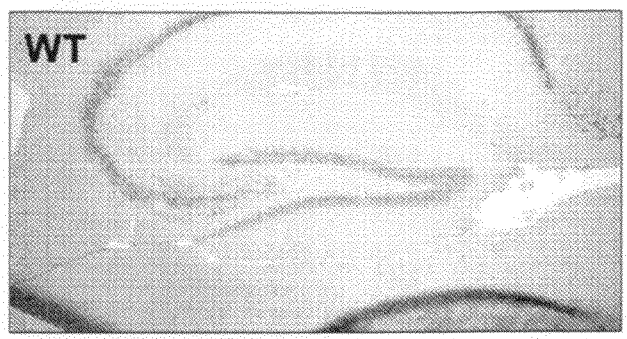
Figure 2:
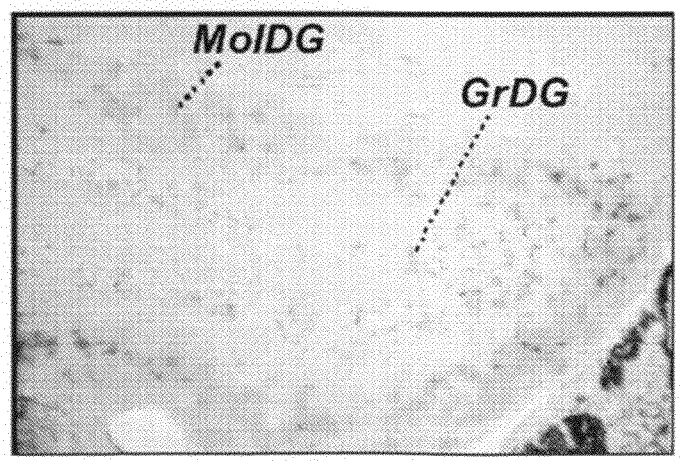
Figure 2:
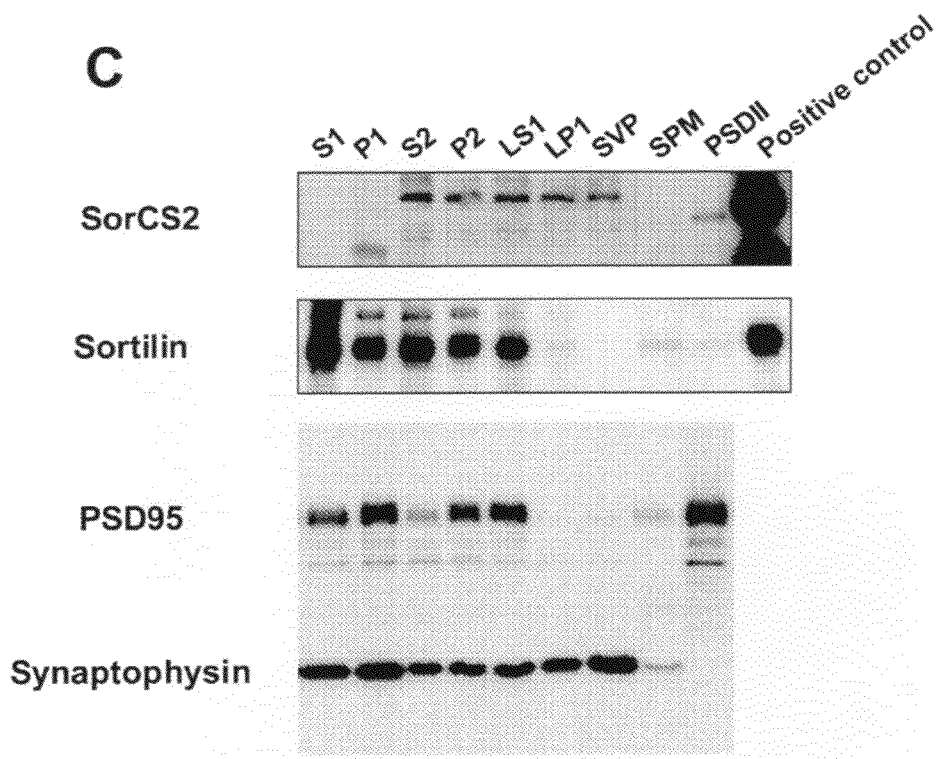
Figure 3:
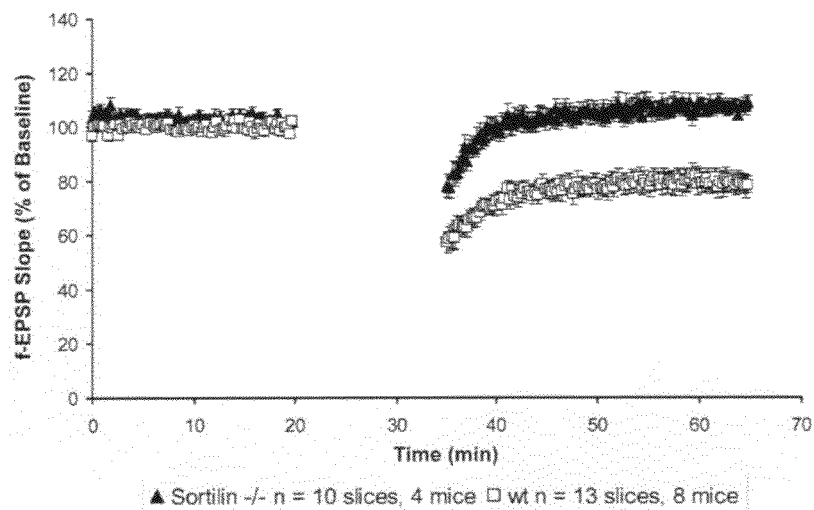
Figure 3:
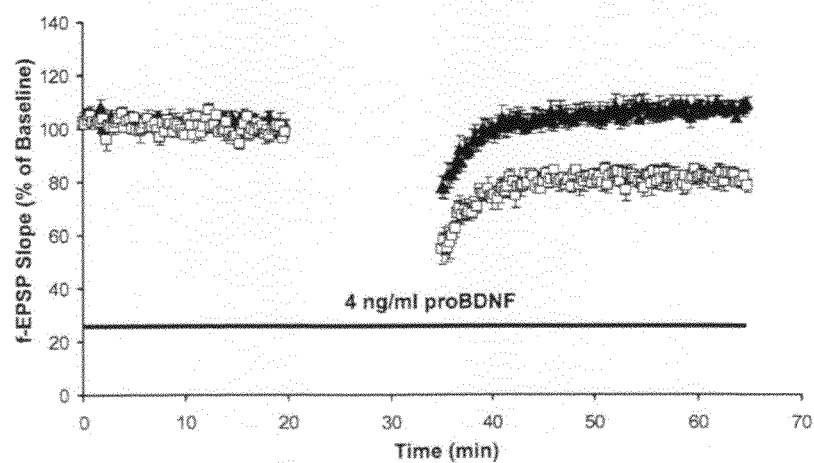
Figure 3:
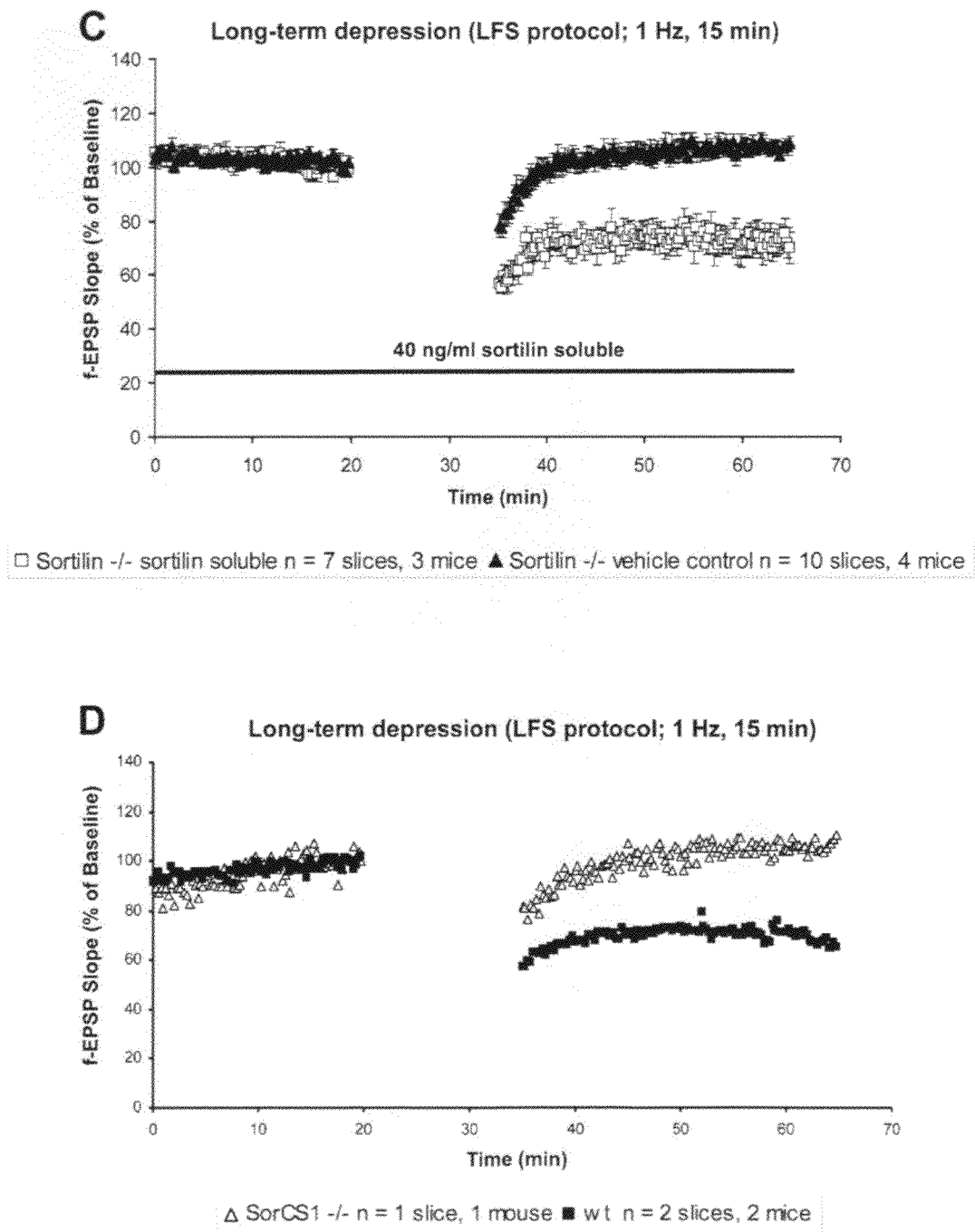
Figure 4:
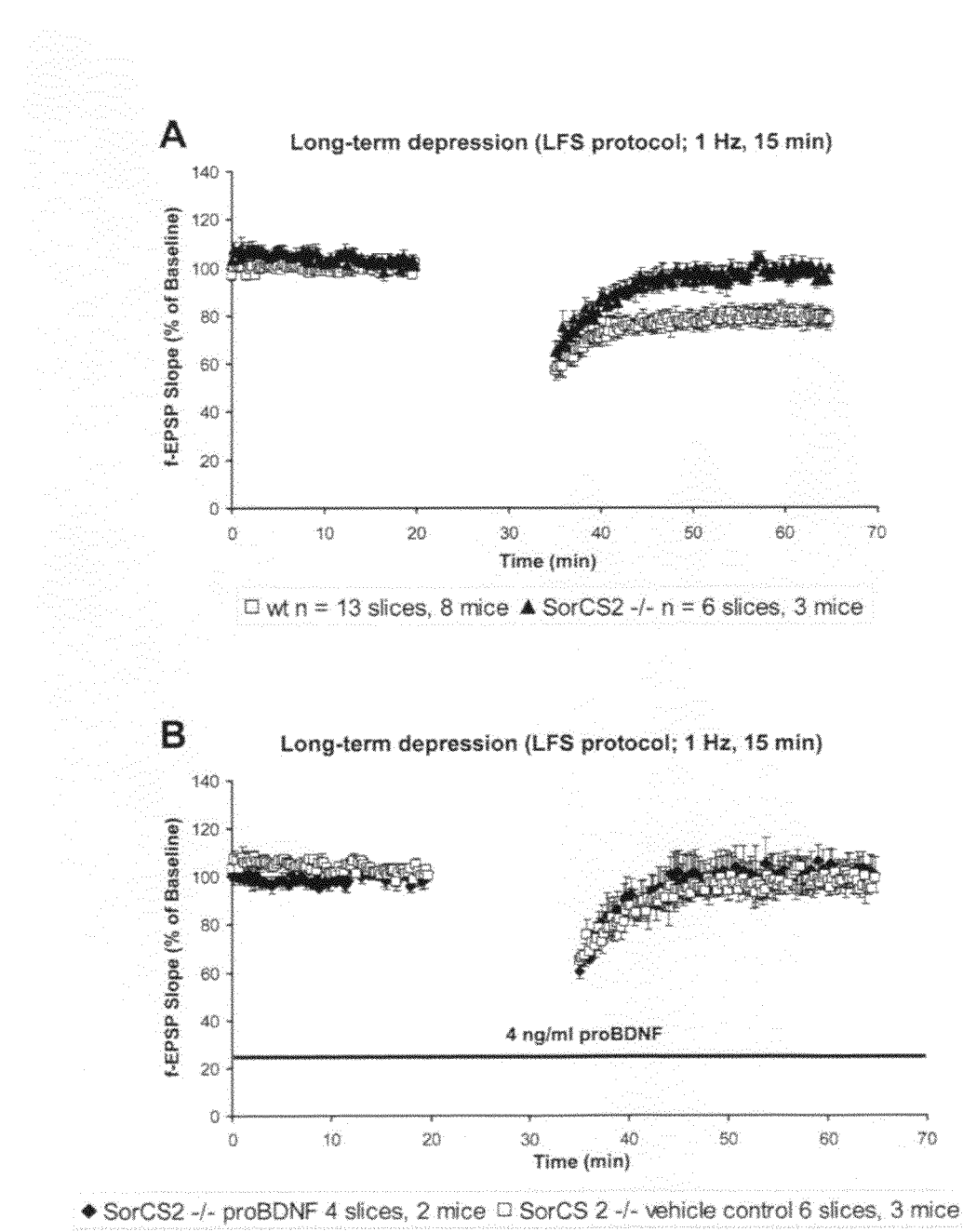
Figure 4:
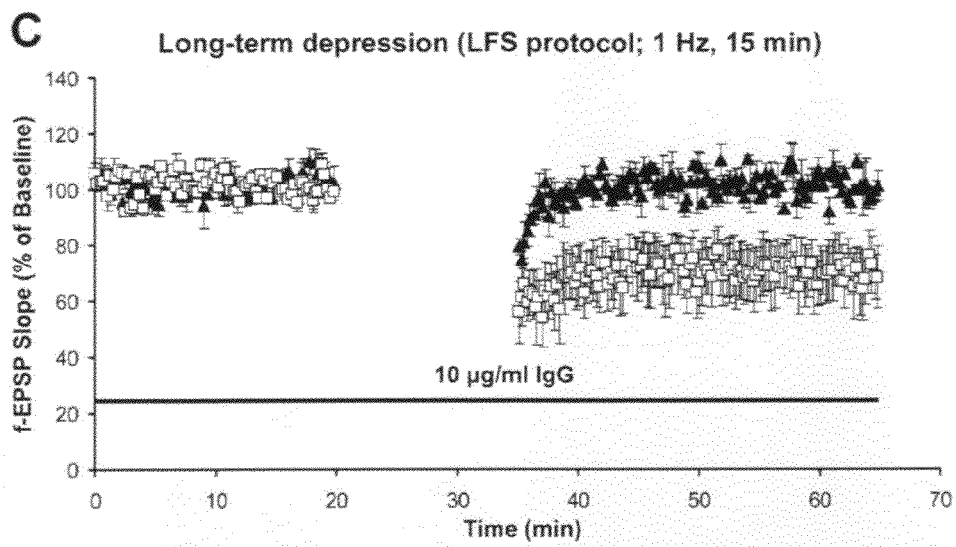
Figure 4:
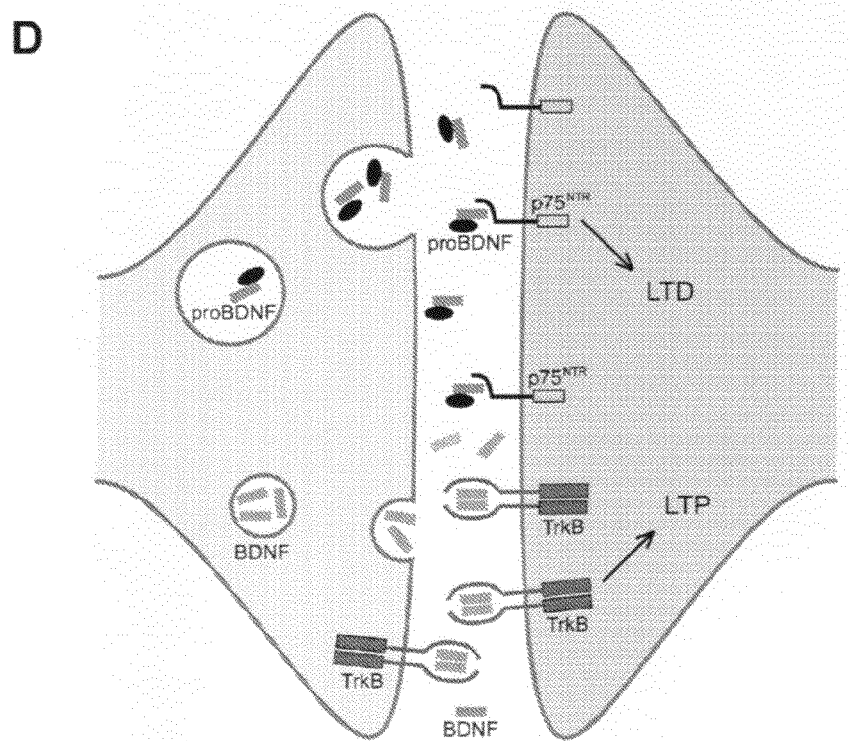
Figure 5:
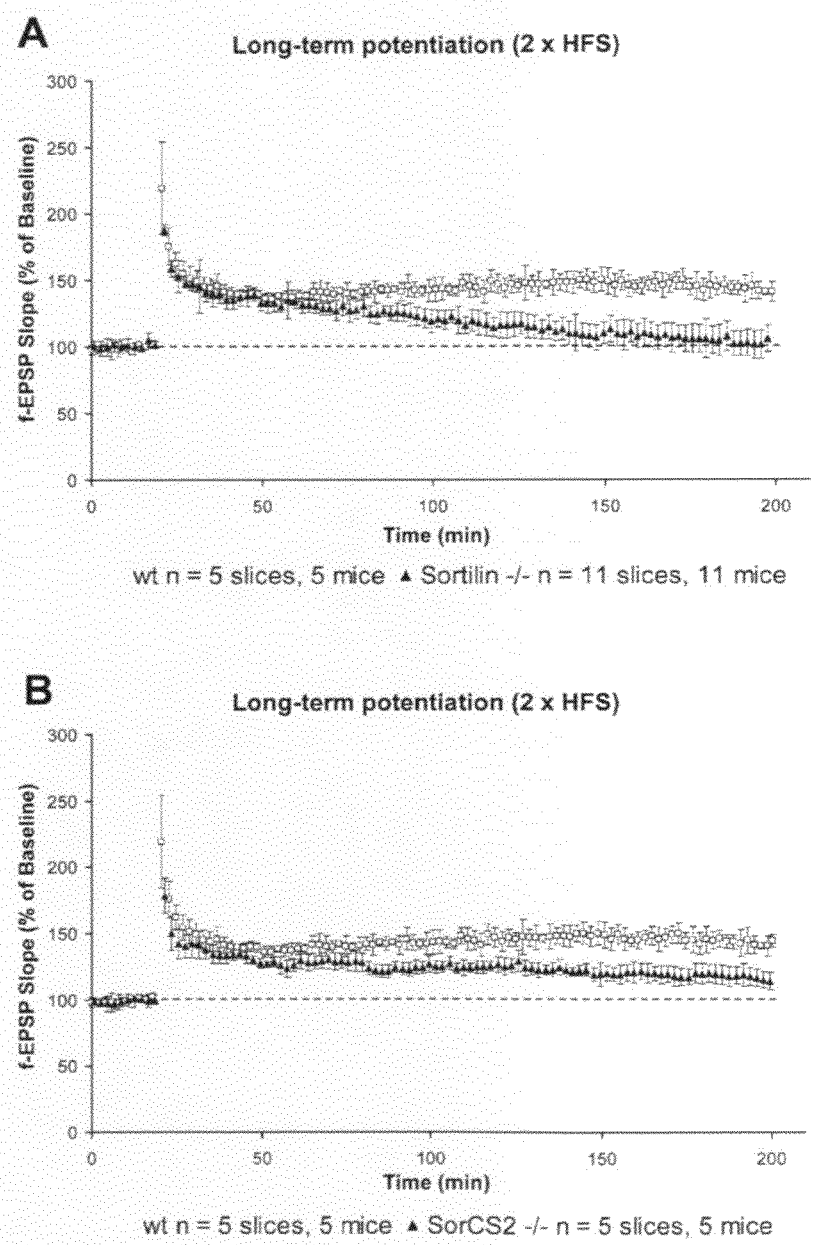
Figure 5:
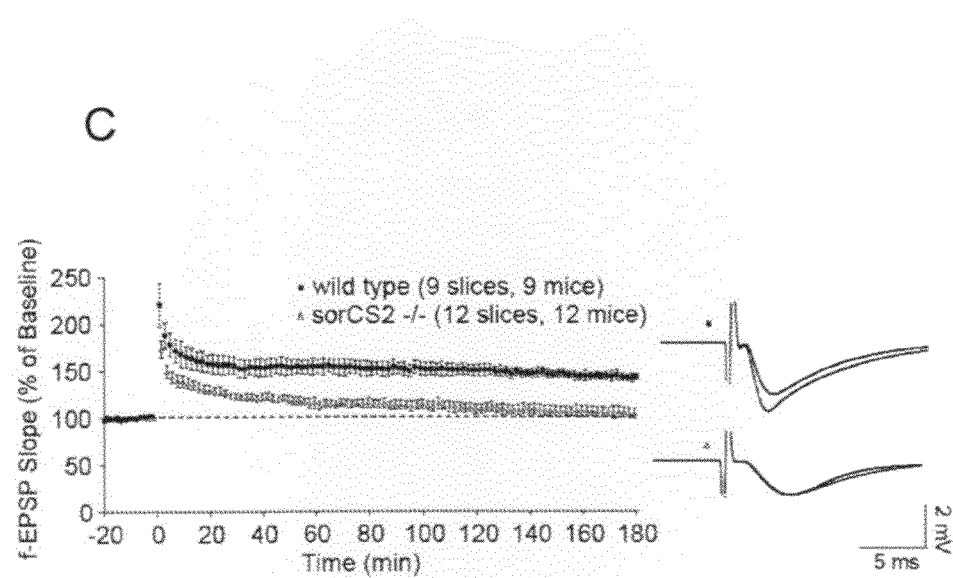
Figure 6:
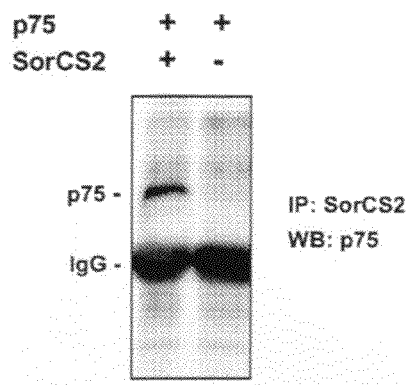
Figure 6:
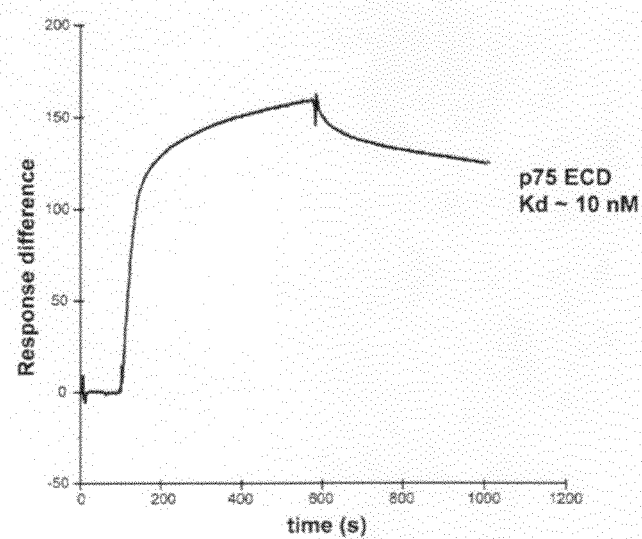
Figure 21:
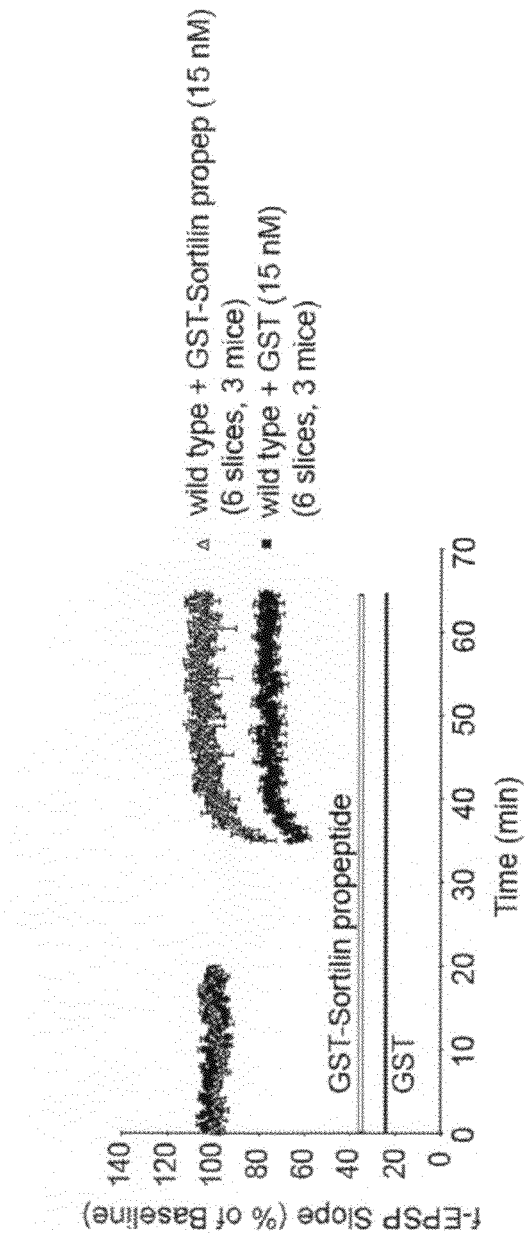

In more details, the inventors show that in the hippocampus, Sortilin is localized exclusively on the presynaptic side of the synapse whereas SorCS2 is localized in postsynaptic densities (FIG. 2). The inventors further show that NMDA receptor dependent LTD is impaired in hippocampal slices from Sortilin −/− SorCS1 −/− (FIG. 3), and SorCS2 −/− mice (FIG. 4). In addition, NMDA receptor dependent late-phase LTP is also impaired in slices from Sortilin-1 −/− and SorCS2 −/− mice (FIG. 5). Also, early-phase LTP is partially impaired in SorCS2 −/− mice (FIG. 5B). These results strongly suggest a crucial role for the Vps10p-domain receptors in synaptic plasticity. Furthermore, LTD in hippocampal slices from Sortilin-1 −/− mice but not from SorCS2 −/− mice is rescued by performing the experiment in the presence of exogenous proBDNF (FIG. 3B and FIG. 4B). Thus, it is evident that Sortilin functions on the presynaptic side to regulate proBDNF availability whereas SorCS2 functions in mediating the postsynaptic response to proBDNF and BDNF by modulating the activity of p75$^{NTR}$ and TrkB (FIG. 4D). Indeed, the inventors find that SorCS2 physically interacts with both pro- and mature BDNF (FIG. 7), and with p75$^{NTR}$ (FIG. 6). The inventors further find that the extracellular domain of TrkB interacts directly with both Sortilin, SorCS1, and SorCS2 (FIG. 8). Of particular importance, the inventors show that LTD in hippocampal slices from Sortilin-1 −/− mice can be rescued by the application of recombinant soluble Sortilin (FIG. 3C), while LTD in slices from wild type mice is inhibited by the application of recombinant Sortilin propeptide (FIG. 21). In addition, the induction of both LTD and LTP in hippocampal slices from wild-type mice is inhibited by the application of anti-SorCS2 polyclonal antibodies but not by unspecific control antibodies (FIG. 4C and FIG. 22), implying that the role of SorCS2 in synaptic plasticity is acute and depends on cell surface localized SorCS2. Taken together, these results demonstrate that pharmacological modulation of Vps10p-domain receptor activity has the potential to regulate synaptic plasticity.

The inventors find that Sortilin and SorCS2 are highly expressed in the dentate gyrus of the hippocampus (FIGS. 1A and B). Here, BDNF released from granule cells is known to decrease the excitability of GABAergic basket cells (FIG. 8A). Importantly, the inventors further find that genetic disruption of Sortilin or SorCS2 increases the excitability of GABAergic basket cells in the dentate gyrus (FIG. 8B). Again, the application of exogenous BDNF to the hippocampal slices from Sortilin −/− mice normalizes GABAergic excitability (FIG. 8B), suggesting that Vps10p-domain receptors also modulate synaptic function in this system, possibly through regulation of BDNF availability and activity.

In accordance with the role of Vps10p-domain receptors in synaptic plasticity, genetic disruption of Sortilin and SorCS2 results in altered memory function as shown by the inventors in a passive avoidance experiment (FIGS. 13A and B). It is further shown how genetic disruption of Vps10p-domain receptors affects animal behavior in two experimental models of anxiety-related and depressive/manic behavior (open field test and elevated plus maze). In these models, lack of Sortilin, SorCS1, or SorCS2 has a similar effect as would be expected from treatment with antidepressants or anxiolytic agents (FIG. 9-12, FIG. 16, FIG. 17, and FIG. 23). In accordance with previous reports (Chen, Jing et al. 2006), the inventors find that BDNF +/− mice show increased anxiety and depressive behavior in these models. This behavior is completely reversed by genetic disruption of Sortilin (FIG. 9-10), suggesting that mood disorders caused by lack of BDNF may be treated by modulation of Vps10p-domain receptor activity. Also, lack of Sortilin, SorCS2, or BDNF results in increased falls of the elevated plus maze during the experiment, a phenotype considered related to attention-deficit and hyperactivity disorder (FIG. 18). Lack of both Sortilin and BDNF, results in reduced falls of the maze (FIG. 18). In addition, the lack of Sortilin, SorCS2, or BDNF results in abnormal coping with stress as demonstrated by elevated platform exposure (FIG. 19) or a foot shock (FIG. 20) prior to performing the elevated plus maze experiment.

Figure 14:
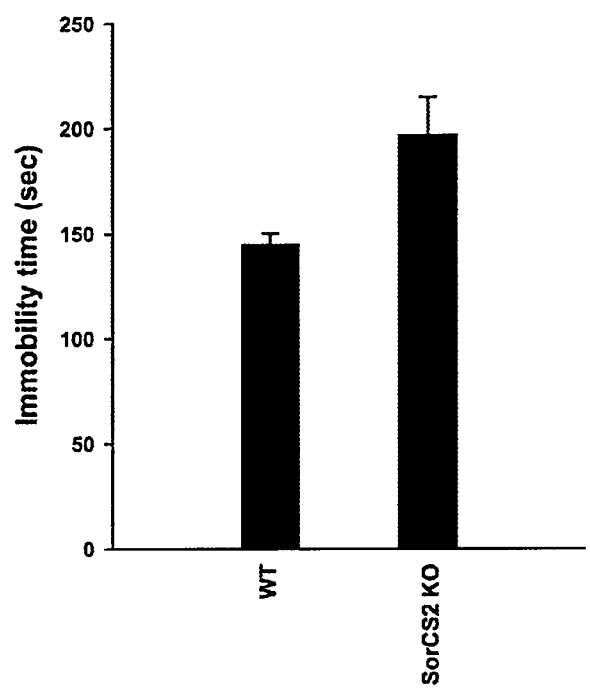

In contrast to the manic behavior of the SorCS2 −/− mice in the open field test and elevated plus maze (FIGS. 11 and 12), SorCS2 −/− mice show a clear depressive behavior in the forced swim test model of depression (FIG. 14). This is important since single nucleotide polymorphisms (SNP) in the SorCS2 gene were recently found to be associated with a particularly high risk of developing bipolar disorder (Baum, Akula et al. 2008). Research in bipolar disorder is hampered by the lack of proper animal models, and existing models only recreate the behavioral homologue of either depression or mania (Einat and Manji 2006; Coyle 2007; Roybal, Theobold et al. 2007). In the light of the behavioral data presented herein by the present inventors and the reported genetic association of the SorCS2 gene with bipolar disorder, the inventors propose that the SorCS2 −/− mouse is a unique and promising model for the disease.

In conclusion, the inventors hypothesize that modulation of Vps10p-domain receptors can be a very important target for treating mental and behavioural disorders. Depending on the disease, this may be carried out by either enhancing or inhibiting the activity of one or several Vps10p-domain receptors. For example by increasing or decreasing the expression of one or several Vps10-domain receptors, or by enhancing or inhibiting the interaction of a Vps10p-domain receptor with a specific binding partner. In the case of SorCS2, this might be $p75^{NTR}$, TrkB, the propeptide of proBDNF, and/or mature BDNF.

Thus, in one main aspect, the present invention relates to at least one agent capable of regulating neuronal activity by modulating signalling through a Vps10p-domain receptor, for use in a method of treatment of mental and behavioural disorders.

In another main aspect, the present invention relates to the use of an agent capable of regulating neuronal activity by modulating signalling through a Vps10p-domain receptor, for use in a method of treatment of mental and behavioural disorders.

In another main aspect, the present invention relates to the use of an agent capable of regulating neuronal activity by modulating signalling through a Vps10p-domain receptor, for the preparation of a medicament for treatment of mental and behavioural disorders.

In another main aspect, the present invention relates to a method of treatment of mental and behavioural disorders, said method comprising regulating neuronal activity in a patient in need thereof, by modulating signalling through a Vps10p-domain receptor.

In a further aspect, the present invention relates to a method for identification of mental and behavioural patients that will benefit from treatment with a Vps10p-domain receptor agonist or antagonist, said method comprising acquiring a sample from said patient and analysing said sample for altered levels of neurotrophic factors and/or Vps10p-domain receptors by enzyme-linked immuno-sorbent assay (ELISA) and/or by a genetic test.

In yet another aspect, the present invention relates to a method of treatment of anxiety and depression in an individual in need thereof, said method comprising administering to said individual, a therapeutically effective amount of a Sortilin antagonist.

In a further aspect, the present invention relates to a method of restoration of neuronal hyperactivity, said method comprising administering exogenous BDNF to a patient in need thereof.

In another aspect, the present invention relates to a method of specifically modulating the interaction of SorCS2 and mature BDNF, said method comprising administering to said individual, a therapeutically effective amount of the agent of the invention.

In a further aspect, the present invention relates to a method for specifically inhibiting interaction of $p75^{NTR}$ and TrkB, said method comprising administering to said individual, a therapeutically effective amount of the agent of the invention.

In another main aspect, the present invention relates to a transgenic knock-out mouse in which the endogenous Vps10p-domain receptor SorCS2 genes have been disrupted to abolish expression of a functional receptor, and wherein said mouse exhibits an altered mental behaviour relatively to a non-transgenic control mouse.

In another main aspect, the present invention relates to a transgenic knock-out mouse in which the endogenous Vps10p-domain receptor SorCS1 genes have been disrupted to abolish expression of a functional receptor, and wherein said mouse exhibits an altered mental behaviour relatively to a non-transgenic control mouse.

In another main aspect, the present invention relates to a method for determining the efficacy of an agent to bind to a Vps10p-domain receptor, and regulate parameters important for neuronal activity, said method comprising the steps of:
a. providing a cell culture expressing a Vps10p-domain receptor, and
b. providing an agonist of the Vps10p-domain receptor, and
c. providing a library of potential agents, and
d. providing an assay for determination of binding to, internalisation of and signalling through, a Vps10p-domain receptor, said assay comprising
e. adding the library of potential agents to be tested c) to the cell culture a), in the presence of the agonist b), and
f. determining
   i. the amount of agent bound to the Vps10p-domain receptor, and/or
   ii. the amount of agent internalised by the Vps10p-domain receptor, and/or iii. the degree of signalling through the Vps10p-domain receptor, and
g. comparing the amount determined in step f) with an amount measured in the absence of the agents to be tested,
h. wherein the difference in the two amounts identifies an agent
 i. capable of binding to a Vps10p-domain receptor, and/or
 ii. capable of inhibiting signalling through a Vps10p-domain receptor, and/or capable of inhibiting internalisation of an agonist of said Vps10p-domain receptor.

In another main aspect, the present invention relates to a method for determining the efficacy of an agent to bind to a Vps10p-domain receptor, and regulate parameters important for neuronal activity, said method comprising the steps of:
a. providing a cell culture expressing a Vps10p-domain receptor, and
b. providing a cell culture not expressing a Vps10p-domain receptor, and
c. optionally providing a cell culture overexpressing a Vps10p-domain receptor
d. providing an agonist for the Vps10p-domain receptor, and
e. providing a library of potential agents, and
f. providing a first assay comprising a) and a second assay comprising b) and optionally a third assay comprising c), and
g. adding the library of potential agents to be tested to the three assays, and
h. determining
 i. the amount of agent bound to the Vps10p-domain receptor, and/or
 ii. the amount of agent internalised by the Vps10p-domain receptor, and/or
 iii. the degree of signalling through the Vps10p-domain receptor, and
i. comparing the amount of agent determined in step g) using a) with the amount determined in g) using b) and the amount determined in g) using c),
j. wherein the difference in the amounts identifies an agent capable of
 i. binding to a Vps10p-domain receptor, and/or
 ii. inhibiting signalling through a Vps10p-domain receptor, and/or
k. inhibiting internalisation of an agonist of said Vps10p-domain receptor.

In yet another aspect, the present invention relates to a method for determining the efficacy of an agent to bind to a Vps10p-domain receptor, and regulate neuronal activity, said method comprising the steps of:
a. providing a mammal expressing a Vps10p-domain receptor, and
b. providing a mammal not expressing a Vps10p-domain receptor, and
c. providing a mammal overexpressing a Vps10p-domain receptor, and
d. providing an agonist for the Vps10p-domain receptor, and
e. providing a library of potential agents, and
f. administering said library of agents to said mammal of a), b) and c) respectively, and
g. determining the degree of abnormal mental behaviour in each of the mammals defined in a), b) and c), one or more tests selected from the group consisting of Open field test, Elevated plus maze test, Y-maze test, T-maze test, Radial maze test, Barnes maze test, Social regnotion tests, Aggression tests, Motor learning tests, Spatial learning tests, Circadian activity tests, Morris water maze, Holeboard test, Contextual and cue-dependent fear conditioning test, Passive avoidance test, Active avoidance test, Startle reflex test, Sexual and parental behaviour tests, Learned helplessness test, Forced swim test and Light-dark exploration test, and
h. comparing the degree of abnormal mental behaviour in step g) using a) with the degree determined in g) using b) with the degree determined in g) using c),
 wherein the difference in the degree of inhibition identifies an agent capable of binding to a Vps10p-domain receptor, inhibiting signalling through a Vps10p-domain receptor.

In a further aspect, the present invention relates to an in vitro method for screening for determining the efficacy of an agent to bind to a Vps10p-domain receptor, and potentially regulate neuronal activity, said method comprising the steps of:
a. providing a Vps10p-domain receptor, and
b. providing an agonist,
c. providing a library of potential antagonists, and
d. providing an assay for measuring the binding of an agonist to a Vps10p-domain receptor, and
e. adding the library of potential antagonists to be tested to the assay, and
f. determining the amount of agonist bound to the Vps10p-domain receptor, and
g. comparing the amount determined in step f) with an amount measured in the absence of the antagonist to be tested,
h. wherein the difference in the two amounts identifies an antagonist which alters the binding of the agonist to the Vps10p-domain receptor.

In a further aspect, the present invention relates to an in vitro method for screening for an agent for use in a method of treatment of mental and behavioural disorders, said method comprising the steps of:
i. providing a Vps10p-domain receptor, and
j. providing an agonist,
k. providing a library of potential antagonists, and
l. providing an assay for measuring the binding of an agonist to a Vps10p-domain receptor, and
m. adding the library of potential antagonists to be tested to the assay, and
n. determining the amount of agonist bound to the Vps10p-domain receptor, and
o. comparing the amount determined in step f) with an amount measured in the absence of the antagonist to be tested,
p. wherein the difference in the two amounts identifies an antagonist which alters the binding of the agonist to the Vps10p-domain receptor.

OVERVIEW OF THE DRAWINGS

FIG. 1: Receptor overview
FIG. 2: Expression and subcellular localization in the hippocampus
FIG. 3: LTD in Sortilin −/− and SorCS1−/− mice
FIG. 4: LTD in SorCS2 −/− mice
FIG. 5: LTP in Sortilin and SorCS2 −/− mice
FIG. 6: Physical interaction of SorCS2 and p75$^{NTR}$
FIG. 7: Physical interaction of SorCS2 with the propeptide of BDNF and mature BDNF-BIAcore
FIG. 8: Modulation of GABAergic activity by Sortilin and SorCS2
FIG. 9: Sortilin-1 −/−, BDNF +/−, and mice Sortilin −/−/ BDNF +/—open field test—elevated plus maze FIG. 10: Sortilin-1 −/−, BDNF +/−, and mice Sortilin −/−/BDNF +/−—mice—elevated plus maze FIG. 11: SorCS2 −/− mice—open field test FIG. 12: SorCS2 −/− mice—elevated plus maze FIG. 13: Passive avoidance FIG. 14: Forced swim test FIG. 15: Binding of the extracellular domain of TrkB to immobilized Sortilin, SorCS1, and SorCS2

Figure 16:
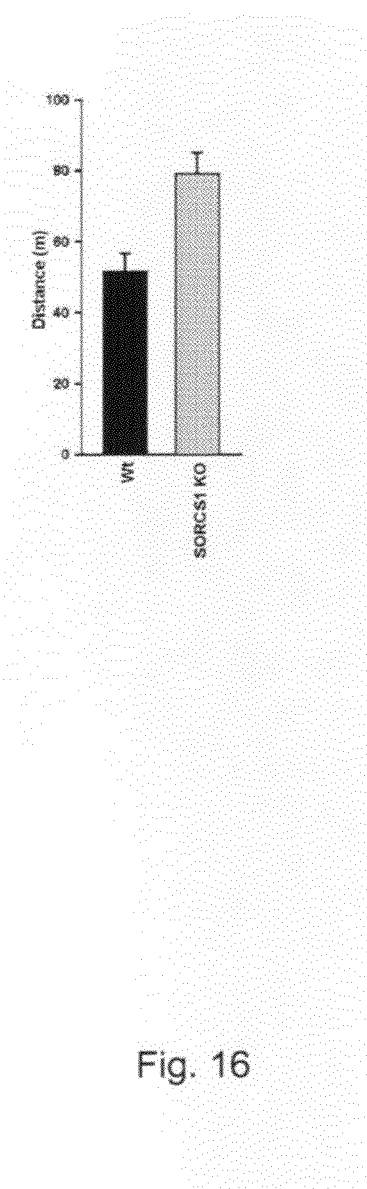

FIG. 16: SorCS2 −/− mice—open field test

Figure 17:
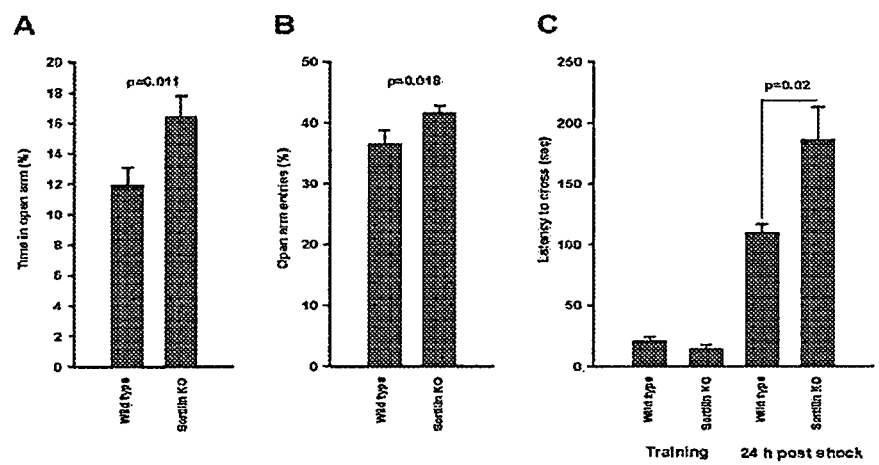
Figure 18:
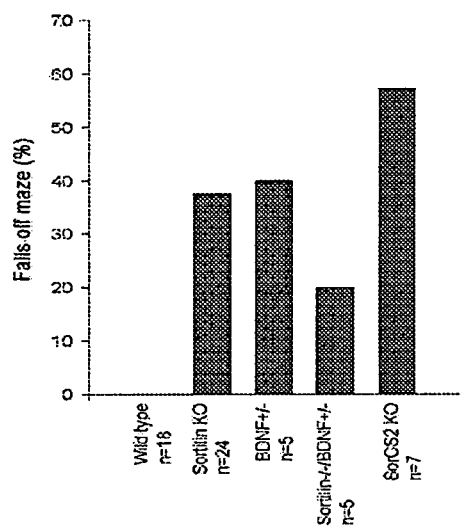

FIG. 17: Sortilin −/− mice—elevated plus maze—passive avoidance

FIG. 18: Sortilin −/−, BDNF +/−, Sortilin −/−/BDNF +/−, SorCS2 −/− mice—falls of an elevated plus maze FIG. 19: SorCS2 −/− mice—elevated plus maze FIG. 20: BDNF +/−, Sortilin −/−, SorCS2 −/− mice—elevated plus maze FIG. 21: Blockade of LTD in wild type mice by GST-Sortilin propeptide FIG. 22: Blockade of LTP in wild type mice by anti-SorCS2 IgG FIG. 23: SorCS1 −/− mice—elevated plus maze

DETAILED DESCRIPTION ON THE INVENTION

Definitions

Unless specifically indicated otherwise, all technical and scientific terms used herein have the same meaning as commonly understood by those of ordinary skill in the art to which this invention belongs. For purposes of the present invention, the following terms are defined.

Adjuvant: Any substance whose admixture with an administered immunogenic determinant/antigen increases or otherwise modifies the immune response to said determinant.

Affinity: The interaction of most ligands with their binding sites can be characterized in terms of a binding affinity. In general, high affinity ligand binding results from greater intermolecular force between the ligand and its receptor while low affinity ligand binding involves less intermolecular force between the ligand and its receptor. In general, high affinity binding involves a longer residence time for the ligand at its receptor binding site than is the case for low affinity binding. High affinity binding of ligands to receptors is often physiologically important when some of the binding energy can be used to cause a conformational change in the receptor, resulting in altered behavior of an associated ion channel or enzyme.

A ligand that can bind to a receptor, alter the function of the receptor and trigger a physiological response is called an agonist for that receptor. Agonist binding to a receptor can be characterized both in terms of how much physiological response can be triggered and the concentration of the agonist that is required to produce the physiological response. High affinity ligand binding implies that a relatively low concentration of a ligand is adequate to maximally occupy a ligand binding site and trigger a physiological response. Low affinity binding implies that a relatively high concentration of a ligand is required before the binding site is maximally occupied and the maximum physiological response to the ligand is achieved. Ligand binding is often characterized in terms of the concentration of ligand at which half of the receptor binding sites are occupied, known as the dissociation constant ($k_d$). Affinity is also the strength of binding between receptors and their ligands, for example between an antibody and its antigen.

Alcohol: A class of organic compounds containing one or more hydroxyl groups (OH). In this context a saturated or unsaturated, branched or unbranched hydrocarbon group sitting as a substituent on a larger molecule.

Alicyclic group: the term "alicyclic group" means a cyclic hydrocarbon group having properties resembling those of aliphatic groups.

Aliphatic group: in the context of the present invention, the term "aliphatic group" means a saturated or unsaturated linear or branched hydrocarbon group. This term is used to encompass alkyl, alkenyl, and alkynyl groups, for example.

Alkyl group: the term "alkyl group" means a saturated linear or branched hydrocarbon group including, for example, methyl, ethyl, isopropyl, t-butyl, heptyl, dodecyl, octadecyl, amyl, 2-ethylhexyl, and the like.

Alkenyl group: the term "alkenyl group" means an unsaturated, linear or branched hydrocarbon group with one or more carbon-carbon double bonds, such as a vinyl group.

Alkynyl group: the term "alkynyl group" means an unsaturated, linear or branched hydrocarbon group with one or more carbon-carbon triple bonds.

Amphiphil: substance containing both polar, water-soluble and nonpolar, water-insoluble groups.

Agonist: An agonist is a compound capable of increasing or effecting the activity of a receptor. Specifically, a Vps10p-domain receptor agonist is a compound capable of binding to one or more of binding sites of a Vps10p-domain receptor thereby inducing the same physiological response as a given endogenous agonist ligand compound.

Antagonist: An antagonist is in this case synonymous with an inhibitor. An antagonist is a compound capable of decreasing the activity of an effector such as a receptor.

Specifically, a Vps10p-domain receptor antagonist is a compound capable of binding to one or more of binding sites of Vps10p-domain receptor thereby inhibiting binding of another ligand thus inhibiting a physiological resonse.

antisense-RNA: an RNA molecule capable of causing gene silencing by specifically binding to an mRNA molecule of interest.

antisense-DNA: a DNA molecule capable of causing gene silencing by specifically binding to an mRNA molecule of interest.

Antibody: The term "antibody" as referred to herein includes whole antibodies and any antigen binding fragment (i.e., "antigen-binding portion") or single chain thereof.

Sortilin, SorCS1, SorCS2, TrkA, TrkB, TrkC and BDNF Polypeptides or polypeptide fragments of the invention are used to produce neublastin-specific antibodies. As used herein, a "SorCS2-specific antibody is an antibody, e.g., a polyclonal antibody or a monoclonal antibody, that is immunoreactive to a SorCS2 polypeptide or polypeptide fragment, or that binds with specificity to an epitope of a SorCS2 polypeptide.

The preparation of polyclonal and monoclonal antibodies is well known in the art. Polyclonal antibodies may in particular be obtained as described by, e.g., Green et al.: "Production of Polyclonal Antisera" in *Immunochemical Protocols* (Manson, Ed.); Humana Press, 1992, pages 1-5; by Coligan et al.: "Production of Polyclonal Antisera in Rabbits, Rats, Mice and Hamsters" in *Current Protocols in Immunology*, 1992, Section 2.4.1, and by Ed Harlow and David Lane (Eds.) in *"Antibodies: A laboratory manual"* Cold Spring Harbor Lab. Press 1988. Monoclonal antibodies may in particular be obtained as described by, e.g., Kohler & Milstein, *Nature* 1975, 256:495; Coligan et al., in *Current Protocols in Immunology*, 1992, Sections 2.5.1-2.6.7; and Harlow et al., in *Antibodies: A Laboratory Manual*; Cold Spring Harbor, Pub., 1988, page 726.

Briefly, monoclonal antibodies may be obtained by injecting, e.g., mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce the antibodies to the antigen, and isolating the antibodies from the hybridoma cultures.

Monoclonal antibodies can be isolated and purified from hybridoma cultures by a variety of well-established techniques, including affinity chromatography with protein A Sepharose, size-exclusion chromatography, and ion-exchange chromatography, see e.g. Coligan et al. in *Current Protocols in Immunology*, 1992, Sections 2.7.1-2.7.12, and Sections 2.9.1-2.9.3; and Barnes et al.: "Purification of Immunoglobulin G (IgG)" in *Methods in Molecular Biology*; Humana Press, 1992, Vol. 10, Pages 79-104. Polyclonal or monoclonal antibodies may optionally be further purified, e.g. by binding to and elution from a matrix to which the polypeptide, to which the antibodies were raised, is bound.

Antibodies which bind to the SorCS2 polypeptide of the invention can be prepared using an intact polypeptide or fragments containing small peptides of interest as the immunising antigen. The polypeptide used to immunise an animal may be obtained by recombinant DNA techniques or by chemical synthesis, and may optionally be conjugated to a carrier protein. Commonly used carrier proteins which are chemically coupled to the peptide include keyhole limpet hemocyanin (KLH), thyroglobulin, bovine serum albumin (BSA), and tetanus toxoid. The coupled peptide may then be used to immunise the animal, which may in particular be a mouse, a rat, a hamster or a rabbit.

The methods of producing SorCS2 antibodies can be applied by to Sortilin, SorCS1, TrkA, TrkB, TrkC and BDNF by the person skilled in the art.

Monoclonal Antibody: The phrase monoclonal antibody in its various grammatical forms refers to a population of antibody molecules that contains only one species of antibody combining site capable of immunoreacting with a particular antigen. A monoclonal antibody thus typically displays a single binding affinity for any antigen with which it immunoreacts. A monoclonal antibody may contain an antibody molecule having a plurality of antibody combining sites, each immunospecific for a different antigen, e.g., a bispecific monoclonal antibody.

Polyclonal antibody: Polyclonal antibodies are a mixture of antibody molecules recognising a specific given antigen, hence polyclonal antibodies may recognise different epitopes within said antigen.

Apoptosis: Apoptosis is a process of suicide by a cell in a multi-cellular organism. It is one of the main types of programmed cell death (PCD), and involves an orchestrated series of biochemical events leading to a characteristic cell morphology and death.

Apoptosis inhibitor: Any compound capable of decreasing the process of apoptosis.

Aromatic group: the term "aromatic group" or "aryl group" means a mono- or polycyclic aromatic hydrocarbon group.

Binding: The term "binding" or "associated with" refers to a condition of proximity between chemical entities or compounds, or portions thereof. The association may be non-covalent—wherein the juxtaposition is energetically favoured by hydrogen bonding or van der Waals or electrostatic interactions—or it may be covalent.

Binding site: The term "binding site" or "binding pocket", as used herein, refers to a region of a molecule or molecular complex that, as a result of its shape, favourably associates with another molecule, molecular complex, chemical entity or compound. As used herein, the pocket comprises at least a deep cavity and, optionally a shallow cavity.

Bioreactive agent: The term "bioactive agent" as used herein refers to any a substance which may be used in connection with an application that is therapeutic or diagnostic, such as, for example, in methods for diagnosing the presence or absence of a disease in a patient and/or methods for the treatment of a disease in a patient. "Bioactive agent" refers to substances, which are capable of exerting a biological effect in vitro and/or in vivo. The bioactive agents may be neutral, positively or negatively charged. Suitable bioactive agents include, for example, prodrugs, diagnostic agents, therapeutic agents, pharmaceutical agents, drugs, oxygen delivery agents, blood substitutes, synthetic organic molecules, polypeptides, peptides, vitamins, steroids, steroid analogues and genetic determinants, including nucleosides, nucleotides and polynucleotides.

Cationic group: A chemical group capable of functioning as a proton donor when a compound comprising the chemical group is dissolved in a solvent, preferably when dissolved in water.

Complex: As used herein the term "complex" refers to the combination of a molecule or a protein, conservative analogues or truncations thereof associated with a chemical entity.

Cyclic group: the term "cyclic group" means a closed ring hydrocarbon group that is classified as an alicyclic group, aromatic group, or heterocyclic group.

Cycloalkenyl: means a monovalent unsaturated carbocyclic radical consisting of one, two or three rings, of three to eight carbons per ring, which can optionally be substituted with one or two substituents selected from the group consisting of hydroxy, cyano, lower alkenyl, lower alkoxy, lower haloalkoxy, alkenylthio, halo, haloalkenyl, hydroxyalkenyl, nitro, alkoxycarbonenyl, amino, alkenylamino, alkenylsulfonyl, arylsulfonyl, alkenylaminosulfonyl, arylaminosulfonyl, alkylsulfonylamino, arylsulfonylamino, alkenylaminocarbonyl, arylaminocarbonyl, alkenylcarbonylamino and arylcarbonylamino.

Cycloalkyl: means a monovalent saturated carbocyclic radical consisting of one, two or three rings, of three to eight carbons per ring, which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino and arylcarbonylamino.

Dipole-dipole interaction: The term "dipole-dipole interaction" as used herein refers to the attraction which can occur among two or more polar molecules. Thus, "dipole-dipole interaction" refers to the attraction of the uncharged, partial positive end of a first polar molecule to the uncharged, partial negative end of a second polar molecule. "Dipole-dipole interaction" also refers to intermolecular hydrogen bonding.

Electrostatic interaction: The term "electrostatic interaction" as used herein refers to any interaction occurring between charged components, molecules or ions, due to attractive forces when components of opposite electric charge are attracted to each other. Examples include, but are not limited to: ionic interactions, covalent interactions, interactions between a ion and a dipole (ion and polar molecule), interactions between two dipoles (partial charges of polar molecules), hydrogen bonds and London dispersion bonds (induced dipoles of polarizable molecules). Thus, for example, "ionic interaction" or "electrostatic interaction" refers to the attraction between a first, positively charged molecule and a second, negatively charged molecule. Ionic or electrostatic interactions include, for example, the attraction between a negatively charged bioactive agent.

Form a ring: means that the atoms mentioned are connected through a bond when the ring structure is formed.

Fragments: The polypeptide fragments according to the present invention, including any functional equivalents thereof, may in one embodiment comprise less than 500 amino acid residues, such as less than 450 amino acid residues, for example less than 400 amino acid residues, such as less than 350 amino acid residues, for example less than 300 amino acid residues, for example less than 250 amino acid residues, such as less than 240 amino acid residues, for example less than 225 amino acid residues, such as less than 200 amino acid residues, for example less than 180 amino acid residues, such as less than 160 amino acid residues, for example less than 150 amino acid residues, such as less than 140 amino acid residues, for example less than 130 amino acid residues, such as less than 120 amino acid residues, for example less than 110 amino acid residues, such as less than 100 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues. Fragments of neurotensin include but is not limited to the C-terminal amino acids of neurotensin PYIL and YIL.

Functional equivalency: "Functional equivalency" as used, in the present invention is, according to one preferred embodiment, established by means of reference to the corresponding functionality of a predetermined fragment of the sequence.

Functional equivalents or variants of a Vps10p-domain receptor modulator will be understood to exhibit amino acid sequences gradually differing from the preferred predetermined proneurotrophin activity modulator sequence, as the number and scope of insertions, deletions and substitutions including conservative substitutions increase. This difference is measured as a reduction in homology between the preferred predetermined sequence and the fragment or functional equivalent.

A functional variant obtained by substitution may well exhibit some form or degree of native proneurotrophin activity modulator activity, and yet be less homologous, if residues containing functionally similar amino acid side chains are substituted. Functionally similar in this respect refers to dominant characteristics of the side chains such as hydrophobic, basic, neutral or acidic, or the presence or absence of steric bulk. Accordingly, in one embodiment of the invention, the degree of identity is not a principal measure of a fragment being a variant or functional equivalent of a preferred predetermined fragment according to the present invention.

Gene "silencing": a process leading to reduced expression of endogenous genes. Gene silencing is preferably the result of post-transcriptional reduction of gene expression.

Group: (Moiety/substitution) as is well understood in this technical area, a large degree of substitution is not only tolerated, but is often advisable. Substitution is anticipated on the materials of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, or S atoms, for example, in the chain as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like. The same definitions apply to "alkenyl group" and "alkenyl moiety"; to "alkynyl group" and "alkynyl moiety"; to "cyclic group" and "cyclic moiety; to "alicyclic group" and "alicyclic moiety"; to "aromatic group" or "aryl group" and to "aromatic moiety" or "aryl moiety"; as well as to "heterocyclic group" and "heterocyclic moiety".

Heterocyclic group: the term "heterocyclic group" means a closed ring hydrocarbon in which one or more of the atoms in the ring is an element other than carbon (e.g., nitrogen, oxygen, sulphur, etc.).

Heterocyclyl means a monovalent saturated cyclic radical, consisting of one to two rings, of three to eight atoms per ring, incorporating one or two ring heteroatoms (chosen from N, O or $S(O)_{0-2}$, and which can optionally be substituted with one or two substituents selected from the group consisting of hydroxyl, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminofarbonyl, arylaminocarbonyl, alkylcarbonylamino, or arylcarbonylamino.

Heteroaryl means a monovalent aromatic cyclic radical having one to three rings, of four to eight atoms per ring, incorporating one or two heteroatoms (chosen from nitrogen, oxygen, or sulphur) within the ring which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonlamino and arylcarbonylamino.

Homology: The homology between amino acid sequences may be calculated using well known scoring matrices such as any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90.

Fragments sharing homology with fragments of SEQ ID NO:1 to 10, respectively, are to be considered as falling within the scope of the present invention when they are preferably at least about 60 percent homologous, for example at least 65 percent homologous, for example at least 70 percent homologous, for example at least 75 percent homologous, for example at least 80 percent homologous, for example at least 85 percent homologous, for example at least 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous with said predetermined fragment sequences, respectively. According to one embodiment of the invention, the homology percentages refer to identity percentages.

A further suitably adaptable method for determining structure and function relationships of peptide fragments is described in U.S. Pat. No. 6,013,478, which is herein incorporated by reference. Also, methods of assaying the binding of an amino acid sequence to a receptor moiety are known to the skilled artisan.

In addition to conservative substitutions introduced into any position of a preferred predetermined proneurotrophin activity modulator, or a fragment thereof, it may also be desirable to introduce non-conservative substitutions in any one or more positions of such a proneurotrophin activity modulator.

A non-conservative substitution leading to the formation of a functionally equivalent fragment of proneurotrophin activity modulator would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Variants obtained by substitution of amino acids may in one preferred embodiment be made based upon the hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In addition to the variants described herein, sterically similar variants may be formulated to mimic the key portions of the variant structure and that such compounds may also be used in the same manner as the variants of the invention. This may be achieved by techniques of modelling and chemical designing known to those of skill in the art. It will be understood that all such sterically similar constructs fall within the scope of the present invention.

In a further embodiment the present invention relates to functional variants comprising substituted amino acids having hydrophilic values or hydropathic indices that are within +/−4.9, for example within +/−4.7, such as within +/−4.5, for example within +/−4.3, such as within +/−4.1, for example within +/−3.9, such as within +/−3.7, for example within +/−3.5, such as within +/−3.3, for example within +/−3.1, such as within +/−2.9, for example within +/−2.7, such as within +/−2.5, for example within +/−2.3, such as within +/−2.1, for example within +/−2.0, such as within +/−1.8, for example within +/−1.6, such as within +/−1.5, for example within +/−1.4, such as within +/−1.3 for example within +/−1.2, such as within +/−1.1, for example within +/−1.0, such as within +/−0.9, for example within +/−0.8, such as within +/−0.7, for example within +/−0.6, such as within +/−0.5, for example within +/−0.4, such as within +/−0.3, for example within +/−0.25, such as within +/−0.2 of the value of the amino acid it has substituted.

The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference).

The amino acid hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982).

The amino acid hydrophilicity values are: arginine (+3.0); lysine (+3.0); aspartate (+3.0.+−.1); glutamate (+3.0.+−.1); serine (+0.3); asparagine (+0.2); glutamine (+0.2); glycine (0); threonine (−0.4); proline (−0.5.+−.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) (U.S. Pat. No. 4,554,101).

In addition to the peptidyl compounds described herein, sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates formed with the same or other proneurotrophin activity modulator fragments and/or proneurotrophin activity modulator molecules, including dimers or unrelated chemical moieties. Such functional equivalents are prepared by linkage of functionalities to groups which are found in fragment including at any one or both of the N- and C-termini, by means known in the art.

Functional equivalents may thus comprise fragments conjugated to aliphatic or acyl esters or amides of the carboxyl terminus, alkylamines or residues containing carboxyl side chains, e.g., conjugates to alkylamines at aspartic acid residues; O-acyl derivatives of hydroxyl group-containing residues and N-acyl derivatives of the amino terminal amino acid or amino-group containing residues, e.g. conjugates with fMet-Leu-Phe or immunogenic proteins. Derivatives of the acyl groups are selected from the group of alkyl-moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups.

Covalent or aggregative functional equivalents and derivatives thereof are useful as reagents in immunoassays or for affinity purification procedures. For example, a fragment of proneurotrophin activity modulator according to the present invention may be insolubilized by covalent bonding to cyanogen bromide-activated Sepharose by methods known per se or adsorbed to polyolefin surfaces, either with or without glutaraldehyde cross-linking, for use in an assay or purification of anti-neurotrophin activity modulator antibodies or cell surface receptors. Fragments may also be labelled with a detectable group, e.g., radioiodinated by the chloramine T procedure, covalently bound to rare earth chelates or conjugated to another fluorescent moiety for use in e.g. diagnostic assays.

Mutagenesis of a preferred predetermined fragment of pro-neurotrophin activity modulator can be conducted by making amino acid insertions, usually on the order of about from 1 to 10 amino acid residues, preferably from about 1 to 5 amino acid residues, or deletions of from about from 1 to 10 residues, such as from about 2 to 5 residues.

In one embodiment the ligand of binding site 1, 2 or 3 is an oligopeptide synthesised by automated synthesis. Any of the commercially available solid-phase techniques may be employed, such as the Merrifield solid phase synthesis method, in which amino acids are sequentially added to a growing amino acid chain (see Merrifield, J. Am. Chem. Soc. 85:2149-2146, 1963).

Equipment for automated synthesis of polypeptides is commercially available from suppliers such as Applied Biosystems, Inc. of Foster City, Calif., and may generally be operated according to the manufacturer's instructions. Solid phase synthesis will enable the incorporation of desirable amino acid substitutions into any fragment of proneurotrophin activity modulator according to the present invention. It will be understood that substitutions, deletions, insertions or any subcombination thereof may be combined to arrive at a final sequence of a functional equivalent. Insertions shall be understood to include amino-terminal and/or carboxyl-terminal fusions, e.g. with a hydrophobic or immunogenic protein or a carrier such as any polypeptide or scaffold structure capable as serving as a carrier.

Oligomers including dimers including homodimers and heterodimers of fragments of sortilin inhibitors according to the invention are also provided and fall under the scope of the invention. Proneurotrophin activity modulator functional equivalents and variants can be produced as homodimers or heterodimers with other amino acid sequences or with native sortilin inhibitor sequences. Heterodimers include dimers containing immunoreactive sortilin inhibiting fragments as well as sortilin inhibiting fragments that need not have or exert any biological activity.

Vps10p-domain receptor antagonists including but not limited to Sortilin inhibiting peptide fragments may be synthesised both in vitro and in vivo. Method for in vitro synthesis are well known, and methods being suitable or suitably adaptable to the synthesis in vivo of sortilin inhibitors are also described in the prior art. When synthesized in vivo, a host cell is transformed with vectors containing DNA encoding a sortilin peptide inhibitor or a fragment thereof. A vector is defined as a replicable nucleic acid construct. Vectors are used to mediate expression of proneurotrophin activity modulator. An expression vector is a replicable DNA construct in which a nucleic acid sequence encoding the predetermined sortilin inhibitting fragment, or any functional equivalent thereof that can be expressed in vivo, is operably linked to suitable control sequences capable of effecting the expression of the fragment or equivalent in a suitable host. Such control sequences are well known in the art. Both prokaryotic and eukaryotic cells may be used for synthesising ligands.

Cultures of cells derived from multicellular organisms however represent preferred host cells. In principle, any higher eukaryotic cell culture is workable, whether from vertebrate or invertebrate culture. Examples of useful host cell lines are VERO and HeLa cells, Chinese hamster ovary (CHO) cell lines, and WI38, BHK, COS-7, 293 and MDCK cell lines. Preferred host cells are eukaryotic cells known to synthesize endogenous sortilin inhibitors. Cultures of such host cells may be isolated and used as a source of the fragment, or used in therapeutic methods of treatment, including therapeutic methods aimed at promoting or inhibiting a growth state, or diagnostic methods carried out on the human or animal body.

Hydrophobic bond: The term "hydrogen bond" as used herein refers to an attractive force, or bridge, which may occur between a hydrogen atom which is bonded covalently to an electronegative atom, for example, oxygen, sulphur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding).

Hydrophobic interaction: The term "hydrophobic interaction" as used herein refers to any interaction occurring between essentially non-polar (hydrophobic) components located within attraction range of one another in a polar environment (e.g. water). As used herein, attraction range is on the scale of from 0.1 up to 2 nm. A particular type of hydrophobic interaction is exerted by "Van der Waal's forces", i.e. the attractive forces between non-polar molecules that are accounted for by quantum mechanics. Van der Waal's forces are generally associated with momentary dipole moments which are induced by neighbouring molecules and which involve changes in electron distribution.

Inhibiting: Inhibiting as used herein means a manner of preventing interaction between two interaction partners, such as a receptor and a ligand, or two or more macromolecules.

In vitro/in vivo: the terms are used in their normal meaning.

Lesions: are caused by any process that damages tissues. A cancerous tumor is an example of a lesion, however the surrounding tissue damaged by a tumor is also a lesion. Trauma, including electrocution and chemical burns can also cause lesions. Certain diseases present lesions, for example the skin deformities caused by chicken pox. Lesions can also be caused by metabolic processes, like an ulcer or autoimmune activity, as in the case with many forms of arthritis. Lesions are sometimes intentionally inflicted during neurosurgery, such as the carefully-placed brain lesion used to treat epilepsy and other brain disorders.

Ligand: a substance, compound or biomolecule such as a protein including receptors, that is able to bind to and form a complex with (a second) biomolecule to serve a biological purpose. In a narrower sense, it is a signal triggering molecule binding to a site on a target protein, by intermolecular forces such as ionic bonds, hydrogen bonds and Van der Waals forces. The docking (association) is usually reversible (dissociation). Actual irreversible covalent binding between a ligand and its target molecule is rare in biological systems. As opposed to the meaning in metalorganic and inorganic chemistry, it is irrelevant, whether or not the ligand actually binds at a metal site, as it is the case in hemoglobin. Ligand binding to receptors may alter the chemical conformation, i.e. the three dimensional shape of the receptor protein. The conformational state of a receptor protein determines the functional state of a receptor. The tendency or strength of binding is called affinity. Ligands include substrates, inhibitors, activators, non-self receptors, co-receptors and neurotransmitters.

Radioligands are radioisotope labeled compounds and used in vivo as tracers in PET studies and for in vitro binding studies.

Mental and behavioural disorders: The present invention relates to a method of regulating neuronal activity for the preparation of a medicament for the treatment and/or prevention of Mental and behavioural disorders. Mental and behavioural disorders are defined according to WHO standards as outlined on http://www.who.int/classifications/apps/icd/icd10online/ at the date of filing of the present application.

Moieties of a particular compound cover group(s) or part(s) of said particular compound.

Neuronal activity: Altered neuronal activity as used herein should be understood as altered function of subcellular compartments, or of single neurons or glia cells or assemblies thereof, including the supra- or subthreshold synaptic responses and plasticity thereof, the membranal excitability in cells in neuronal tissues, changes in intracellular ion concentrations, transmembranal ion currents, or ion channels, recorded in vitro or in vivo, or analyzing behavioral correlates thereof.

Pharmaceutical agent: The terms "pharmaceutical agent" or "drug" or "medicament" refer to any therapeutic or prophylactic agent which may be used in the treatment (including the prevention, diagnosis, alleviation, or cure) of a malady, affliction, condition, disease or injury in a patient. Therapeutically useful genetic determinants, peptides, polypeptides and polynucleotides may be included within the meaning of the term pharmaceutical or drug. As defined herein, a "therapeutic agent", "pharmaceutical agent" or "drug" or "medicament" is a type of bioactive agent.

Pharmaceutical composition: or drug, medicament or agent refers to any chemical or biological material, compound, or composition capable of inducing a desired therapeutic effect when properly administered to a patient. Some drugs are sold in an inactive form that is converted in vivo into a metabolite with pharmaceutical activity. For purposes of the present invention, the terms "pharmaceutical composition" and "medicament" encompass both the inactive drug and the active metabolite.

Polypeptide: The term "polypeptide" as used herein refers to a molecule comprising at least two amino acids. The amino acids may be natural or synthetic. "Oligopeptides" are defined herein as being polypeptides of length not more than 100 amino acids. The term "polypeptide" is also intended to include proteins, i.e. functional biomolecules comprising at least one polypeptide; when comprising at least two polypeptides, these may form complexes, be covalently linked or may be non-covalently linked. The polypeptides in a protein can be glycosylated and/or lipidated and/or comprise prosthetic groups.

Polynucleotide: "Polynucleotide" as used herein refers to a molecule comprising at least two nucleic acids. The nucleic acids may be naturally occurring or modified, such as locked nucleic acids (LNA), or peptide nucleic acids (PNA). Polynucleotide as used herein generally pertains to i) a polynucleotide comprising a predetermined coding sequence, or
ii) a polynucleotide encoding a predetermined amino acid sequence, or
iii) a polynucleotide encoding a fragment of a polypeptide encoded by polynucleotides (i) or (ii), wherein said fragment has at least one predetermined activity as specified herein; and
iv) a polynucleotide the complementary strand of which hybridizes under stringent conditions with a polynucleotide as defined in any one of (i), (ii) and (iii), and encodes a polypeptide, or a fragment thereof, having at least one predetermined activity as specified herein; and
v) a polynucleotide comprising a nucleotide sequence which is degenerate to the nucleotide sequence of polynucleotides (iii) or (iv);
or the complementary strand of such a polynucleotide.

Purified antibody: The term a "purified antibody" is an antibody at least 60 weight percent of which is free from the polypeptides and naturally-occurring organic molecules with which it is naturally associated. Preferably, the preparation comprises antibody in an amount of at least 75 weight percent, more preferably at least 90 weight percent, and most preferably at least 99 weight percent.

Root mean square deviation: The term "root mean square deviation" (rmsd) is used as a mean of comparing two closely related structures and relates to a deviation in the distance between related atoms of the two structures after structurally minimizing this distance in an alignment. Related proteins with closely related structures will be characterized by relatively low RMSD values whereas larger differences will result in an increase of the RMSD value.

Sequence identity: Sequence identity is determined in one embodiment by utilising fragments of proneurotrophin activity modulator peptides comprising at least 25 contiguous amino acids and having an amino acid sequence which is at least 80%, such as 85%, for example 90%, such as 95%, for example 99% identical to the amino acid sequence of any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10 respectively, wherein the percent identity is determined with the algorithm GAP, BESTFIT, or FASTA in the Wisconsin Genetics Software Package Release 7.0, using default gap weights.

The following terms are used to describe the sequence relationships between two or more polynucleotides: "predetermined sequence", "comparison window", "sequence identity", "percentage of sequence identity", and "substantial identity".

Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

As applied to polypeptides, a degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences.

An "unrelated" or "non-homologous" sequence shares less than 40% identity, though preferably less than 25% identity, with one of the proneurotrophin activity modulator polypeptide sequences of the present invention. The term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine.

Additionally, variants are also determined based on a predetermined number of conservative amino acid substitutions as defined herein below. Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:
i) Amino acids having polar side chains (Asp, Glu, Lys, Arg, His, Asn, Gin, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gin)
ix) Amino acids having hydroxy side chains (Ser, Thr)
x) Amino acids having sulphur-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

The addition or deletion of at least one amino acid may be an addition or deletion of from preferably 2 to 250 amino acids, such as from 10 to 20 amino acids, for example from 20 to 30 amino acids, such as from 40 to 50 amino acids. However, additions or deletions of more than 50 amino acids, such as additions from 50 to 100 amino acids, addition of 100 to 150 amino acids, addition of 150-250 amino acids, are also comprised within the present invention. The deletion and/or the addition may—independently of one another—be a deletion and/or an addition within a sequence and/or at the end of a sequence.

siRNA: "small interfering RNA" (siRNA) is a short (often, but not restricted to, less than 30 nucleotides long) double-stranded RNA molecule capable of causing gene-specific silencing in mammalian cells.

Substituted lower alkyl means a lower alkyl having one to three substituents selected from the group consisting of hydroxyl, alkoxy, amino, amido, carboxyl, acyl, halogen, cyano, nitro and thiol.

Synaptic plasticity: is the ability of the connection, or synapse, between two neurons to change in strength. There are several underlying mechanisms that cooperate to achieve synaptic plasticity, including changes in the quantity of neurotransmitter released into a synapse and changes in how effectively cells respond to those neurotransmitters. Since memories are postulated to be represented by vastly interconnected networks of synapses in the brain, synaptic plasticity is one of the important neurochemical foundations of learning and memory. Two known molecular mechanisms for synaptic plasticity were revealed by research in laboratories such as that of Eric Kandel. The first mechanism involves modification of existing synaptic proteins (typically protein kinases) resulting in altered synaptic function. The second mechanism depends on second messenger neurotransmitters regulating gene transcription and changes in the levels of key proteins at synapses. This second mechanism can be triggered by protein phosphorylation but takes longer and lasts longer, providing the mechanism for long-lasting memory storage. Long-lasting changes in the efficacy of synaptic connections (long-term potentiation, or LTP) between two neurons can involve the making and breaking of synaptic contacts.

A synapse's strength also depends on the number of ion channels it has. Several facts suggest that neurons change the density of receptors on their postsynaptic membranes as a mechanism for changing their own excitability in response to stimuli. In a dynamic process that is maintained in equilibrium, NMDA and AMPA receptors are added to the membrane by exocytosis and removed by endocytosis. These processes, and by extension the number of receptors on the membrane, can be altered by synaptic activity. Experiments have shown that AMPA receptors are delivered to the membrane due to repetitive NMDAR activation.

If the strength of a synapse is only reinforced by stimulation or weakened by its lack, a positive feedback loop will develop, leading some cells never to fire and some to fire too much. But two regulatory forms of plasticity, called scaling and metaplasticity, also exist to provide negative feedback. Synaptic scaling serves to maintain the strengths of synapses relative to each other, lowering amplitudes of small excitatory postsynaptic potentials in response to continual excitation and raising them after prolonged blockage or inhibition. This effect occurs gradually over hours or days, by changing the numbers of NMDA receptors at the synapse (Pérez-Otaño and Ehlers, 2005). Metaplasticity, another form of negative feedback, reduces the effects of plasticity over time. Thus, if a cell has been affected by a lot of plasticity in the past, metaplasticity makes future plasticity less effective. Since LTP and LTD (long-term depression) rely on the influx of $Ca^{2+}$ through NMDA channels, metaplasticity may be due to changes in NMDA receptors, for example changes in their subunits to allow the concentration of $Ca^{2+}$ in the cell to be lowered more quickly.

Treatment: The term "treatment" as used herein refers to a method involving therapy including surgery of a clinical condition in an individual including a human or animal body. The therapy may be ameliorating, curative or prophylactic, i.e. reducing mental and behavioural symptoms.

Variants: The term "variants" as used herein refers to amino acid sequence variants said variants preferably having at least 60% identity, for example at least 63% identity, such as at least 66% identity, for example at least 70% sequence identity, for example at least 72% sequence identity, for example at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with any of the predetermined sequences.

Up-regulation of expression: a process leading to increased expression of genes, preferably of endogenous genes.

AGENT OF THE INVENTION

In a main aspect, the present invention relates to at least one agent capable of regulating neuronal activity by modulating signalling through a Vps10p-domain receptor, for use in a method of treatment of mental and behavioural disorders, wherein the neuronal activity is measured by:
a. Long-Term Depression, and/or
b. Early and Late-Phase Long Term Potentiation, and/or
c. GABAergic activity.

In one embodiment, the agent is a specific SorCS2 modulator agent.

In another embodiment, the agent is a specific SorCS2 antagonist.

In another embodiment, the agent is a specific SorCS2 agonist.

In another embodiment, the agent is a specific Sortilin modulator agent.

In another embodiment, the agent is a specific Sortilin antagonist.

In another embodiment, the agent is a specific Sortilin agonist.

In one embodiment, the agent is a specific SorCS1 modulator agent.

In another embodiment, the agent is a specific SorCS1 antagonist.

In another embodiment, the agent is a specific SorCS1 agonist.

In a further embodiment, the agent inhibits interaction between the extracellular domain of Sortilin and the extracellular domain of a Tyrosine Kinase receptor selected from the group consisting of TrkA, TrkB and TrkC.

In another embodiment, the agent is selected from the group consisting of organic molecules, antibodies, proteins, peptides, polypeptides, antisense RNA, antisense-DNA and siRNA.

In one important embodiment, the agent is a peptide having an amino acid sequence selected from the group consisting of a. RIFRSSDFAKNFVQTD,
b. RIFRSSDF,
c. RIFRSSDFAKNF,
d. RSSDFAKNFVQTDLPF,
e. FAKNFVQTD,
f. RIFR,
g. FAKNF,
and
h. RGGRIFRSSDFAKNF, or a combination of two or more of a to h.

In a further embodiment, the peptide as defined herein above, is cyclic.

In another embodiment of the present invention, the agent is a polypeptide such as an exogenous neurotrophin selected from the group consisting of Brain Derived Neurotrophic Factor (BDNF), Nerve Growth Factor (NGF), Neurotrophin 3 (NT3) and Neurotrophin 4/5 (NT4/5).

In yet another embodiment, the polypeptide as defined herein above is a soluble Vps10p-domain receptor or a fragment thereof, said soluble receptor selected from the group consisting of Sortilin, SorLA, SorCS1, SorCS2 and SorCS3.

In another embodiment of the present invention, the soluble receptor as defined herein above, induces neuronal activity.

In another embodiment of the present invention, the soluble receptor as defined herein above, reduces neuronal activity.

In a further embodiment, the at least one agent of the present invention, is two agents.

In a further embodiment, the at least one agent of the present invention, is three or more agents.

In one embodiment, the agents of the present inventions agents are selected from the group consisting of a specific SorCS2 antagonist, a specific SorCS2 agonist, a specific SorCS1 antagonist, a specific SorCS1 agonist, a specific Sortilin antagonist and a specific Sortilin agonist.

In an important embodiment, the agent of the present invention is capable of modulating interaction between SorCS2 and an interaction partner selected from the group consisting of $p75^{NTR}$, TrkB, TrkB, $p75^{NTR}$:TrkB binary complex, the propeptide of proBDNF, mature BDNF, GluR, AMPA-R and the NMDA-receptor.

In another embodiment, the agent of the present invention is capable of modulating interaction between SorCS2 and a ligand selected from the group consisting of $p75^{NTR}$, TrkB, the propeptide of proBDNF, and mature BDNF.

Antibodies

In a highly preferred embodiment, the agent of the present invention is an antibody.

An antibody binds tightly to a particular target molecule, thereby either inactivating it directly or marking it for destruction. The antibody recognizes its target (antigen) with remarkable specificity and strength dictated by the sum of many chemical forces, including hydrogen bonds, hydrophobic and van der Waal's forces, as well as ionic interactions. In general, the more complex the target is chemically, the more immunogenic it will be. The antigenic determinant may encompass short linear amino acid stretches or a more complicated, three-dimensional protein module.

Conceptually, antibodies directed against a target receptor may inhibit ligand binding in two ways: competitive or allosteric. Competitive inhibition involves the direct binding of the antibody to or near the ligand binding site on the receptor, thereby displacing the ligand from its receptor or sterically inhibiting the approach of the ligand to the ligand binding site. Allosteric inhibition involves the binding of the antibody to a site on the receptor polypeptide that is distinct from the ligand binding epitope. However, binding to this site will induce a conformational change in the overall structure of the receptor that makes it more difficult or even impossible for the ligand to bind to its cognate recognition site.

It is an aspect of the present invention to provide antibodies or functional equivalents thereof specifically recognising and binding epitopes of the Vps10p-domain receptors, TrkA, TrkB, TrkC and p75$^{NTR}$ receptors.

The antibody or functional equivalent thereof may be any antibody known in the art, for example a polyclonal or a monoclonal antibody derived from a mammal or a synthetic antibody, such as a single chain antibody or hybrids comprising antibody fragments. Furthermore, the antibody may be mixtures of monoclonal antibodies or artificial polyclonal antibodies. In addition functional equivalents of antibodies may be antibody fragments, in particular epitope binding fragments. Furthermore, antibodies or functional equivalent thereof may be a small molecule mimicking? an antibody. Naturally occurring antibodies are immunoglobulin molecules consisting of heavy and light chains. In preferred embodiments of the invention, the antibody is a monoclonal antibody.

Monoclonal antibodies (Mab's) are antibodies, wherein every antibody molecule are similar and thus recognises the same epitope. Monoclonal antibodies are in general produced by a hybridoma cell line. Methods of making monoclonal antibodies and antibody-synthesizing hybridoma cells are well known to those skilled in the art. Antibody producing hybridomas may for example be prepared by fusion of an antibody producing B lymphocyte with an immortalized B-lymphocyte cell line. Monoclonal antibodies according to the present invention may for example be prepared as described in Antibodies: A Laboratory Manual, By Ed Harlow and David Lane, *Cold Spring Harbor Laboratory Press*, 1988. Said monoclonal antibodies may be derived from any suitable mammalian species, however frequently the monoclonal antibodies will be rodent antibodies for example murine or rat monoclonal antibodies. It is preferred that the antibodies according to the present invention are monoclonal antibodies or derived from monoclonal antibodies.

Polyclonal antibodies is a mixture of antibody molecules recognising a specific given antigen, hence polyclonal antibodies may recognise different epitopes within said antigen. In general polyclonal antibodies are purified from serum of a mammal, which previously has been immunized with the antigen. Polyclonal antibodies may for example be prepared by any of the methods described in Antibodies: A Laboratory Manual, By Ed Harlow and David Lane, *Cold Spring Harbor Laboratory Press*, 1988. Polyclonal antibodies may be derived from any suitable mammalian species, for example from mice, rats, rabbits, donkeys, goats, sheeps, cows or camels. The antibody is preferably not derived from a non-mammalian species, i.e. the antibody is for example preferably not a chicken antibody. The antibody may also for example be an artificial polyclonal antibody as for example described in U.S. Pat. No. 5,789,208 or U.S. Pat. No. 6,335,163, both patent specifications are hereby incorporated by reference into the application in their entirety.

The antibodies according to the present invention may also be recombinant antibodies. Recombinant antibodies are antibodies or fragments thereof or functional equivalents thereof produced using recombinant technology. For example recombinant antibodies may be produced using a synthetic library or by phage display. Recombinant antibodies may be produced according to any conventional method for example the methods outlined in "Recombinant Antibodies", Frank Breitling, Stefan Dübel, Jossey-Bass, September 1999.

The antibodies according to the present invention may also be bispecific antibodies, i.e. antibodies specifically recognising two different epitopes. Bispecific antibodies may in general be prepared starting from monoclonal antibodies, or from recombinant antibodies, for example by fusing two hybridoma's in order to combine their specificity, by Chemical crosslinking or using recombinant technologies. Antibodies according to the present invention may also be tri-specific antibodies.

Functional equivalents of antibodies may in one preferred embodiment be a fragment of an antibody, preferably an antigen binding fragment or a variable region.

Examples of antibody fragments useful with the present invention include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

Preferred antibody fragments retain some or essential all the ability of an antibody to selectively binding with its antigen or receptor. Some preferred fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule and can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

In one embodiment of the present invention the antibody is a single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "scFv" antibody fragments. Generally, the Fv polypeptide further comprises a polypeptide linker between the VH and VL domains that enables the scFv to form the desired structure for antigen binding.

In another embodiment of the present invention the functional equivalent of an antibody is a small molecule mimicking an antibody. Such molecules may be a non-immunoglobulin binding members. Thus the epitope polypeptide of the present invention binding may be derived from a naturally occurring protein or polypeptide; said protein or polypeptide may for example be designed de novo, or may be selected from a library. The binding member may be a single moiety, e.g., a polypeptide or protein domain, or it may include two or more moieties, e.g., a pair of polypeptides such as a pair polypeptides. The binding polypeptide may for example, but not exclusively, be a lipocalin, a single chain MHC molecule, an Anticalin™ (Pieris), an Affibody™, or a Trinectin™ (Phylos), Nanobodies (Ablynx). The binding member may be selected or designed by recombinant methods known by people well known in the art.

Human Antibodies

Human monoclonal antibodies of the invention can be produced by a variety of techniques, including conventional monoclonal antibody methodology, e.g., the standard somatic cell hybridization technique of Kohler and Milstein, *Nature* 256:495 (1975). Although somatic cell hybridization procedures are preferred, in principle, other techniques for producing monoclonal antibody can be employed, e.g., viral or oncogenic transformation of B-lymphocytes or phage display techniques using libraries of human antibody genes.

In one embodiment, human monoclonal antibodies are directed against an epitope comprising amino acid residues R325, S316, Y351, I353, K260, I327, F314, F350 to M363, S305, F306, T398 to G400, I303-G309, Q349-A356, Y395 and T402 of SEQ ID NO. 1.

In another embodiment, human monoclonal antibodies are directed against an epitope comprising amino acid residues R325, S316, Y351, I353, K260, I1327, F314, F350 to M363, S305, F306 and T398 to G400 of SEQ ID NO. 1.

In another embodiment, human monoclonal antibodies are directed against an epitope comprising amino acid residues R325, S316, Y351, I353, K260, I1327, F314 and F350 to M363 of SEQ ID NO. 1.

In another embodiment, human monoclonal antibodies are directed against an epitope comprising amino acid residues L572, L114, V112, R109 to S111, S115 to G118, T570, G571, W586, W597, T168-I174, L572, A573 and S584 to F588 of SEQ ID NO. 1.

In another embodiment, human monoclonal antibodies are directed against an epitope comprising amino acid residues L572, L114, V112, R109 to S111, S115 to G118, T570, G571, W586 and W597 of SEQ ID NO. 1.

In another embodiment, human monoclonal antibodies are directed against an epitope comprising amino acid residues L572, L114 and V112 of SEQ ID NO. 1.

In another embodiment, human monoclonal antibodies are directed against an epitope comprising amino acid residues D403, S420, D422, N423, S424, 1425, E426, T451, Y466, E470, I498, S499 and V500 of SEQ ID NO. 1.

In another embodiment, human monoclonal antibodies are directed against an epitope comprising amino acid residues D403, N423, S424, 1425, T451, Y466, I498 and V500 of SEQ ID NO. 1.

In another embodiment, human monoclonal antibodies are directed against an epitope comprising amino acid residues T451, Y466, I498 and V500 of SEQ ID NO. 1.

Immunizations

To generate fully human monoclonal antibodies to the epitopes of interest to the present invention, transgenic or transchromosomal mice containing human immunoglobulin genes (e.g., HCo12, HCo7 or KM mice) can be immunized with an enriched preparation of the antigen and/or cells expressing the epitopes of the receptor targets of the present invention, as described, for example, by Lonberg et al. (1994), supra; Fishwild et al. (1996), supra, and WO 98/24884. Alternatively, mice can be immunized with DNA encoding the CaOU-1 epitope. Preferably, the mice will be 6-16 weeks of age upon the first infusion.

Cumulative experience with various antigens has shown that the HuMAb transgenic mice respond best when initially immunized intraperitoneally (i.p.) or subcutaneously (s.c.) with antigen expressing cells in complete Freund's adjuvant, followed by every other week i.p. immunizations (up to a total of 10) with the antigen expressing cells in PBS. The immune response can be monitored over the course of the immunization protocol with plasma samples being obtained by retro-orbital bleeds. The plasma can be screened by FACS analysis, and mice with sufficient titers of anti-antigen human immunoglobulin can be used for fusions. Mice can be boosted intravenously with antigen expressing cells for example 4 and 3 days before sacrifice and removal of the spleen.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; and Queen, C. et al. (1989) *Proc. Natl. Acad. Sci. USA* 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody which contains mutations throughout the variable gene but typically clustered in the CDRs. For example, somatic mutations are relatively infrequent in the amino terminal portion of framework region 1 and in the carboxy-terminal portion of framework region 4. For this reason, it is not necessary to obtain the entire DNA sequence of a particular antibody in order to recreate an intact recombinant antibody having binding properties similar to those of the original antibody (see WO 99/45962). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266:19867-19870); and HindIII sites are engineered upstream of the translation initiation sites.

For both the heavy and light chain variable regions, the optimized coding and corresponding non-coding, strand sequences are broken down into 30-50 nucleotides approximately at the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the Bbsl site of the kappa light chain, or the Agel site of the gamma heavy chain) in the PCR amplification to generate fragments that can easily be cloned into the expression vector constructs.

The reconstructed heavy and light chain variable regions are then combined with cloned promoter, leader, translation initiation, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Monovalent Antibodies the monospecific binding polypeptide may be monovalent, i.e. having only one binding domain.

For a monovalent antibody, the immunoglobulin constant domain amino acid residue sequences comprise the structural portions of an antibody molecule known in the art as CH1, CH2, CH3 and CH4. Preferred are those binding polypeptides which are known in the art as $C_L$. Preferred $C_L$ polypeptides are selected from the group consisting of $C_{kappa}$ and $C_{lambda}$.

Furthermore, insofar as the constant domain can be either a heavy or light chain constant domain ($C_H$ or $C_L$, respectively), a variety of monovalent binding polypeptide compositions are contemplated by the present invention. For example, light chain constant domains are capable of disulfide bridging to either another light chain constant domain, or to a heavy chain constant domain. In contrast, a heavy chain constant domain can form two independent disulfide bridges, allowing for the possibility of bridging to both another heavy chain and to a light chain, or to form polymers of heavy chains.

Thus, in another embodiment, the invention contemplates an isolated monovalent binding polypeptide wherein the constant chain domain C has a cysteine residue capable of forming at least one disulfide bridge, and where at least two monovalent polypeptides are covalently linked by said disulfide bridge.

In preferred embodiments, the constant chain domain C can be either $C_L$ or $C_H$. Where C is $C_L$, the $C_L$ polypeptide is preferably selected from the group consisting of $C_{kappa}$ and $C_{lambda}$.

In another embodiment, the invention contemplates a binding polypeptide composition comprising a monovalent polypeptide as above except where C is $C_L$ having a cysteine residue capable of forming a disulfide bridge, such that the composition contains two monovalent polypeptides covalently linked by said disulfide bridge.

Multispecificity, Including Bispecificity

In a preferred embodiment the present invention relates to multispecific binding polypeptides, which have affinity for and are capable of binding at least two different entities. Multispecific binding polypeptides can include bispecific binding polypeptides.

In one embodiment the multispecific molecule is a bispecific antibody (BsAb), which carries at least two different binding domains, where preferably at least one of which is of antibody origin.

A bispecific molecule of the invention can also be a single chain bispecific molecule, such as a single chain bispecific antibody, a single chain bispecific molecule comprising one single chain antibody and a binding domain, or a single chain bispecific molecule comprising two binding domains. Multispecific molecules can also be single chain molecules or may comprise at least two single chain molecules.

The multispecific, including bispecific, antibodies may be produced by any suitable manner known to the person skilled in the art.

The traditional approach to generate bispecific whole antibodies was to fuse two hybridoma cell lines each producing an antibody having the desired specificity. Because of the random association of immunoglobulin heavy and light chains, these hybrid hybridomas produce a mixture of up to 10 different heavy and light chain combinations, only one of which is the bispecific antibody. Therefore, these bispecific antibodies have to be purified with cumbersome procedures, which considerably decrease the yield of the desired product.

Alternative approaches include in vitro linking of two antigen specificities by chemical cross-linking of cysteine residues either in the hinge or via a genetically introduced C-terminal Cys as described above. An improvement of such in vitro assembly was achieved by using recombinant fusions of Fab's with peptides that promote formation of heterodimers. However, the yield of bispecific product in these methods is far less than 100%.

A more efficient approach to produce bivalent or bispecific antibody fragments, not involving in vitro chemical assembly steps, was described by Holliger et al. (1993). This approach takes advantage of the observation that scFv's secreted from bacteria are often present as both monomers and dimers. This observation suggested that the $V_H$ and $V_L$ of different chains could pair, thus forming dimers and larger complexes. The dimeric antibody fragments, also named "diabodies" by Hollinger et al., are in fact small bivalent antibody fragments that assembled in vivo. By linking the $V_H$ and $V_L$ of two different antibodies 1 and 2, to form "cross-over" chains $V_H 1 V_L 2$ and $V_H 2$-$V_L 1$, the dimerisation process was shown to reassemble both antigen-binding sites. The affinity of the two binding sites was shown to be equal to the starting scFv's, or even to be 10-fold increased when the polypeptide linker covalently linking $V_H$ and $V_L$ was removed, thus generating two proteins each consisting of a $V_H$ directly and covalently linked to a $V_L$ not pairing with the $V_H$. This strategy of producing bispecific antibody fragments was also described in several patent applications. Patent application WO 94/09131 (SCOTGEN LTD; priority date Oct. 15, 1992) relates to a bispecific binding protein in which the binding domains are derived from both a $V_H$ and a $V_L$ region either present at two chains or linked in an scFv, whereas other fused antibody domains, e.g. C-terminal constant domains, are used to stabilise the dimeric constructs. Patent application WO 94/13804 (CAM-BRIDGE ANTIBODY TECHNOLOGY/MEDICAL RESEARCH COUNCIL; first priority date Dec. 4, 1992) relates to a polypeptide containing a $V_H$ and a $V_1$ which are incapable of associating with each other, whereby the V-domains can be connected with or without a linker.

Mallender and Voss, 1994 (also described in patent application WO 94/13806; DOW CHEMICAL CO; priority date Dec. 11, 1992) reported the in vivo production of a single-chain bispecific antibody fragment in *E. coli*. The bispecificity of the bivalent protein was based on two previously produced monovalent scFv molecules possessing distinct specificities, being linked together at the genetic level by a flexible polypeptide linker. Traditionally, whenever single-chain antibody fragments are referred to, a single molecule consisting of one heavy chain linked to one (corresponding) light chain in the presence or absence of a polypeptide linker is implicated. When making bivalent or bispecific antibody fragments through the "diabody" approach (Holliger et al., (1993) and patent application WO 94/09131) or by the "double scFv" approach (Mallender and Voss, 1994 and patent application WO 94/13806), again the $V_H$ is linked to a (the corresponding) $V_L$.

The multispecific molecules described above can be made by a number of methods. For example, all specificities can be encoded in the same vector and expressed and assembled in the same host cell. This method is particularly useful where the multispecific molecule is a mAb X mAb, mAb X Fab, Fab X F(ab')$_2$ or ligand X Fab fusion protein. Various other methods for preparing bi- or multivalent antibodies are described for example described in U.S. Pat. Nos. 5,260,203; 5,455,030; 4,881,175; 5,132,405; 5,091,513; 5,476,786; 5,013,653; 5,258,498; and 5,482,858.

By using a bispecific or multispecific binding polypeptide according to the invention the invention offers several advantages as compared to monospecific/monovalent binding polypeptides.

It may be preferred that the at least one other binding domain is capable of binding an immunoactive cell, such as a leucocyte, a macrophage, a lymphocyte, a basophilic cell, and/or an eosinophilic cell, in order to increase the effect of the binding polypeptide in a therapeutic method. This may be accomplished by establishing that the at least one other binding domain is capable of specifically binding a mammalian protein, such as a human protein, such as a protein selected from any of the cluster differentiation proteins (CD), in particular CD64 and/or CD89. A method for producing bispecific antibodies having CD64 specificity is described in U.S. Pat. No. 6,071,517 to Medarex, Inc.

The production and characterization of these preferred monoclonal antibodies are described by Fanger et al. in WO 88/00052 and in U.S. Pat. No. 4,954,617. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. In other embodiments, the anti-Fcγ receptor antibody is a humanized form of mAb 22 (H22). The production and characterization of the H22 antibody is described in Graziano, R. F. et al. (1995) *J. Immunol.* 155 (10):4996-5002 and WO 94/10332. The H22 antibody producing cell line was deposited at the American Type Culture Collection on Nov. 4, 1992 under the designation HA022CL1 and has the accession No. CRL 11177.

In still other preferred embodiments, the binding specificity for an Fc receptor is provided by an antibody that binds to a human IgA receptor, e.g., an Fcα receptor (Fcαl (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148:1764).

FcαRI, FcγRI, FcγRII and FcγRIII, especially FcγRII and FcγRIII, are preferred trigger receptors for use in the invention because they (1) are expressed primarily on immune effector cells, e.g., monocytes, PMNs, macrophages and dendritic cells; (2) are expressed at high levels (e.g., 5,000-100,000 per cell); (3) are mediators of cytotoxic activities (e.g., ADCC, phagocytosis); and (4) mediate enhanced antigen presentation of antigens, including self-antigens, targeted to them.

While human monoclonal antibodies are preferred, other antibodies which can be employed in the bispecific or multispecific molecules of the invention are murine, chimeric and humanized monoclonal antibodies. Such murine, chimeric and humanized monoclonal antibodies can be prepared by methods known in the art.

Bispecific and multispecific molecules of the present invention can be made using chemical techniques (see e.g., D. M. Kranz et al. (1981) *Proc. Natl. Acad. Sci.* USA 78:5807), "polydoma" techniques (see U.S. Pat. No. 4,474,893), or recombinant DNA techniques.

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a mAb×mAb, mAb×Fab, Fab× F(ab')$_2$ or ligand x Fab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multispecific molecules are described for example in U.S. Pat. No. 5,260, 203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a γ counter or a scintillation counter or by autoradiography.

Humanised Antibody Framework

It is not always desirable to use non-human antibodies for human therapy, since the non-human "foreign" epitopes may elicit immune response in the individual to be treated. To eliminate or minimize the problems associated with non-human antibodies, it is desirable to engineer chimeric antibody derivatives, i.e., "humanized" antibody molecules that combine the non-human Fab variable region binding determinants with a human constant region (Fc). Such antibodies are characterized by equivalent antigen specificity and affinity of the monoclonal and polyclonal antibodies described above, and are less immunogenic when administered to humans, and therefore more likely to be tolerated by the individual to be treated.

Accordingly, in one embodiment the binding polypeptide has a binding domain carried on a humanised antibody framework, also called a humanised antibody.

Humanised antibodies are in general chimeric antibodies comprising regions derived from a human antibody and regions derived from a non-human antibody, such as a rodent antibody. Humanisation (also called Reshaping or CDR-grafting) is a well-established technique for reducing the immunogenicity of monoclonal antibodies (mAbs) from xenogeneic sources (commonly rodent), increasing the homology to a human immunoglobulin, and for improving their activation of the human immune system. Thus, humanized antibodies are typically human antibodies in which some CDR residues and possibly some framework residues are substituted by residues from analogous sites in rodent antibodies.

It is further important that humanized antibodies retain high affinity for the antigen and other favourable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of certain residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is maximized, although it is the CDR residues that directly and most substantially influence antigen binding.

One method for humanising MAbs related to production of chimeric antibodies in which an antigen binding site comprising the complete variable domains of one antibody are fused to constant domains derived from a second antibody, preferably a human antibody. Methods for carrying out such chimerisation procedures are for example described in EP-A-0 120 694 (Celltech Limited), EP-A-0 125 023 (Genentech Inc.), EP-A-0 171 496 (Res. Dev. Corp. Japan), EP-A-0173494 (Stanford University) and EP-A-0 194 276 (Celltech Limited). A more complex form of humanisation of an antibody involves the re-design of the variable region domain so that the amino acids constituting the non-human antibody binding site are integrated into the framework of a human antibody variable region (Jones et al., 1986).

The humanized antibody of the present invention may be made by any method capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs using oligonucleotide site-directed mutagenesis as described in the examples below.

As an example the humanized antibody of the present invention may be made as described in the brief explanation below. The humanized antibodies of the present invention may be produced by the following process:

(a) constructing, by conventional techniques, an expression vector containing an operon with a DNA sequence encoding an antibody heavy chain in which the CDRs and such minimal portions of the variable domain framework region that are required to retain antibody binding specificity are derived from a non-human immunoglobulin, and the remaining parts of the antibody chain are derived from a human immunoglobulin, thereby producing the vector of the invention;

(b) constructing, by conventional techniques, an expression vector containing an operon with a DNA sequence encoding a complementary antibody light chain in which the CDRs and such minimal portions of the variable domain framework region that are required to retain donor antibody binding specificity are derived from a non-human immunoglobulin, and the remaining parts of the antibody chain are derived from a human immunoglobulin, thereby producing the vector of the invention;

(c) transfecting the expression vectors into a host cell by conventional techniques to produce the transfected host cell of the invention; and (d) culturing the transfected cell by conventional techniques to produce the humanised antibody of the invention.

The host cell may be cotransfected with the two vectors of the invention, the first vector containing an operon encoding a light chain derived polypeptide and the second vector containing an operon encoding a heavy chain derived polypeptide. The two vectors contain different selectable markers, but otherwise, apart from the antibody heavy and light chain coding sequences, are preferably identical, to ensure, as far as possible, equal expression of the heavy and light chain polypeptides. Alternatively, a single vector may be used, the vector including the sequences encoding both the light and the heavy chain polypeptides. The coding sequences for the light and heavy chains may comprise cDNA or genomic DNA or both.

The host cell used to express the altered antibody of the invention may be either a bacterial cell such as *E. coli*, or a eukaryotic cell. In particular a mammalian cell of a well defined type for this purpose, such as a myeloma cell or a Chinese hamster ovary cell may be used.

The general methods by which the vectors of the invention may be constructed, transfection methods required to produce the host cell of the invention and culture methods required to produce the antibody of the invention from such host cells are all conventional techniques. Likewise, once produced, the humanized antibodies of the invention may be purified according to standard procedures as described below.

Human Antibody Framework

In a more preferred embodiment the invention relates to a binding polypeptide, wherein the binding domain is carried by a human antibody framework, i.e. wherein the antibodies have a greater degree of human peptide sequences than do humanised antibodies.

Human mAb antibodies directed against human proteins can be generated using transgenic mice carrying the complete human immune system rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

Such transgenic mice are available from Abgenix, Inc., Fremont, Calif., and Medarex, Inc., Annandale, N.J. It has been described that the homozygous deletion of the antibody heavy-chain joining region (IH) gene in chimeric and germline mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA 90:2551 (1993); Jakobovits et al., Nature 362:255-258 (1993); Bruggermann et al., Year in Immunol. 7:33 (1993); and Duchosal et al. Nature 355:258 (1992). Human antibodies can also be derived from phage-display libraries (Hoogenboom et al., J. Mol. Biol. 227: 381 (1991); Marks et al., J. Mol. Biol. 222:581-597 (1991); Vaughan, et al., Nature Biotech 14:309 (1996)).

The inventors of this application have raised antibodies against several parts of the Vps10p-domain receptors. The present invention is directed to antibodies against the unifying feature of this receptor family—the Vps10p domain. The below sequence alignment of the Vps10p-domain demonstrate the conservation within this receptor family.

TABLE 1

Antibodies against Vps10p-domain receptors

| Receptor | Name | Antigen | Species | Western | IH/IC | Ref. |
|---|---|---|---|---|---|---|
| SorLA | SORLA goat | extracellular domain | goat | X | X | Schmidt et. al., J. Biol. Chem. 282: 32956-67, 2007 |
| | Hale SORLA | Cytoplasmic domain | rabbit | X | | |
| | SORLA LA | Complement type repeat | rabbit | X | | |
| | Sol SORLA | extracellular domain | rabbit | X | X | Andersen et al., PNAS 103: 13461-6, 2005 |
| | SORLA tail | Cytoplasmic domain | rabbit | X | | |
| | SORLA VPS | VPS10p domain | rabbit | X | | |
| | #606870 | Peptide seq. in Vps10p-domain | rabbit | X | | |
| | #642739 | C-terminal | rabbit | X | | |
| | #643739 | Cytoplasmic tail | rabbit | X | | |
| | 20C11 | Extracellular domain | mouse | X | X | |
| | AG4 | Extracellular domain | mouse | X | | |
| Sortilin | #5264 | Extracellular domain | rabbit | X | X | Munck Petersen et al, EMBO J. 18: 595-604, 1999 |
| | #5448 | Cytoplasmic domain | rabbit | X | X | Jansen et al, Nature Neurosci. 10: 1449-1457, 2007 |

TABLE 1-continued

| | Antibodies against Vps10p-domain receptors | | | | | |
|---|---|---|---|---|---|---|
| Receptor | Name | Antigen | Species | Western | IH/IC | Ref. |
| | #5287 | Cytoplasmic domain | rabbit | X | | |
| | CP 96 334 SR 96 204 | propeptide | Rabbit | X | | Munck Petersen et al, EMBO J. 18: 595-604, 1999 |
| | #5438 | Vps10p | rabbit | X | | |
| | Sortilin goat/Laika | Extracellular domain | goat | X | | |
| | F9 | Extracellular domain | mouse | X | X | |
| | F11 | Extracellular domain | mouse | X | X | |
| | AF2934 | Extracellular domain | goat | X | X | R&D Systems, Jansen et al, Nature Neurosci. 10: 1449-1457, 2007 |
| | AF3154 | Extracellular domain | goat | X | X | R&D Systems; Jansen et al, Nature Neurosci. 10: 1449-1457, 2007 |
| | anti-NTR3 | Extracellular domain | mouse | X | X | BD Transduction Laboratories, |
| | ANT-009 | Extracellular domain | mouse | X | X | Alomone Labs; Nykjaer et al, Nature 427: 843-848, 2004 |
| SorCS1 | AF3457 | Extracellular domain | goat | X | X | BD Transduction Laboratories |
| | SorCS1 goat | Extracellular domain | goat | X | | |
| | L-SorCS1 | Extracellular domain | rabbit | X | X | Hermey et al, J. Biol. Chem. 279: 50221-50229, 2003 |
| | Leu-SorCS1 | Leucine-rich domain | rabbit | X | X | Hermey et al, J. Biol. Chem. 279: 50221-50229, 2003 |
| | #5466 | Extracellular domain | rabbit | X | X | |
| | 1D | Extracellular domain | mouse | X | | |
| | 4H | Extracellular domain | mouse | X | | |
| | 6B | Extracellular domain | mouse | X | | |
| | 4A | Extracellular domain | mouse | X | | |
| SorCS2 | AF4237 | Extracellular domain | sheep | X | | BD Transduction Laboratories |
| | SorCS2 goat | Extracellular domain | goat | X | X | |
| | #5422 | Extracellular domain | rabbit | X | X | Hermey et al, Biochem. J., 395: 285-93, 2006 |
| | #5431 | 28 C-terminal amino acids | rabbit | X | X | |
| | SorCS2-prp | propeptide | rabbit | X | | Schousboe Sjoegaard, Dissertation, Aarhus University, 2005 |

TABLE 1-continued

| | | Antibodies against Vps10p-domain receptors | | | | |
|---|---|---|---|---|---|---|
| Receptor | Name | Antigen | Species | Western | IH/IC | Ref. |
| | M1 | Extracellular domain | mouse | | X | Roland Holst, Master of Science Thesis, Aarhus University, 2006 |
| | M3 | Extracellular domain | mouse | | X | Roland Holst, Master of Science Thesis, Aarhus University, 2006 |
| | M4 | Extracellular domain | mouse | | X | Roland Holst, Master of Science Thesis, Aarhus University, 2006 |
| | M7 | Extracellular domain | mouse | | X | Roland Holst, Master of Science Thesis, Aarhus University, 2006 |
| | M9 | Extracellular domain | mouse | | X | Roland Holst, Master of Science Thesis, Aarhus University, 2006 |
| | M10 | Extracellular domain | mouse | | X | Roland Holst, Master of Science Thesis, Aarhus University, 2006 |
| | M13 | Extracellular domain | mouse | X | | Roland Holst, Master of Science Thesis, Aarhus University, 2006 |
| | M15 | Extracellular domain | mouse | | X | Roland Holst, Master of Science Thesis, Aarhus University, 2006 |
| | M18 | Extracellular domain | mouse | X | X | Roland Holst, Master of Science Thesis, Aarhus University, 2006 |
| | M19 | Extracellular domain | mouse | X | | Roland Holst, Master of Science Thesis, Aarhus University, 2006 |
| | S21 | Extracellular domain | mouse | X | | Roland Holst, Master of Science Thesis, Aarhus University, 2006 |
| | SorCS2-GST-73aa | Extracellular domain | rabbit | X | | |
| | SorCS2-GST-100aa | Extracellular domain | rabbit | X | | |
| | SorCS2-GST-172aa | Extracellular domain | rabbit | X | | |
| SorCS3 | SorCS3-N | extracellular domain | rabbit | X | | |

TABLE 1-continued

Antibodies against Vps10p-domain receptors

| Receptor | Name | Antigen | Species | Western | IH/IC | Ref. |
|---|---|---|---|---|---|---|
| | SorCS3-C | 15 C-terminal aa | rabbit | X | | |
| | Sort3 N Term #5389 | N-terminal domain | rabbit | X | X | Westergaard et al, FEBS Lett. 579: 1172-6, 2005 |
| | #5432 | Extracellular domain | rabbit | X | X | |
| | MAB3067 | Extracellular domain | mouse | X | | BD Transduction Laboratories |
| | MAB30671 | Extracellular domain | mouse | X | | BD Transduction Laboratories |
| | AF3326 | Extracellular domain | goat | X | | BD Transduction Laboratories |
| | SorCS3 goat | Extracellular domain | goat | X | | |

Generic Use of an Antibody to Inhibit Binding of a Ligand

An antibody binds tightly to a particular target molecule, thereby either inactivating it directly or marking it for destruction. The antibody recognizes its target (antigen) with remarkable specificity and strength dictated by the sum of many chemical forces, including hydrogen bonds, hydrophobic and van der Waal's forces, as well as ionic interactions. In general, the more complex the target is chemically, the more immunogenic it will be. The antigenic determinant may encompass short linear amino acid stretches or a more complicated, three-dimensional protein module.

Procedures for Making Antibodies

Polyclonal and monoclonal antibodies directed against a specific antigen, or epitope of an antigen, can be produced according to standard procedures (see e.g. Antibodies—A laboratory Manual by Ed Harlow and David Lane, Cold Spring Harbor Laboratory 1998, ISBN 0-87969-314-2). The procedure for subsequent generation of humanized antibodies or fragments thereof has also been described (e.g. A. M. Scott et al, Cancer Research 60:3254-3261, 2000; A. Nissim and Y. Chernajovsky, Handb. Exp. Pharmacol. 181:3-18, 2008; A. Mountain and J. R. Adair, Biotechnol. Genet. Eng. Rev. 10:1-142, 1992).

General Expectations of Success in Making Antibodies

It is possible to generate antibodies against any peptide motif of choice using short synthetic oligopeptides that encompass the desired target epitope. Therefore, it is guaranteed that antibodies against ligand binding sites on receptors can be generated. Whether or not individual antibody species have the potential to inhibit ligand binding simply depends on the fact that the affinity of the immunoglobulin for the receptor exceeds that of the ligand. In the end, it is a matter of screening the inhibitory potential of a number of individual antibodies to find one with the desired properties.

Screening assays for inhibitory antibodies are common knowledge and typically involve a competitive enzyme linked immunosorbent assay (ELISA). In detail, the recombinant receptor or a fragment encompassing its ligand binding motif are immobilized in replicate wells of microtiter plates. Subsequently, the wells are incubated with a solution containing the ligand. Binding of the ligand to the immobilized receptor is confirmed using an antibody that recognizes the ligand and that is coupled with a color dye reaction. Binding of the ligand to the receptor is tested in the presence of various antibodies to identify those immunoglobulin species that block ligand binding to the receptor and hence prevent color reaction in the respective microtiter plate well.

Successful Clinical Use of Antibodies

A number of therapeutic antibodies are in clinical use. Examples include Genentech's Rituxan, an antibody directed against the CD20 receptor (used in rheumatoid arthritis), Johnson & Johnson's Remicade, an antibody directed against TNF alpha receptor (in Psoriasis), Roche's Avastin, an anti-VEGF antibody used for treatment of colorectal and lung cancer, as well as Herceptin, an antibody against the receptor HRE2 used in breast cancer therapy.

Assessing binding to a receptor is routine work for the person skilled in the bio-technical field. In this regard it has to be mentioned that pro-neurotrophins as well as the Vps10p-domain receptor family were known at the priority date of this invention and binding assays involving for example pro-neurotrophins has been mentioned in for example in the article by Lee et al (2001) Science 294:1945-1948.

Accordingly, in one embodiment, the agent of the present invention is an anti-SorCS2 polyclonal or monoclonal antibody.

In another embodiment, the agent is a polyclonal anti-SorCS2 IgG.

In a further embodiment, the agent is an anti-Sortilin polyclonal antibody.

In yet another embodiment, the agent is an anti-Sortilin polyclonal antibody.

In yet another embodiment, the agent is an anti-SorLA polyclonal or monoclonal antibody.

In yet another embodiment, the agent is an anti-SorCS1 polyclonal or monoclonal antibody.

In yet another embodiment, the agent is an anti-SorCS3 polyclonal or monoclonal antibody.

SorCS1 Knock-Out Mouse

In an important aspect the present invention relates to a transgenic knock-out mouse in which the endogenous Vps10p-domain receptor SorCS1 genes have been disrupted to abolish expression of a functional receptor, and wherein said mouse exhibits a reduced response with regard to long term depression and long term potentiation.

In a further embodiment the gene disruption of the transgenic mouse as defined herein above comprises a deletion of the SorCS1 receptor gene nucleotide sequences encoding the start codon or a region of the mouse SorCS1 receptor from the extracellular domain, transmembrane domain, or the cytoplasmic domain.

Thus, in one aspect, the present invention relates to a transgenic knock-out mouse in which the endogenous Vps10p-domain receptor SorCS1 genes have been disrupted to abolish expression of a functional receptor, and wherein said mouse exhibits an altered mental behaviour relatively to a non-transgenic control mouse.

SorCS2 Knock-Out Mouse

In an important aspect the present invention relates to a transgenic knock-out mouse in which the endogenous Vps10p-domain receptor SorCS2 genes have been disrupted to abolish expression of a functional receptor, and wherein said mouse exhibits a reduced response with regard to long term depression and long term potentiation.

In a further embodiment the gene disruption of the transgenic mouse as defined herein above comprises a deletion of the SorCS2 receptor gene nucleotide sequences encoding the start codon or a region of the mouse SorCS2 receptor from the extracellular domain, transmembrane domain, or the cytoplasmic domain.

Thus, in one aspect, the present invention relates to a transgenic knock-out mouse in which the endogenous Vps10p-domain receptor SorCS2 genes have been disrupted to abolish expression of a functional receptor, and wherein said mouse exhibits an altered mental behaviour relatively to a non-transgenic control mouse.

Methods of Screening for Agents of the Invention

The present invention provides specific targets and methods for screening and evaluating candidate agents capable of regulating neuronal activity by modulating signalling through a Vps10p-domain receptor, for use in a method of treatment of mental and behavioural disorders, wherein the neuronal activity is measured by:
a. Long-Term Depression, and/or
b. Early and Late-Phase Long Term Potentiation, and/or
c. GABAergic activity.

While the screening of a large number of peptides for a certain physiological activity may be a laborious undertaking, the exact disclosures of the assay herein to be carried out enables the skilled person to reproduce the present invention without undue burden of experimentation and without needing inventive skill.

This is also confirmed in T 21/05, wherein paragraph 11 states: " . . . Screening a large number of peptides for a certain physiological activity may be a laborious undertaking. However, the Board is convinced that the exact disclosure of the assay to be carried out enable a skilled person to reproduce the present invention, possible in a time-consuming and cumbersome way, but in the given circumstances, without undue burden of experimentation and without needing inventive skill".

For this purpose screening libraries of candidate agents are readily available for purchase on the market. Whether a library is a peptide library or a chemical library does not have any impact in the present situation since screening of chemical libraries is also routine work. In fact screening of chemical libraries is a service offered by commercial companies, and it is clear from their presentation material (See e.g. http://www.analyticon.com/) that they do not consider the screening work as such to be inventive.

In one important embodiment, the present invention concerns a method for screening a candidate agent for the ability to reduce or inhibit mental behaviour in the transgenic mouse as defined herein above, said method comprising the steps of:
a. providing a first and a second transgenic mouse as defined herein above;
b. administering to said first transgenic mouse a candidate agent, and
c. comparing mental behaviour of said first transgenic mouse of step (b) to the mental behaviour of said second transgenic mouse of step (a) not administered said candidate agent; wherein a reduction in mental behaviour in said first transgenic mouse administered said candidate agent relative to said second transgenic mouse not administered said candidate agent indicates that the candidate agent reduces mental behavior.

In a further embodiment, the present invention relate to a method for screening a candidate agent for the ability to reduce a mental and behavioural condition in the transgenic mouse as defined herein above comprising:
a. providing a transgenic mouse as defined herein above;
b. providing wild type mouse lacking the gene disruption as defined herein above; and
c. providing a control wild type mouse lacking the gene disruption as defined herein above; and
d. administering to said first wild-type mouse (b) a candidate agent, and comparing mental behaviour of said transgenic mouse of step (a) to the mental behaviour of said wild-type mouse of step (b) administered said candidate agent with to the mental behaviour of said control wild-type mouse of step (c) not administered said candidate agent; wherein a reduction in mental behaviour in said wild type mouse (b) administered said candidate agent to a level comparable with said second transgenic mouse not administered said candidate agent relatively to the control wild-type mouse (c) indicates that the candidate agent reduces mental behavior.

Pharmaceutical Composition and Administration Forms

The main routes of drug delivery, in the treatment method are intravenous, oral, and topical. Other drug-administration methods, such as subcutaneous injection or via inhalation, which are effective to deliver the drug to a target site or to introduce the drug into the bloodstream, are also contemplated.

The mucosal membrane to which the pharmaceutical preparation of the invention is administered may be any mucosal membrane of the mammal to which the biologically active substance is to be given, e.g. in the nose, vagina, eye, mouth, genital tract, lungs, gastrointestinal tract, or rectum, preferably the mucosa of the nose, mouth or vagina.

Compounds of the invention may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. The compounds may also be administered by inhalation, which is by intranasal and oral inhalation administration. Appropriate dosage forms for such administration, such as an aerosol formulation or a metered dose inhaler, may be prepared by conventional techniques.

The compounds according to the invention may be administered with at least one other compound. The compounds may be administered simultaneously, either as separate formulations or combined in a unit dosage form, or administered sequentially.

In one embodiment of the present invention, the dosage of the active ingredient of the pharmaceutical composition as defined herein above, is between 10 µg to 500 mg per kg body mass.

Formulations

Whilst it is possible for the compounds or salts of the present invention to be administered as the raw chemical, it is preferred to present them in the form of a pharmaceutical formulation. Accordingly, the present invention further provides a pharmaceutical formulation, for medicinal application, which comprises a compound of the present invention or a pharmaceutically acceptable salt thereof, as herein defined, and a pharmaceutically acceptable carrier therefore.

The compounds of the present invention may be formulated in a wide variety of oral administration dosage forms. The pharmaceutical compositions and dosage forms may comprise the compounds of the invention or its pharmaceutically acceptable salt or a crystal form thereof as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, wetting agents, tablet disintegrating agents, or an encapsulating material.

Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like.

In powders, the carrier is a finely divided solid which is a mixture with the finely divided active component. In tablets, the active component is mixed with the carrier having the necessary binding capacity in suitable proportions and compacted in the shape and size desired. Powders and tablets preferably contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Also included are solid form preparations which are intended to be converted, shortly before use, to liquid form preparations for oral administration. Such liquid forms include solutions, suspensions, and emulsions. These preparations may contain, in addition to the active component, colorants, flavours, buffers, artificial and natural sweeteners, dispersants, thickeners, solubilizing agents, and the like.

Other forms suitable for oral administration include liquid form preparations including emulsions, syrups, elixirs, aqueous solutions, aqueous suspensions, toothpaste, gel dentrifrice, chewing gum, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavours, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavours, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides; (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-.beta.-aminopropionates, and 2-alkyl-imidazoline quaternary ammonium salts, and (e) mixtures thereof.

The parenteral formulations typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The compounds of the invention can also be delivered topically. Regions for topical administration include the skin surface and also mucous membrane tissues of the vagina, rectum, nose, mouth, and throat. Compositions for topical administration via the skin and mucous membranes should not give rise to signs of irritation, such as swelling or redness.

The topical composition may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example. Methods for preparing such compositions are well known in the pharmaceutical industry.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or nonionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Transdermal Delivery

The pharmaceutical agent-chemical modifier complexes described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent-chemical modifier complex to the body. See Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1-3, Kydonieus and Berner (eds.), CRC Press, (1987). Such dosage forms can be made by dissolving, dispersing, or otherwise incorporating the pharmaceutical agent-chemical modifier complex in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Passive Transdermal Drug Delivery

A variety of types of transdermal patches will find use in the methods described herein. For example, a simple adhesive patch can be prepared from a backing material and an acrylate adhesive. The pharmaceutical agent-chemical modifier complex and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver the pharmaceutical agent-chemical modifier complex. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

The liquid reservoir patch will also find use in the methods described herein. This patch comprises an impermeable or semipermeable, heat sealable backing material, a heat sealable membrane, an acrylate based pressure sensitive skin adhesive, and a siliconized release liner. The backing is heat sealed to the membrane to form a reservoir which can then be filled with a solution of the complex, enhancers, gelling agent, and other excipients.

Foam matrix patches are similar in design and components to the liquid reservoir system, except that the gelled pharmaceutical agent-chemical modifier solution is constrained in a thin foam layer, typically a polyurethane. This foam layer is situated between the backing and the membrane which have been heat sealed at the periphery of the patch.

For passive delivery systems, the rate of release is typically controlled by a membrane placed between the reservoir and the skin, by diffusion from a monolithic device, or by the skin itself serving as a rate-controlling barrier in the delivery system. See U.S. Pat. Nos. 4,816,258; 4,927,408; 4,904,475; 4,588,580, 4,788,062; and the like. The rate of drug delivery will be dependent, in part, upon the nature of the membrane. For example, the rate of drug delivery across membranes within the body is generally higher than across dermal barriers. The rate at which the complex is delivered from the device to the membrane is most advantageously controlled by the use of rate-limiting membranes which are placed between the reservoir and the skin. Assuming that the skin is sufficiently permeable to the complex (i.e., absorption through the skin is greater than the rate of passage through the membrane), the membrane will serve to control the dosage rate experienced by the patient.

Suitable permeable membrane materials may be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other conventional components of therapeutic products, depending upon the desired device characteristics. For example, the compositions according to this invention may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, analgesics, and antipruritic agents.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The active compound may be formulated into a suppository comprising, for example, about 0.5% to about 50% of a compound of the invention, disposed in a polyethylene glycol (PEG) carrier (e.g., PEG 1000 [96%] and PEG 4000 [4%].

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example with a dropper, pipette or spray. The formulations may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

The compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Pharmaceutically Acceptable Salts

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

Accordingly, in one aspect the invention relates to a pharmaceutical composition-comprising an agent as defined herein above.

In one embodiment the agent as defined herein above, is selected from the group consisting of small organic compounds, oligo-peptides, proteins and monoclonal or polyclonal antibodies.

In one embodiment the pharmaceutical composition as defined herein above comprises a pharmaceutically acceptable carrier.

In one embodiment of the present invention the pH of the pharmaceutical composition as defined herein above is between pH 5 and pH 9.

In one embodiment the pharmaceutical composition as defined herein above is formulated for administration by injection, suppository, oral administration, sublingual tablet or spray, cutaneous administration, inhalation or for local administration using an implantable biocompatible capsule.

In a further embodiment the injection is intravenous, intramuscular, intraspinal, intraperitoneal, subcutaneous, a bolus or a continuous administration.

In one embodiment the pharmaceutical composition according to the present invention is administered at intervals of 30 minutes to 24 hours.

In a further embodiment the pharmaceutical composition according to the present invention is administered at intervals of 1 to 6 hours.

In a further embodiment the pharmaceutical composition according to the present invention is administered at intervals of 6 to 72 hours.

Second Active Ingredient

In one embodiment the pharmaceutical composition as defined herein above comprises a second active ingredient.

In one embodiment, the second active ingredient is selected from the group consisting of Antidepressants, Anticonvulsants, Local anaesthetics, Opiods, NMDA antagonists, anti-psychotic medications and anxiolytics.

In a further embodiment, the anti-psychotic medications are selected from the group consisting of clozapin, risperidone, aripiprazole, quetiapine, and olanzapine.

In a further embodiment, the anxiolytics are selected from the group consisting of benzodiazepines, buspiron, acepromazin, dixyrazin, and hydroxizin.

In a further embodiment, the antidepressants are selected from the group consisting of selective serotonin reuptake inhibitors (SSRI), Tricyclic antidepressants and Amitryptilin.

In a further embodiment, the Opiods, are selected from the group consisting of Morphine, fentanyl and oxycodone.

In a further embodiment, the NMDA antagonists are selected from the group consisting of Ketamine, memantine and amantadine.

In one important aspect, the present invention relates to a method of treatment of mental and behavioural disorders as defined herein below, by regulating neuronal activity in a patient in need thereof, said method comprising modulating signalling through a Vps10p-domain receptor by administering to said patient, the pharmaceutical composition as defined herein above.

Kit of Parts

In one aspect the present invention relates to a kit in parts comprising:
- a pharmaceutical composition as defined herein above
- a medical instrument or other means for administering the medicament
- instructions on how to use the kit in parts.
- optionally a second active ingredient as defined herein above Indications The agent of the present invention is useful for treating Mental and behavioural disorders as defined by the WHO on the following URL: http://www.who.int/classifications/apps/icd/icd10online/ at the date of filing of the present application. The mental and behavioural disorders (F00-F99) are thus classified as outlined below:

(F00-F09) Organic, including symptomatic, mental disorders
  (F00.) Dementia in Alzheimer's disease
  (F01.) Vascular dementia
    (F01.1) Multi-infarct dementia
  (F02.) Dementia in other diseases classified elsewhere
    (F02.0) Dementia in Pick's disease
    (F02.1) Dementia in Creutzfeldt-Jakob disease
    (F02.2) Dementia in Huntington's disease
    (F02.3) Dementia in Parkinson's disease
    (F02.4) Dementia in human immunodeficiency virus (HIV) disease
  (F03.) Unspecified dementia
  (F04.) Organic amnesic syndrome, not induced by alcohol and other psychoactive substances
  (F05.) Delirium, not induced by alcohol and other psychoactive substances
  (F06.) Other mental disorders due to brain damage and dysfunction and to physical disease
    (F06.0) Organic hallucinosis
    (F06.1) Organic catatonic disorder
    (F06.2) Organic delusional (schizophrenia-like) disorder
    (F06.3) Organic mood (affective) disorders
    (F06.4) Organic anxiety disorder
    (F06.5) Organic dissociative disorder
    (F06.6) Organic emotionally labile (asthenic) disorder
    (F06.7) Mild cognitive disorder
    (F06.8) Other specified mental disorders due to brain damage and dysfunction and to physical disease
    (F06.9) Unspecified mental disorder due to brain damage and dysfunction and to physical disease
    Organic brain syndrome NOS
  (F07.) Personality and behavioural disorders due to brain disease, damage and dysfunction
    (F07.0) Organic personality disorder
    (F07.1) Postencephalitic syndrome
    (F07.2) Postconcussional syndrome
    (F07.8) Other organic personality and behavioural disorders due to brain disease, damage and dysfunction
    (F07.9) Unspecified organic personality and behavioural disorder due to brain disease, damage and dysfunction
  (F09.) Unspecified organic or symptomatic mental disorder (F10-F19) Mental and behavioural disorders due to psychoactive substance use
  (F10.) Mental and behavioural disorders due to use of alcohol
    (F10.0) acute intoxication
    (F10.1) harmful use
    (F10.2) dependence syndrome
    (F10.3) withdrawal state
    (F10.4) withdrawal state with delirium
    (F10.5) psychotic disorder
    (F10.6) amnesic syndrome
    (F10.7) psychotic disorder
    (F10.8) other mental and behavioural disorder
    (F10.9) unspecified mental and behavioural disorder
  (F11.) Mental and behavioural disorders due to use of opioids
    (F11.0) acute intoxication
    (F11.1) harmful use
    (F11.2) dependence syndrome
    (F11.3) withdrawal state
    (F11.4) withdrawal state with delirium
    (F11.5) psychotic disorder
    (F11.6) amnesic syndrome (F11.7) psychotic disorder
(F11.8) other mental and behavioural disorder
(F11.9) unspecified mental and behavioural disorder
(F12.) Mental and behavioural disorders due to use of cannabinoids
(F12.0) acute intoxication
(F12.1) harmful use
(F12.2) dependence syndrome
(F12.3) withdrawal state
(F12.4) withdrawal state with delirium
(F12.5) psychotic disorder
(F12.6) amnesic syndrome
(F12.7) psychotic disorder
(F12.8) other mental and behavioural disorder
(F12.9) unspecified mental and behavioural disorder
(F13.) Mental and behavioural disorders due to use of sedatives or hypnotics
(F13.0) acute intoxication
(F13.1) harmful use
(F13.2) dependence syndrome
(F13.3) withdrawal state
(F13.4) withdrawal state with delirium
(F13.5) psychotic disorder
(F13.6) amnesic syndrome
(F13.7) psychotic disorder
(F13.8) other mental and behavioural disorder
(F13.9) unspecified mental and behavioural disorder
(F14.) Mental and behavioural disorders due to use of cocaine
(F14.0) acute intoxication
(F14.1) harmful use
(F14.2) dependence syndrome
(F14.3) withdrawal state
(F14.4) withdrawal state with delirium
(F14.5) psychotic disorder
(F14.6) amnesic syndrome
(F14.7) psychotic disorder
(F14.8) other mental and behavioural disorder
(F14.9) unspecified mental and behavioural disorder
(F15.) Mental and behavioural disorders due to use of other stimulants, including caffeine
(F15.0) acute intoxication
(F15.1) harmful use
(F15.2) dependence syndrome
(F15.3) withdrawal state
(F15.4) withdrawal state with delirium
(F15.5) psychotic disorder
(F15.6) amnesic syndrome
(F15.7) psychotic disorder
(F15.8) other mental and behavioural disorder
(F15.9) unspecified mental and behavioural disorder
(F16.) Mental and behavioural disorders due to use of hallucinogens
(F16.0) acute intoxication
(F16.1) harmful use
(F16.2) dependence syndrome
(F16.3) withdrawal state
(F16.4) withdrawal state with delirium
(F16.5) psychotic disorder
(F16.6) amnesic syndrome
(F16.7) psychotic disorder
(F16.8) other mental and behavioural disorder
(F16.9) unspecified mental and behavioural disorder
(F17.) Mental and behavioural disorders due to use of tobacco
(F17.0) acute intoxication
(F17.1) harmful use
(F17.2) dependence syndrome
(F17.3) withdrawal state
(F17.4) withdrawal state with delirium
(F17.5) psychotic disorder
(F17.6) amnesic syndrome
(F17.7) psychotic disorder
(F17.8) other mental and behavioural disorder
(F17.9) unspecified mental and behavioural disorder
(F18.) Mental and behavioural disorders due to use of volatile solvents
(F18.0) acute intoxication
(F18.1) harmful use
(F18.2) dependence syndrome
(F18.3) withdrawal state
(F18.4) withdrawal state with delirium
(F18.5) psychotic disorder
(F18.6) amnesic syndrome
(F18.7) psychotic disorder
(F18.8) other mental and behavioural disorder
(F18.9) unspecified mental and behavioural disorder
(F19.) Mental and behavioural disorders due to multiple drug use and use of other psychoactive substances
(F19.0) acute intoxication
(F19.1) harmful use
(F19.2) dependence syndrome
(F19.3) withdrawal state
(F19.4) withdrawal state with delirium
(F19.5) psychotic disorder
(F19.6) amnesic syndrome
(F19.7) psychotic disorder
(F19.8) other mental and behavioural disorder
(F19.9) unspecified mental and behavioural disorder
(F20-F29) Schizophrenia, schizotypal and delusional disorders
(F20.) Schizophrenia
(F20.0) Paranoid schizophrenia
(F20.1) Hebephrenic schizophrenia
(F20.2) Catatonic schizophrenia
(F20.3) Undifferentiated schizophrenia
(F20.4) Post-schizophrenic depression
(F20.5) Residual schizophrenia
(F20.6) Simple schizophrenia
(F20.8) Other schizophrenia
Cenesthopathic schizophrenia
Schizophreniform disorder NOS
Schizophreniform psychosis NOS
(F20.9) Schizophrenia, unspecified
(F21.) Schizotypal disorder
(F22.) Persistent delusional disorders
(F22.0) Delusional disorder
(F22.8) Other persistent delusional disorders
Delusional dysmorphophobia
Involutional paranoid state
Paranoia querulans
(F22.9) Persistent delusional disorder, unspecified
(F23.) Acute and transient psychotic disorders
(F23.0) Acute polymorphic psychotic disorder without symptoms of schizophrenia
(F23.1) Acute polymorphic psychotic disorder with symptoms of schizophrenia
(F23.2) Acute schizophrenia-like psychotic disorder
(F23.3) Other acute predominantly delusional psychotic disorders
(F23.8) Other acute and transient psychotic disorders
(F23.9) Acute and transient psychotic disorder, unspecified (F24.) Induced delusional disorder
  Folie à deux
  Induced paranoid disorder
  Induced psychotic disorder
(F25.) Schizoaffective disorders
  (F25.0) Schizoaffective disorder, manic type
  (F25.1) Schizoaffective disorder, depressive type
  (F25.2) Schizoaffective disorder, mixed type
  (F25.8) Other schizoaffective disorders
  (F25.9) Schizoaffective disorder, unspecified
(F28.) Other nonorganic psychotic disorders
  Chronic hallucinatory psychosis
(F29.) Unspecified nonorganic psychosis
(F30-F39) Mood (affective) disorders
  (F30.) Manic episode
    (F30.0) Hypomania
    (F30.1) Mania without psychotic symptoms
    (F30.2) Mania with psychotic symptoms
    (F30.8) Other manic episodes
    (F30.9) Manic episode, unspecified
  (F31.) Bipolar affective disorder
    (F31.0) Bipolar affective disorder, current episode hypomanic
    (F31.1) Bipolar affective disorder, current episode manic without psychotic symptoms
    (F31.2) Bipolar affective disorder, current episode manic with psychotic symptoms
    (F31.3) Bipolar affective disorder, current episode mild or moderate depression
    (F31.4) Bipolar affective disorder, current episode severe depression without psychotic symptoms
    (F31.5) Bipolar affective disorder, current episode severe depression with psychotic symptoms
    (F31.6) Bipolar affective disorder, current episode mixed
    (F31.7) Bipolar affective disorder, currently in remission
    (F31.8) Other bipolar affective disorders
    Bipolar II disorder
    Recurrent manic episodes NOS
    (F31.9) Bipolar affective disorder, unspecified
  (F32.) Depressive episode
    (F32.0) Mild depressive episode
    (F32.1) Moderate depressive episode
    (F32.2) Severe depressive episode without psychotic symptoms
    (F32.3) Severe depressive episode with psychotic symptoms
    (F32.8) Other depressive episodes
    Atypical depression
    Single episodes of "masked" depression NOS
    (F32.9) Depressive episode, unspecified
  (F33.) Recurrent depressive disorder
    (F33.0) Recurrent depressive disorder, current episode mild
    (F33.1) Recurrent depressive disorder, current episode moderate
    (F33.2) Recurrent depressive disorder, current episode severe without psychotic symptoms
    (F33.3) Recurrent depressive disorder, current episode severe with psychotic symptoms
    (F33.4) Recurrent depressive disorder, currently in remission
    (F33.8) Other recurrent depressive disorders
    (F33.9) Recurrent depressive disorder, unspecified
  (F34.) Persistent mood (affective) disorders
    (F34.0) Cyclothymia
    (F34.1) Dysthymia
    (F34.8) Other persistent mood (affective) disorders
    (F34.9) Persistent mood (affective) disorder, unspecified
  (F38.) Other mood (affective) disorders
    (F38.0) Other single mood (affective) disorders
    Mixed affective episode
    (F38.1) Other recurrent mood (affective) disorders
    Recurrent brief depressive episodes
    (F38.8) Other specified mood (affective) disorders
  (F39.) Unspecified mood (affective) disorder
(F40-F48) Neurotic, stress-related and somatoform disorders
  (F40.) Phobic anxiety disorders
    (F40.0) Agoraphobia
    (F40.1) Social phobias
    Anthropophobia
    Social neurosis
    (F40.2) Specific (isolated) phobias
    Acrophobia
    Animal phobias
    Claustrophobia
    Simple phobia
    (F40.8) Other phobic anxiety disorders
    (F40.9) Phobic anxiety disorder, unspecified
    Phobia NOS
    Phobic state NOS
  (F41.) Other anxiety disorders
    (F41.0) Panic disorder (episodic paroxysmal anxiety)
    (F41.1) Generalized anxiety disorder
  (F42.) Obsessive-compulsive disorder
  (F43.) Reaction to severe stress, and adjustment disorders
    (F43.0) Acute stress reaction
    (F43.1) Post-traumatic stress disorder
    (F43.2) Adjustment disorder
  (F44.) Dissociative (conversion) disorders
    (F44.0) Dissociative amnesia
    (F44.1) Dissociative fugue
    (F44.2) Dissociative stupor
    (F44.3) Trance and possession disorders
    (F44.4) Dissociative motor disorders
    (F44.5) Dissociative convulsions
    (F44.6) Dissociative anaesthesia and sensory loss
    (F44.7) Mixed dissociative (conversion) disorders
    (F44.8) Other dissociative (conversion) disorders
    Ganser's syndrome
    Multiple personality
    (F44.9) Dissociative (conversion) disorder, unspecified
  (F45.) Somatoform disorders
    (F45.0) Somatization disorder
    Briquet's disorder
    Multiple psychosomatic disorder
    (F45.1) Undifferentiated somatoform disorder
    (F45.2) Hypochondriacal disorder
    Body dysmorphic disorder
    Dysmorphophobia (nondelusional)
    Hypochondriacal neurosis
    Hypochondriasis
    Nosophobia
    (F45.3) Somatoform autonomic dysfunction
    Cardiac neurosis
    Da Costa's syndrome
    Gastric neurosis
    Neurocirculatory asthenia
    (F45.4) Persistent somatoform pain disorder
    Psychalgia (F45.8) Other somatoform disorders
(F45.9) Somatoform disorder, unspecified
(F48.) Other neurotic disorders
  (F48.0) Neurasthenia
  (F48.1) Depersonalization-derealization syndrome
  (F48.8) Other specified neurotic disorders
  Dhat syndrome
  Occupational neurosis, including writer's cramp
  Psychasthenia
  Psychasthenic neurosis
  Psychogenic syncope
  (F48.9) Neurotic disorder, unspecified
  Neurosis NOS (F50-F59) Behavioural syndromes associated with physiological disturbances and physical factors
  (F50.) Eating disorders
    (F50.0) Anorexia nervosa
    (F50.1) Atypical anorexia nervosa
    (F50.2) Bulimia nervosa
    (F50.3) Atypical bulimia nervosa
    (F50.4) Overeating associated with other psychological disturbances
    (F50.5) Vomiting associated with other psychological disturbances
    (F50.8) Other eating disorders
    Pica in adults
    (F50.9) Eating disorder, unspecified
  (F51.) Nonorganic sleep disorders
    (F51.0) Nonorganic insomnia
    (F51.1) Nonorganic hypersomnia
    (F51.2) Nonorganic disorder of the sleep-wake schedule
    (F51.3) Sleepwalking (somnambulism)
    (F51.4) Sleep terrors (night terrors)
    (F51.5) Nightmares
  (F52.) Sexual dysfunction, not caused by organic disorder or disease
    (F52.0) Lack or loss of sexual desire
    (F52.1) Sexual aversion and lack of sexual enjoyment
    (F52.2) Failure of genital response
    (F52.3) Orgasmic dysfunction
    (F52.4) Premature ejaculation
    (F52.5) Nonorganic vaginismus
    (F52.6) Nonorganic dyspareunia
    (F52.7) Excessive sexual drive
    (F52.8) Other sexual dysfunction, not caused by organic disorder or disease
    (F52.9) Unspecified sexual dysfunction, not caused by organic disorder or disease
  (F53.) Mental and behavioural disorders associated with the puerperium, not elsewhere classified
    (F53.0) Mild mental and behavioural disorders associated with the puerperium, not elsewhere classified
    Postnatal depression NOS
    Postpartum depression NOS
    (F53.1) Severe mental and behavioural disorders associated with the puerperium, not elsewhere classified
    Puerperal psychosis NOS
  (F54.) Psychological and behavioural factors associated with disorders or diseases classified elsewhere
  (F55.) Abuse of non-dependence-producing substances
  (F59.) Unspecified behavioural syndromes associated with physiological disturbances and physical factors (F60-F69) Disorders of adult personality and behaviour
  (F60.) Specific personality disorders
    (F60.0) Paranoid personality disorder
    (F60.1) Schizoid personality disorder
    (F60.2) Dissocial personality disorder
    Antisocial personality disorder
    (F60.3) Emotionally unstable personality disorder
    Borderline personality disorder
    (F60.4) Histrionic personality disorder
    (F60.5) Anankastic personality disorder
    Obsessive-compulsive personality disorder
    (F60.6) Anxious (avoidant) personality disorder
    (F60.7) Dependent personality disorder
    (F60.8) Other specific personality disorders
    Eccentric personality disorder
    "Haltlose" type personality disorder
    Immature personality disorder
    Narcissistic personality disorder
    Passive-aggressive personality disorder
    Psychoneurotic personality disorder
    (F60.9) Personality disorder, unspecified
  (F61.) Mixed and other personality disorders
  (F62.) Enduring personality changes, not attributable to brain damage and disease
  (F63.) Habit and impulse disorders
    (F63.0) Pathological gambling
    (F63.1) Pathological fire-setting (pyromania)
    (F63.2) Pathological stealing (kleptomania)
    (F63.3) Trichotillomania
  (F64.) Gender identity disorders
    (F64.0) Transsexualism
    (F64.1) Dual-role transvestism
    (F64.2) Gender identity disorder of childhood
  (F65.) Disorders of sexual preference
    (F65.0) Fetishism
    (F65.1) Fetishistic transvestism
    (F65.2) Exhibitionism
    (F65.3) Voyeurism
    (F65.4) Paedophilia
    (F65.5) Sadomasochism
    (F65.6) Multiple disorders of sexual preference
    (F65.8) Other disorders of sexual preference
    Frotteurism
    Necrophilia
  (F66.) Psychological and behavioural disorders associated with sexual development and orientation
    (F66.0) Sexual maturation disorder
    (F66.1) Ego-dystonic sexual orientation
    (F66.2) Sexual relationship disorder
    (F66.8) Other psychosexual development disorders
    (F66.9) Psychosexual development disorder, unspecified
  (F68.) Other disorders of adult personality and behaviour
    (F68.0) Elaboration of physical symptoms for psychological reasons
    (F68.1) Intentional production or feigning of symptoms or disabilities, either physical or psychological (factitious disorder)
    Munchausen syndrome
    (F68.8) Other specified disorders of adult personality and behaviour
(F69.) Unspecified disorder of adult personality and behaviour (F70-F79) Mental retardation
  (F70.) Mild mental retardation
  (F71.) Moderate mental retardation
  (F72.) Severe mental retardation
  (F73.) Profound mental retardation
  (F78.) Other mental retardation
  (F79.) Unspecified mental retardation (F80-F89) Disorders of psychological development
- (F80.) Specific developmental disorders of speech and language
  - (F80.0) Specific speech articulation disorder
  - (F80.1) Expressive language disorder
  - (F80.2) Receptive language disorder
  - Wernicke's aphasia
  - (F80.3) Acquired aphasia with epilepsy (Landau-Kleffner)
  - (F80.8) Other developmental disorders of speech and language
  - Lisping
  - (F80.9) Developmental disorder of speech and language, unspecified
- (F81.) Specific developmental disorders of scholastic skills
  - (F81.0) Specific reading disorder
  - Developmental dyslexia
  - (F81.1) Specific spelling disorder
  - (F81.2) Specific disorder of arithmetical skills
  - Developmental acalculia
  - Gerstmann syndrome
  - (F81.3) Mixed disorder of scholastic skills
  - (F81.8) Other developmental disorders of scholastic skills
  - (F81.9) Developmental disorder of scholastic skills, unspecified
- (F82.) Specific developmental disorder of motor function
- Developmental Dyspraxia
- (F83.) Mixed specific developmental disorders
- (F84.) Pervasive developmental disorders
  - (F84.0) Childhood autism
  - (F84.2) Rett's syndrome
  - (F84.4) Overactive disorder associated with mental retardation and stereotyped movements
  - (F84.5) Asperger's syndrome
- (F88.) Other disorders of psychological development
- (F89.) Unspecified disorder of psychological development (F90-F98) Behavioural and emotional disorders with onset usually occurring in childhood and adolescence
- (F90.) Hyperkinetic disorders
  - (F90.0) Disturbance of activity and attention
  - Attention Deficit Disorder with Hyperactivity
  - Attention deficit hyperactivity disorder
  - Attention deficit syndrome with hyperactivity
  - (F90.1) Hyperkinetic conduct disorder
  - (F90.8) Other hyperkinetic disorders
  - (F90.9) Hyperkinetic disorder, unspecified
- (F91.) Conduct disorders
  - (F91.0) Conduct disorder confined to the family context
  - (F91.1) Unsocialized conduct disorder
  - (F91.2) Socialized conduct disorder
  - (F91.3) Oppositional defiant disorder
  - (F91.8) Other conduct disorders
  - (F91.9) Conduct disorder, unspecified
- (F92.) Mixed disorders of conduct and emotions
  - (F92.0) Depressive conduct disorder
  - (F92.8) Other mixed disorders of conduct and emotions
  - (F92.9) Mixed disorder of conduct and emotions, unspecified
- (F93.) Emotional disorders with onset specific to childhood
  - (F93.0) Separation anxiety disorder of childhood
  - (F93.1) Phobic anxiety disorder of childhood
  - (F93.2) Social anxiety disorder of childhood
  - (F93.3) Sibling rivalry disorder
  - (F93.8) Other childhood emotional disorders
  - Identity disorder
  - Overanxious disorder
  - (F93.9) Childhood emotional disorder, unspecified
- (F94.) Disorders of social functioning with onset specific to childhood and adolescence
  - (F94.0) Elective mutism
  - (F94.1) Reactive attachment disorder of childhood
  - (F94.2) Disinhibited attachment disorder of childhood
  - (F94.8) Other childhood disorders of social functioning
  - (F94.9) Childhood disorder of social functioning, unspecified
- (F95.) Tic disorders
  - (F95.0) Transient tic disorder
  - (F95.1) Chronic motor or vocal tic disorder
  - (F95.2) Combined vocal and multiple motor tic disorder (de la Tourette)
  - (F95.8) Other tic disorders
  - (F95.9) Tic disorder, unspecified
- (F98.) Other behavioural and emotional disorders with onset usually occurring in childhood and adolescence
  - (F98.0) Nonorganic enuresis
  - (F98.1) Nonorganic encopresis
  - (F98.2) Feeding disorder of infancy and childhood
  - (F98.3) Pica of infancy and childhood
  - (F98.4) Stereotyped movement disorders
  - (F98.5) Stuttering (stammering)
  - (F98.6) Cluttering
  - (F98.8) Other specified behavioural and emotional disorders with onset usually occurring in childhood and adolescence
  - Attention deficit disorder without hyperactivity
  - Excessive masturbation
  - Nail-biting
  - Nose-picking
  - Thumb-sucking
  - (F98.9) Unspecified behavioural and emotional disorders with onset usually occurring in childhood and adolescence (F99) Unspecified mental disorder
- (F99.) Mental disorder, not otherwise specified Thus, in an important aspect, the agent of the present invention is useful for treating or preventing, or treating and preventing mental and behavioural disorders selected from the group consisting of Organic mental disorders, including symptomatic mental disorders; Mental and behavioural disorders due to psychoactive substance use; Schizophrenia, schizotypal and delusional disorders; Mood [affective] disorder; Neurotic, stress-related and somatoform disorders; Behavioural syndromes associated with physiological disturbances and physical factors; Disorders of adult personality and behaviour; Mental retardation; Disorders of psychological development; Behavioural and emotional disorders with onset usually occurring in childhood and adolescence and Unspecified mental disorder.

In one embodiment, mania is treated with sortilin or sorcs2 agonist agents or sorcs1 agonist agents of the invention.

In one embodiment, the Organic mental disorders including symptomatic mental disorders, as defined herein above, are selected from the group consisting of Dementia in Alzheimer's disease, Vascular dementia, Dementia in other diseases classified elsewhere, Unspecified dementia, Organic amnesic syndrome, not induced by alcohol and other psychoactive substances, Delirium, not induced by alcohol and other psychoactive substances, Other mental disorders due to brain damage and dysfunction and to physical disease, Organic delusional [schizophrenia-like] disorder, Personality and behavioural disorders due to brain disease, damage and dysfunction and Unspecified organic or symptomatic mental disorder.

In another embodiment, the Mental and behavioural disorders due to psychoactive substance as defined herein above are selected from the group consisting of Mental and behavioural disorders due to use of alcohol, Mental and behavioural disorders due to use of opioids, Mental and behavioural disorders due to use of cannabinoids, Mental and behavioural disorders due to use of sedatives or hypnotics, Mental and behavioural disorders due to use of cocaine, Mental and behavioural disorders due to use of other stimulants, including caffeine, Mental and behavioural disorders due to use of hallucinogens, Mental and behavioural disorders due to use of tobacco, Mental and behavioural disorders due to use of volatile solvents and Mental and behavioural disorders due to multiple drug use and use of other psychoactive substances.

In a further embodiment of the present invention, the Schizophrenia, schizotypal and delusional disorder as defined herein above, is selected from the group consisting of Schizophrenia, Schizotypal disorder, Persistent delusional disorders, Acute and transient psychotic disorders, Induced delusional disorder, Schizoaffective disorders, Other nonorganic psychotic disorders and Unspecified nonorganic psychosis.

In a further embodiment, the Mood [affective] disorder as defined herein above, is selected from the group consisting of Manic episode, Bipolar affective disorder, Depressive episode, Recurrent depressive disorder, Persistent mood [affective] disorders, Other mood [affective] disorders and Unspecified mood [affective] disorder.

In yet another embodiment of the present invention, the Neurotic, stress-related and somatoform disorder as defined herein above is selected from the group consisting of Phobic anxiety disorders; Other anxiety disorders; Obsessive-compulsive disorder; Reaction to severe stress, and adjustment disorders; Dissociative [conversion] disorders; Somatoform disorders and Other neurotic disorders.

In another embodiment of the present invention, the Behavioural syndromes associated with physiological disturbances and physical factors as defined herein above, are selected from the group consisting of Eating disorders; Nonorganic sleep disorders; Sexual dysfunction, not caused by organic disorder or disease; Mental and behavioural disorders associated with the puerperium, not elsewhere classified; Psychological and behavioural factors associated with disorders or diseases classified elsewhere; Abuse of non-dependence-producing substances and Unspecified behavioural syndromes associated with physiological disturbances and physical factors.

In another embodiment of the present invention, the Disorder of adult personality and behaviour as defined herein above, is selected from the group consisting of Specific personality disorders; Mixed and other personality disorders; Enduring personality changes, not attributable to brain damage and disease; Habit and impulse disorders; Gender identity disorders; Disorders of sexual preference; Psychological and behavioural disorders associated with sexual development and orientation; Other disorders of adult personality and behaviour and Unspecified disorder of adult personality and behaviour.

In another embodiment of the present invention, the Mental retardation as defined herein above, is selected from the group consisting of Mild mental retardation; Moderate mental retardation; Severe mental retardation; Profound mental retardation; Other mental retardation and Unspecified mental retardation.

In another embodiment of the present invention, the Disorders of psychological development as defined herein above, is selected from the group consisting of Specific developmental disorders of speech and language; Specific developmental disorders of scholastic skills; Specific developmental disorder of motor function; Mixed specific developmental disorders; Pervasive developmental disorders; Other disorders of psychological development and Unspecified disorder of psychological development.

In another embodiment of the present invention, the Behavioural and emotional disorders with onset usually occurring in childhood and adolescence, as defined herein above is selected from the group consisting of Hyperkinetic disorders; Conduct disorders; Mixed disorders of conduct and emotions; Emotional disorders with onset specific to childhood; Disorders of social functioning with onset specific to childhood and adolescence; Tic disorders and Other behavioural and emotional disorders with onset usually occurring in childhood and adolescence.

In another embodiment of the present invention, the Unspecified mental disorder is Mental disorder, not otherwise specified.

The transgenic knock out mice of the invention were generated by use of the pTK2 vector according to the standard ES cell targeting method as described by Willnow and Herz in 1994 (Willnow and Herz, 1994)

DETAILED DESCRIPTION OF THE DRAWINGS

FIG. 1: The Vps10p-domain receptor family. Their structural organization is indicated.

FIG. 2: Expression and subcellular localization of Sortilin and SorCS2 in the hippocampus. A, Sortilin expression in the dentate gyrus of WT mice brain section was visualized by immunohistochemistry using polyclonal rabbit anti-Sortilin antibodies and peroxidase staining according to standard protocol. Staining of a brain section from Sortilin −/− mice is included as negative control. B, visualization of SorCS2 expressing cells in the hippocampus by X-gal staining of a brain section from SorCS2 −/− mice. This staining procedure was performed according to standard protocol and takes advantage of a LacZ gene inserted into exon 15 of the SorCS2 gene to disrupt SorCS2 gene expression. The LacZ gene encodes β-galactosidase and the SorCS2 promoter then drives the expression. C, subcellular localization of Sortilin and SorCS2 in the hippocampus. The hippocampus from eight WT mice 8-12 weeks old were removed from the craniums and immediately transferred to 10 ml ice cold HEPES (hydroxyethylpiperazin-N2-ethansulfonacid, N-2)-buffered sucrose (0.32 M sucrose, 4 mM HEPES ph 7.4) containing freshly added protease inhibitors (0.1 mM phenylmethylsulfonylfluoride (PMSF), 1 mM Aprotinin, 10 mM Leupeptin, 10 mM Pepstatin (all from Sigma)) and homogenized using a motor driven glassteflon homogenizer (B. Braun) at 900 rpm. The homogenate (H) was centrifuged at 1000×g for 10 min generating P1 (pellet containing cell debris and nuclei) and S1 (supernatant) fractions. The resultant supernatant (S1) was centrifuged at 10000×g for 15 min generating S2 and P2, a crude synaptosomal pellet enriched with mitochondria and synaptosomes. The P2 pellet was solubilized in 15 ml HEPES-buffered sucrose containing protease inhibitors and centrifuged at 10000×g for 15 min generating S2″ and P2″, a washed crude synaptosomal pellet. The P2″ fraction was lysed by hypoosmotic shock in 9 volumes ice cold $H_2O$ containing protease inhibitors and was giving three strokes of a glass-teflon homogenizer to aid the lysis. The homogenate was adjusted to 4 mM HEPES, mixed constantly in cold room for 30 min to ensure complete lysis and then centrifuged at 25000×g for 20 min generating S3 (LS1) (crude synaptic vesicle fraction) and P3 (LP1) (lysed synaptosomal membrane fraction). The resulting supernatant (LS1) was centrifuged at 165000×g for 2 hour (45000 rpm in 70.1 Ti) generating the pellet SVP (LP2) enriched in presynaptic vesicles. The pellet P3 (LP1) was resuspended in 3.5 ml HEPES-buffered sucrose containing protease inhibitors and layered on top of a discontinuous gradient containing 0.8 to 1.0 to 1.2 M sucrose added protease inhibitors. The gradient was centrifuged at 150000×g for 2 hours in a swinging bucket rotor (30000 rpm in SW41 Ti). The fraction between the 1.0 and 1.2 M sucrose layer containing the synaptic plasma membranes was recovered and diluted to 0.32 m sucrose by adding 2.5 volumes of 4 mM HEPES pH 7.4. The suspension was centrifuged at 150000×g for 30 min (42000 rpm in 70.1 Ti) and the resulting pellet was resuspended in 1 ml 50 mM HEPES pH 7.4, 2 mM EDTA with protease inhibitors giving a synaptic plasma membrane (SPM) suspension. 700 ml of the SPM suspension was added 3 ml of ice-cold 50 mM HEPES, pH 7.4, 2 mM EDTA, plus protease inhibitors and 0.5% Triton X-100. The suspension was rotated in a cold room for 15 min and centrifuged at 32000×g (22000 rpm in 70.1 Ti) for 20 min to obtain the PDSI pellet containing post synaptic densities. The PSDI pellet was resuspended in 2 ml ice-cold 50 mM HEPES, pH 7.4, 2 mM EDTA plus protease inhibitors. 300 ml of the PSDI suspension was saved and the rest added 0.5% Triton-X 100 before rotation in cold room for 15 min. The PSDI suspension was centrifuged at 200000×g (50000 rpm in 70.1 Ti) for 20 min to obtain the PSDII pellet containing concentrated post synaptic densities. The PSDII pellet was resuspended in 100 ml 50 mM HEPES, pH 7.4, 2 mM EDTA plus protease inhibitors. The protein concentration of the fractions was measured using Bio-Rad Protein Assay and an aliquot of 7-10 mg of each fraction were dissolved in SDS sample buffer (20 mM Tris-HCl, 5% SDS, 17.4% glycerol, 57% Pyronin Y (Sigma), 20 mM DTT). Fractions were separated by reducing SDS-PAGE (4-16% Tris-glycine gels) and analyzed by Western blotting using Sortilin antibodies or SorCS2 antibodies. The localization of Sortilin and SorCS2 were compared to that of the presynaptic marker Synaptophysin and the postsynaptic density marker PSD-95. Lysates of HEK293 cells stably transfected with Sortilin or SorCS2 encoding plasmids were included as positive controls. The identity of the individual fractions is listed to the right.

FIG. 3: Impaired NMDA receptor-dependent LTD in Sortilin −/− and SorCS1 −/− mice. A, lack of LTD in sortilin −/− hippocampal CA1 synapses by the application of LFS (1 Hz, 15 min) to the Schaffer collaterals. In wt hippocampal CA1 synapses a LFS induces synaptic depression. B, rescue of NMDA receptor-dependent LTD in Sortilin −/− hippocampal CA1 synapses by cleavage-resistant proBDNF. Sortilin −/− hippocampal slices were incubated with 4 ng/ml purified, cleavage-resistant proBDNF for at least 1 h before recording, and present throughout the experiment as indicated. LFS (1 Hz, 15 min) was applied to the Schaffer collaterals. In Sortilin −/− hippocampal slices incubated with control vehicle the LTD was still impaired. C, a similar experiment showing rescue of NMDA receptor-dependent LTD in sortilin −/− hippocampal CA1 synapses by 40 ng/ml purified soluble Sortilin. D, a similar experiment showing lack of LTD in SorCS1 −/− hippocampal CA1 synapses. The hippocampal slices used in all experiments were from 3-weeks old mice. Error bars indicate standard error of mean (S.E.M.)

FIG. 4: Impaired NMDA receptor-dependent LTD in SorCS2 −/− mice. A, lack of LTD induced by LFS in SorCS2 −/− hippocampal CA1 synapses by the application of LFS (1 Hz, 15 min) to the schaffer collaterals. In wt hippocampal CA1 synapses a LFS induce synaptic depression. B, no rescue of NMDA receptor-dependent LTD in SorCS2 −/− hippocampal CA1 synapses by cleavage-resistant proBDNF. SorCS2 −/− hippocampal slices were incubated with 4 ng/ml purified, cleavage-resistant proBDNF for at least 1 h before recording, and present throughout the experiment as indicated. LFS (1 Hz, 15 min) was applied to the Schaffer collaterals. In SorCS2 −/− hippocampal slices incubated with control vehicle the LTD was still impaired. C, impaired NMDA receptor-dependent LTD in wt hippocampal CA1 synapses by the application of anti-SorCS2 IgG. In the control experiment with unspecific IgG, LFS induced synaptic depression in wt hippocampal CA1 synapses. LFS (1 Hz, 15 min) was applied to the Schaffer collaterals. Hippocampal slices were incubated with IgG for at least 90 min before recording, and present throughout the experiment as indicated. Error bars indicate S.E.M. D, model for the induction of synaptic plasticity adapted from (Lu, Pang et al. 2005) describing the role of proBDNF in the induction of long-term depression (LTD) through interaction with $p75^{NTR}$ and the role of mature BDNF in the induction of long-term potentiation (LTP) through interaction with TrkB.

FIG. 5: Impaired long-term potentiation in Sortilin −/− and SorCS2 −/− hippocampal CA1 synapses. A, two trains of HFS (100 Hz, 1 s) were applied to the Schaffer collaterals and the late-phase long-term potentiation is measured after 3 h. In the wt hippocampal CA1 synapses the efficacy of synaptic transmission have potentiated to about 150% of the baseline after 3 h. In the Sortilin −/− hippocampal CA1 synapses the late-phase of long-term potentiation has declined to the baseline level and no late-phase long-term potentiation is induced. B, a similar experiment showing partial early- and late-phase long-term potentiation in SorCS2 −/− hippocampal CA1 synapses. Two trains of HFS (100 Hz, 1 s) were applied to the Schaffer collaterals and the early- and late-phase long-term potentiation was measured after 30 min and 3 h, respectively. The early-phase of long-term potentiation is slightly reduced in the SorCS2 −/− mice compared to the wt mice. In the SorCS2 −/− hippocampal CA1 synapses the efficacy of synaptic transmission have potentiated to about 125% of the baseline after 3 h, compared to 150% for the wt hippocampal slices. Error bars indicate S.E.M. C, an experiment identical to that of B showing impaired early- and late-phase long-term potentiation in SorCS2 −/− hippocampal CA1 synapses.

FIG. 6: Physical interaction between SorCS2 and $p75^{NTR}$. A, HEK293 cells stably transfected with SorCS2 and $p75^{NTR}$ encoding vectors were crosslinked with DSP (Pierce) and subsequently lysed. The cell lysate was incubated with antibody against SorCS2 bound to Gammabind beads (GE Healthcare). The precitated complexes were eluted from the washed beads with SDS loading buffer. Western blot analysis revealed the presence of a SorCS2:$p75^{NTR}$ complex. The presence of $p75^{NTR}$ and IgG heavy is indicated. HEK293 cells stably transfected with a $p75^{NTR}$ encoding plasmid alone were used as negative control. B, surface plasmon resonance experiment (BIAcore) showing the direct interaction of soluble full-length extracellular domain of $p75^{NTR}$ (p75 ECD) with immobilized soluble SorCS2. The p75 ECD concentration used was 1 μM. The $K_d$ is estimated to approximately 10 nM.

Figure 7:
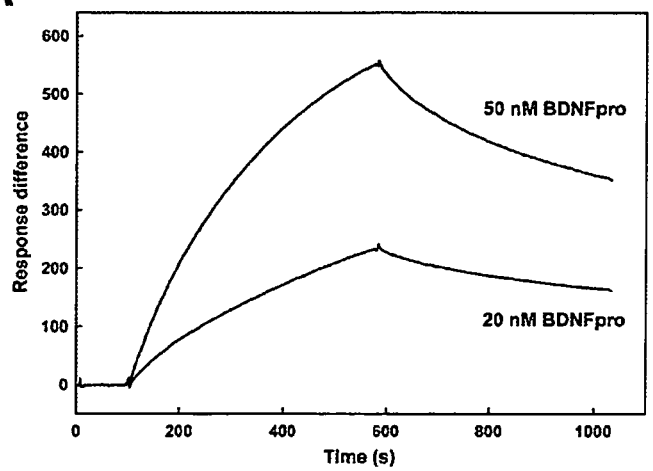
Figure 7:
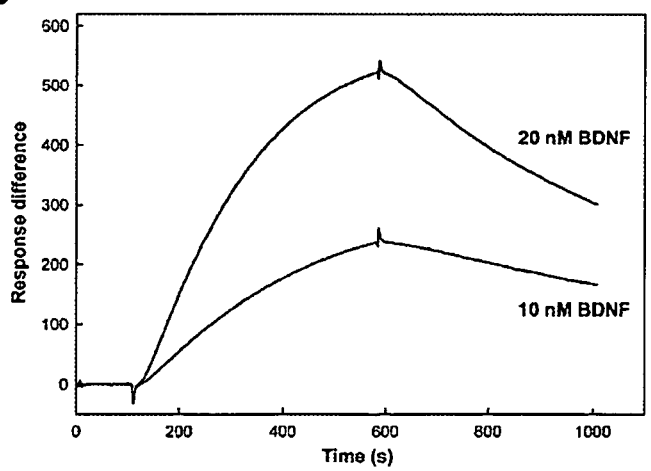
Figure 8:
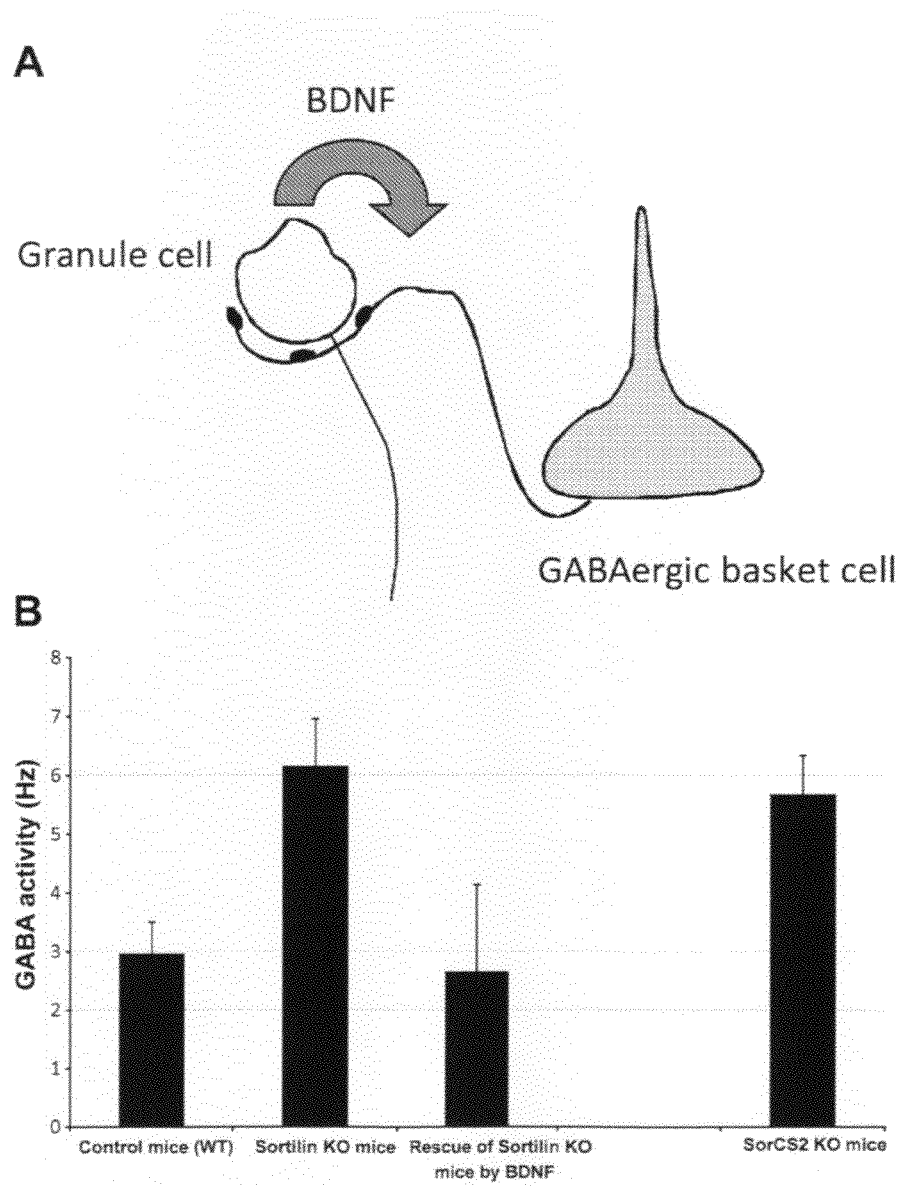

FIG. 7: The binding of BDNF propeptide and mature BDNF to SorCS2. A, BDNF propeptide binding to immobilized soluble SorCS2 analyzed by surface plasmon resonance (BIAcore). The BDNF propeptide concentrations used were 20 nM and 50 nM. The $K_d$ was estimated to 15 nM. B, mature BDNF binding to SorCS2. The mature BDNF concentrations used were 10 nM and 20 nM. The $K_d$ was estimated to 5 nM.

FIG. 8: Neuronal GABA activity is increased in Sortilin and SorCS2 −/− mice, and can be rescued by BDNF. A, model describing how dentate gyrus granule cells are under powerful inhibitory control by GABAergic basket cells. The basket cell excitability is in turn depressed by BDNF released from the granule cells (Holm et al. Submitted, 2008) B, the GABAergic activity was assessed by electrophysiological recordings from single neurons in an in vitro mouse brain slice preparation (P16-P20). In each experimental condition, the frequency of spontaneous inhibitory postsynaptic currents (sIPSCs) was measured in Hz. In control mice (wild-type, WT) the GABAergic activity was 2.96±0.53 Hz (n=33 cells). In Sortilin −/− (Sortilin KO) mice, this activity increased to 6.15±0.80 Hz (n=25 cells). In rescue experiments, exogenous BDNF (20 ng/ml) reversed the GABA activity of Sortilin KO mice back to WT levels, reaching 2.66±1.4 Hz (n=3 cells). For comparison, the GABAergic activity in SorCS2 −/− (SorCS2 KO) mice was 5.68±0.7 Hz (n=6), highlighting the importance of Vps10p proteins in these inhibitory cell functions. Error bars indicate S.E.M.

Figure 9:
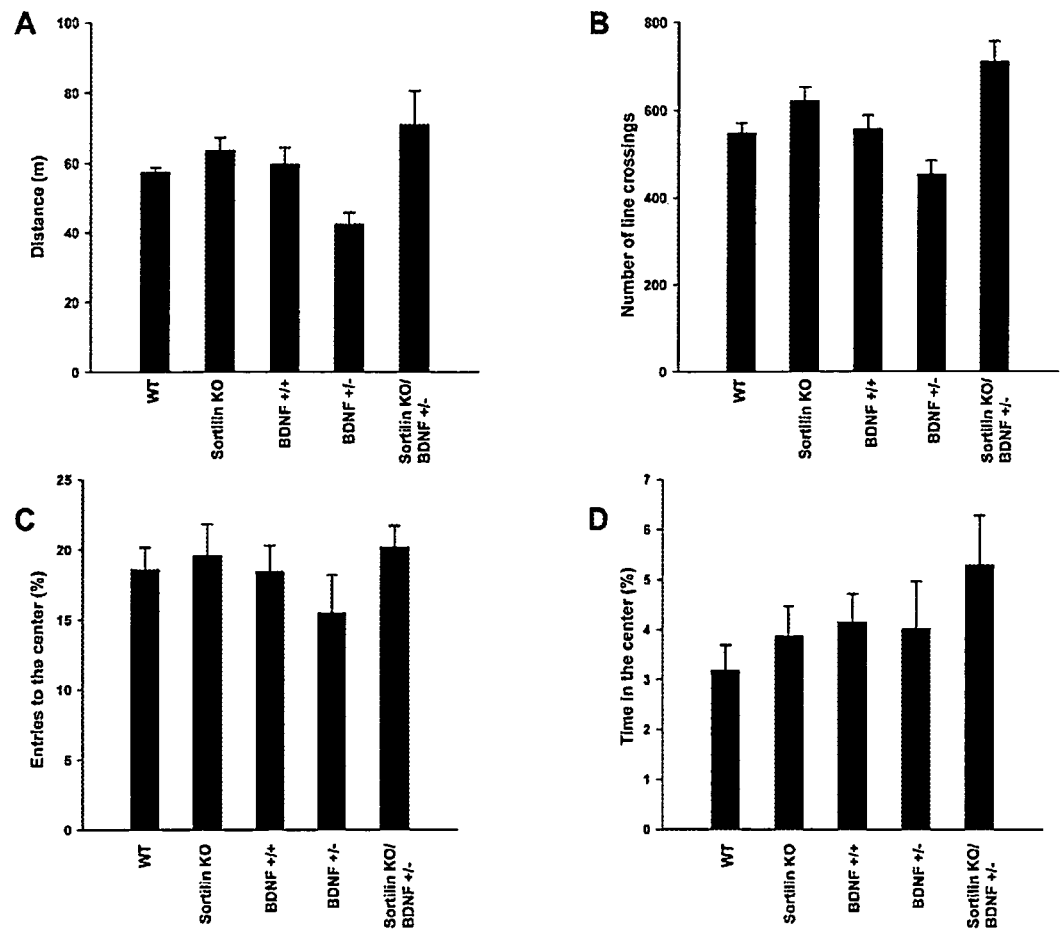
Figure 9:
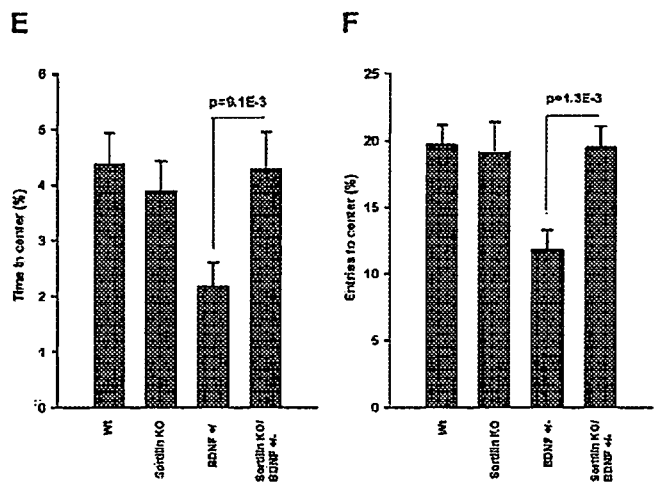

FIG. 9: Open field and elevated plus maze tests of three month old Sortilin −/− (Sortilin KO), BDNF +/+, BDNF +/−, and Sortilin KO/BDNF +/− mice. The open field test is frequently used as an experimental model for depressive, manic, and anxiety-related behavior. Treatment of mice with antidepressive or anxiolytic agents normally increase the distance traveled, the number of line crossings, and the number of entries and time spent in the center of the open field. Wild-type (WT) mice (n=9), Sortilin KO mice (n=12), BDNF +/+ (n=9) and BDNF +/− (n=5) littermates, and mice lacking both the Sortilin gene and one BDNF allele, Sortilin KO/BDNF +/−, (n=4) were analyzed in an open field consisting of a (40×40×35 cm) clear Plexiglas arena. The arena was set up in a dim room under a video camera connected to a computer under the control of the Any-maze tracking system. Mice were placed in the corner of the arena and their behavior was recorded over a 20 min session. The open field was divided into a center zone, an intermediate zone, and a peripheral zone. The number of entries and the time spent in the different zones was analyzed using the Any-Maze tracking software. A, the distance traveled during the course of the experiment. B, the total number of line crossings between the different zones. C, the percentage of entries into the center zone (center zone entries/peripheral zone entries*100). D, the percentage of time spent in the center. Error bars indicate S.E.M. E, Open field test of three month old Sortilin −/− (Sortilin KO), BDNF +/+, BDNF +/−, and Sortilin KO/BDNF +/− mice. The open field test is frequently used as an experimental model for depressive, manic, and anxiety-related behavior. Treatment of mice with antidepressive or anxiolytic agents normally increase time spent in the center of the open field. Sortilin KO mice (n=10), BDNF +/+ (n=9), BDNF +/− (n=11), and mice lacking both the Sortilin gene and one BDNF allele, Sortilin KO/BDNF +/−, (n=9) (all mice are littermates and around three months old) were analyzed in an open field consisting of a (40×40×35 cm) clear Plexiglas arena. The arena was set up in a dim room under a video camera connected to a computer under the control of the Any-maze tracking system. Mice were placed in the corner of the arena and their behavior was recorded over a 20 min session. The open field was divided into a center zone, an intermediate zone, and a peripheral zone. The number of entries and the time spent in the different zones was analyzed using the Any-Maze tracking software. E, the distance traveled during the course of the experiment. Error bars indicate S.E.M. F, the mice were further tested in an elevated plus maze, a more challenging experimental model for depressive, manic, and anxiety-related behavior. Treatment of mice with antidepressive or anxiolytic agents normally increases the number of entries and time spent in the open arms. The elevated plus maze were raised 40 cm above the floor, and consisting of two opposite enclosed arms with 15 cm high opaque walls and two opposite open arms of the same size (35×5 cm). The elevated plus maze was set up in a dim lit room under a video camera connected to a computer under the control of the Any-maze tracking system. Testing sessions of 10 min were carried out for each mouse and measured the number of entries and the time spent in the open arms. F, the percentage of entries into the open arms (open arm entries/closed arm entries*100).

Figure 10:
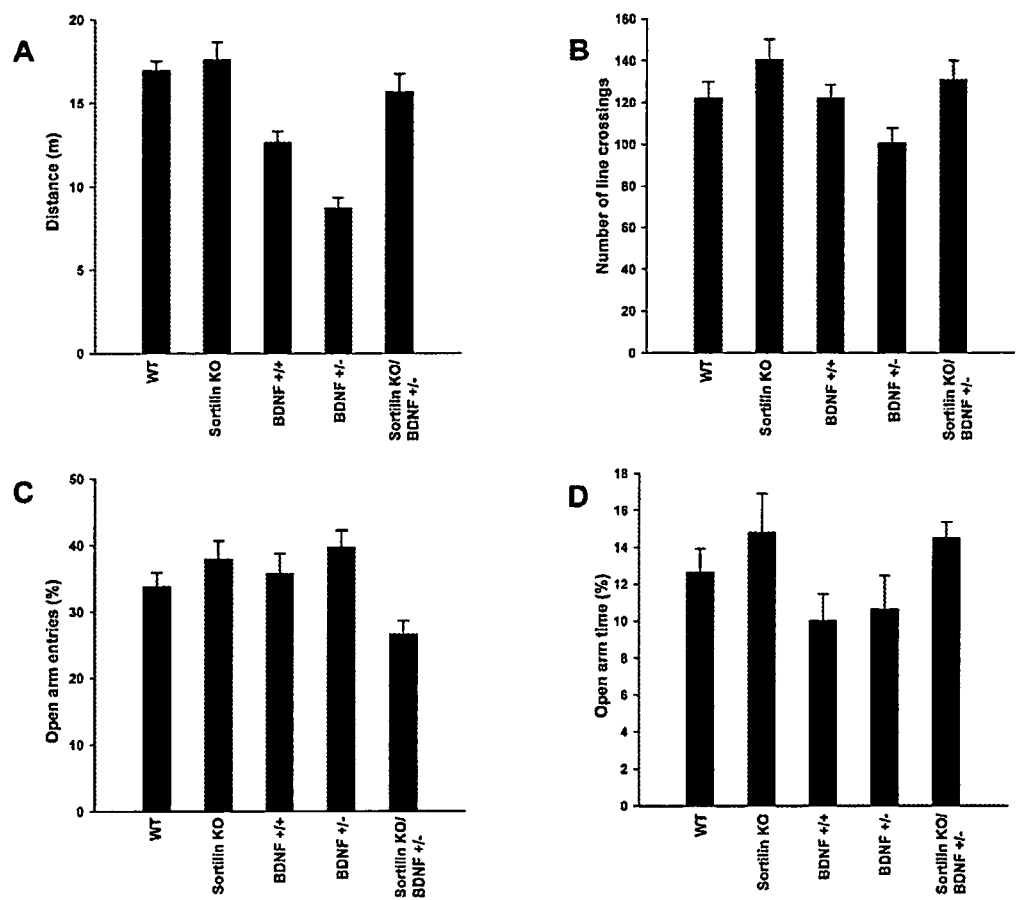
Figure 10:
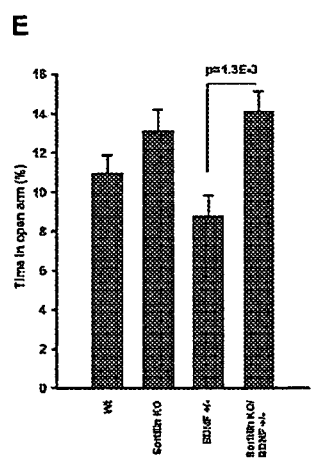

FIG. 10: The behavior three month old Sortilin −/− (Sortilin KO), BDNF +/+, BDNF +/−, and Sortilin KO/BDNF +/− mice in an elevated plus maze. The elevated plus maze is used as a more challenging experimental model for depressive, manic, and anxiety-related behavior. Treatment of mice with antidepressive or anxiolytic agents normally increase the distance traveled, the number of line crossings, and the number of entries and time spent in the open arms. The behavior of wild-type (WT) mice (n=9), Sortilin KO mice (n=12), BDNF +/+ (n=9) and BDNF +/− (n=5) littermates, and mice lacking both the Sortilin alleles and one BDNF allele, Sortilin KO/BDNF +/−, (n=4) were tested in an elevated plus maze raised 40 cm above the floor, and consisting of two opposite enclosed arms with 15 cm high opaque walls and two opposite open arms of the same size (35×5 cm). The elevated plus maze was set up in a dim lit room under a video camera connected to a computer under the control of the Any-maze tracking system. Testing sessions of 10 min were carried out for each mouse and measured the number of entries and the time spent in the open arms. A, the distance traveled during the course of the experiment. B, the total number of crossings between the open and closed arms. C, the percentage of entries into the open arms (open arm entries/closed arm entries*100). D, the percentage of time spent in the open arms. Error bars indicate S.E.M. E, the percentage of time spent in the open arms. Error bars indicate S.E.M.

Figure 11:
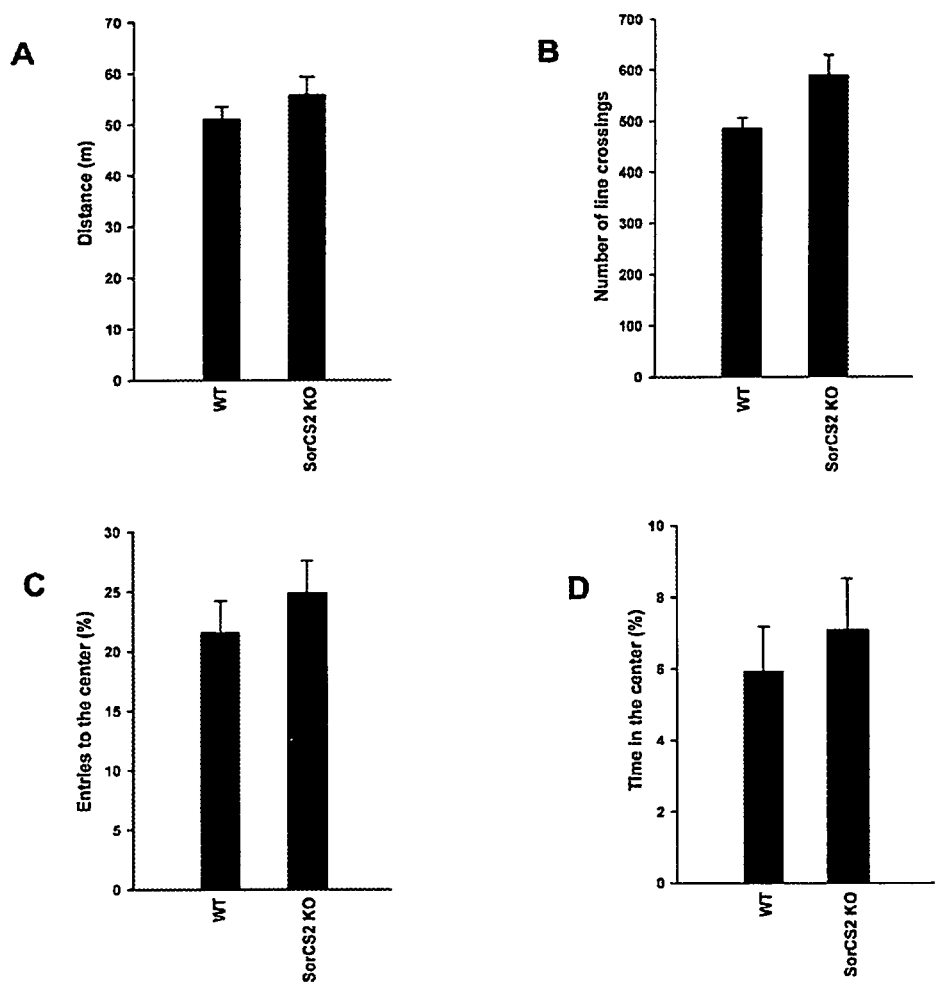

FIG. 11: Open field test of eight month old SorCS2 −/− (SorCS2 KO) and WT mice. Eight-month-old wild-type (WT) mice (n=6) and SorCS2 KO mice (n=4) were analyzed in the open field test as described in the FIG. 9 legend. A, the distance traveled during the course of the experiment. B, the total number of line crossings between the different zones. C, the percentage of entries into the center zone (center zone entries/peripheral zone entries*100). D, the percentage of time spent in the center. Error bars indicate S.E.M.

Figure 12:
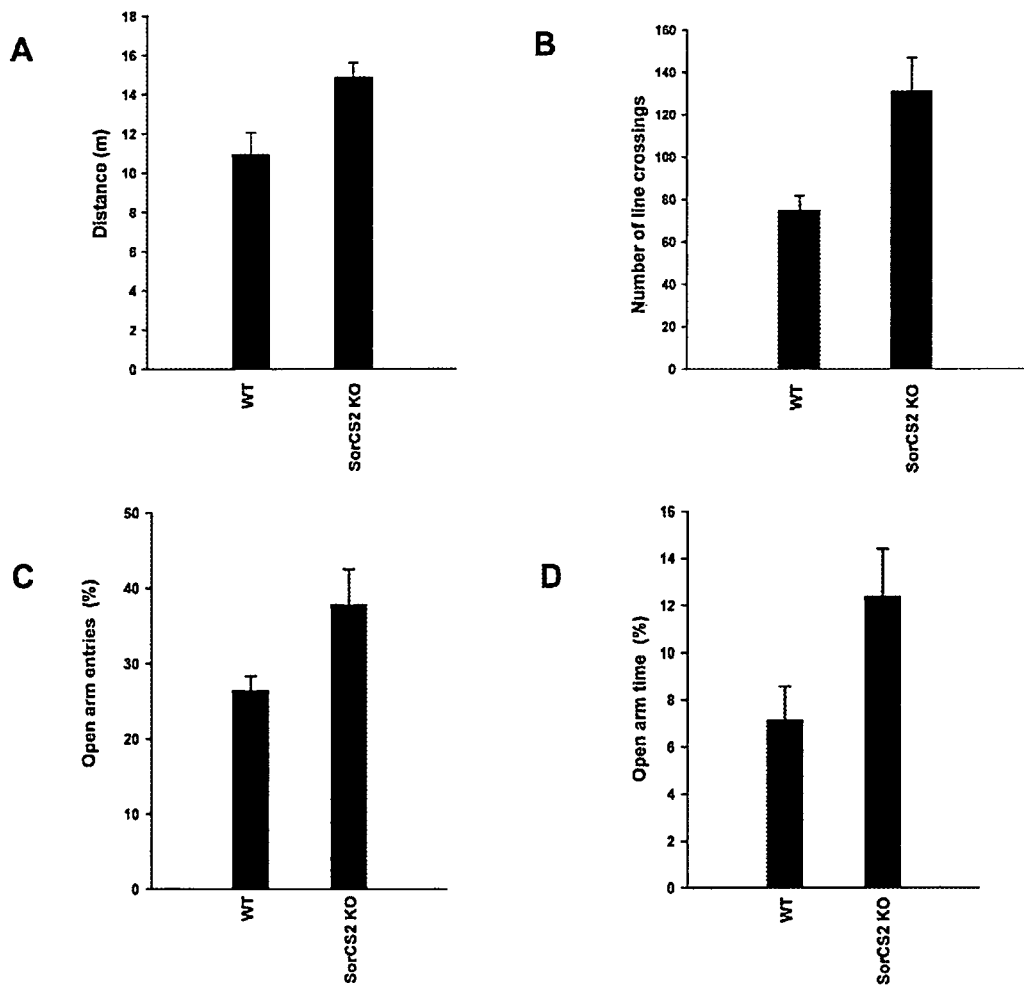

FIG. 12: The behavior SorCS2 −/− (SorCS2 KO) and WT mice in an elevated plus maze. Eight-month-old wild-type (WT) mice (n=6) and SorCS2 KO mice (n=4) were analyzed in the elevated plus maze as described in the FIG. 10 legend. A, the distance traveled during the course of the experiment. B, the total number of crossings between the open and closed arms. C, the percentage of entries into the open arms (open arm entries/closed arm entries*100). D, the percentage of time spent in the open arms. Error bars indicate S.E.M.

Figure 13:
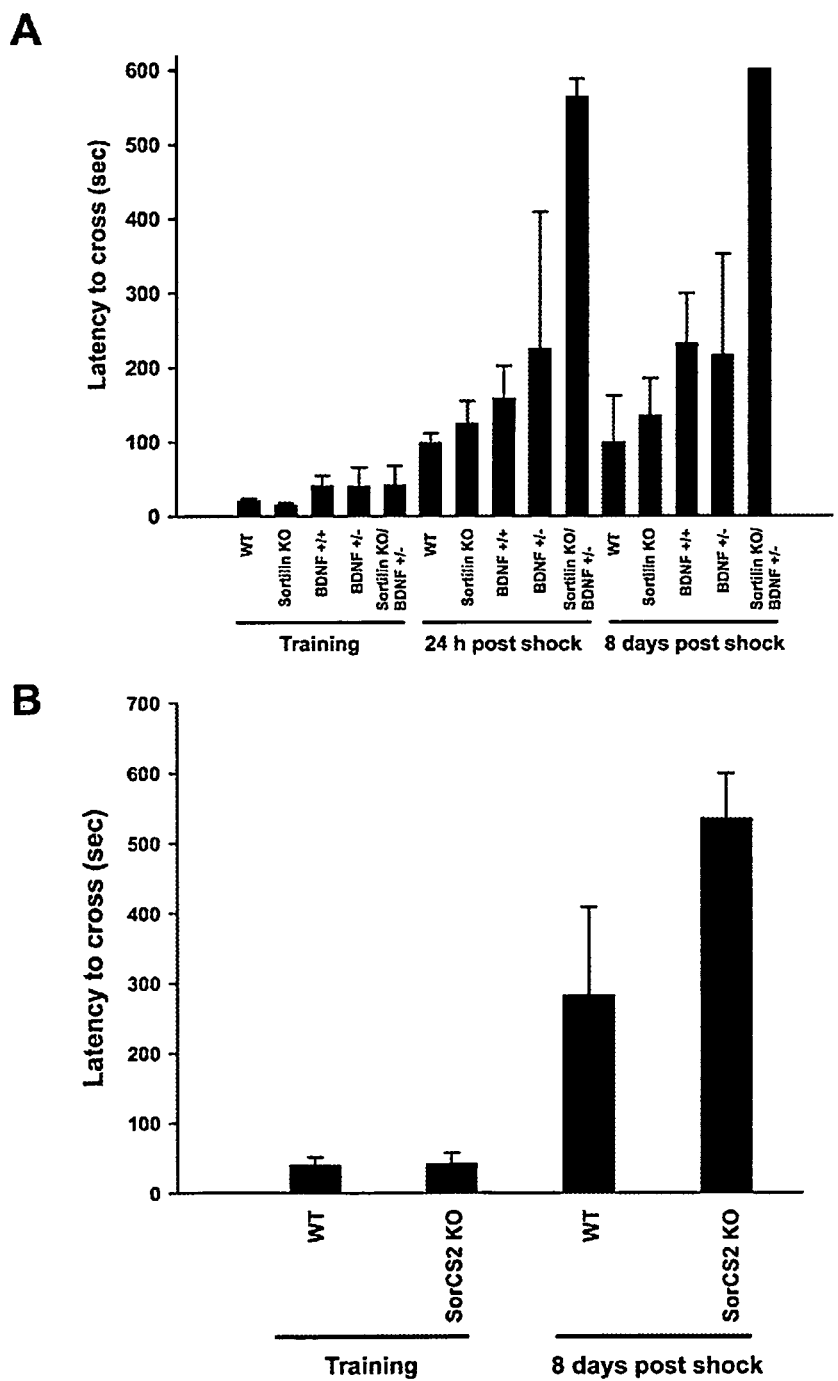
Figure 13:
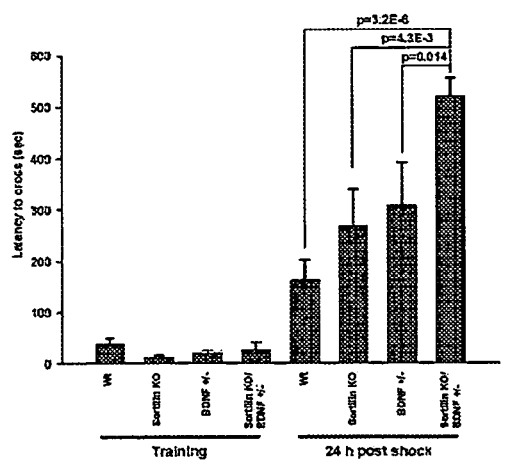

FIG. 13: Altered memory function in Vps10p-domain receptor transgenic mice. A, three-month-old wild-type (WT) mice (n=9), Sortilin −/− (Sortilin KO) mice (n=12), BDNF +/+ (n=9) and BDNF +/− (n=4) littermates, and mice lacking both the Sortilin alleles and one BDNF allele, Sortilin KO/BDNF +/−, (n=4) tested in a passive avoidance experiment (Gemini Avoidance System). The experimental set up takes advantage of the natural preference of mice for the dark, and consists of a brightly lit room and a dark room separated by a guillotine door. On the training day, the mouse is placed in the bright room. When entering the dark room, the door closes and the mouse receives an electric shock (0.8 mA for 1 sec). 24 hours later, the mouse is returned to the bright room and the latency to enter the dark room indicates memory of the shock. B, eight-month-old wild-type (WT) mice (n=6) and SorCS2 −/− (SorCS2 KO) mice (n=4) tested in a passive avoidance experiment. Error bars indicate S.E.M. C, three-month-old, Sortilin −/− (Sortilin KO) mice (n=9), BDNF +/+ (n=10), BDNF +/− (n=7), and mice lacking both the Sortilin alleles and one BDNF allele, Sortilin KO/BDNF +/−, (n=8) (all mice are littermates) tested in a passive avoidance experiment (Gemini Avoidance System). The experimental set up takes advantage of the natural preference of mice for the dark, and consists of a brightly lit room and a dark room separated by a guillotine door. On the training day, the mouse is placed in the bright room. When entering the dark room, the door closes and the mouse receives an electric shock (0.8 mA for 1 sec). 24 hours later, the mouse is returned to the bright room and the latency to enter the dark room indicates memory of the shock.

FIG. 14: Depressive behavior of SorCS2 −/− (SorCS2 KO) mice. The wild-type (WT) mice (n=6) and SorCS2 KO mice (n=4) previously tested in a test battery of the open field test, the elevated plus maze, and the passive avoidance test, were finally tested in a forced swim test, a well-described test for depressive behavior in rodents. The forced swim test used was essentially similar to that described elsewhere (Porsolt, Le Pichon et al. 1977). Mice were dropped individually into glass cylinders (height: 30 cm, diameter: 15 cm) containing 20 cm water, maintained at 23-25° C., and remained there for 6 min while their movements were recorded using a digital video camera. A mouse was judged to be immobile when it floated in an upright position and made only small movements to keep its head above water. The time of immobility was scored during the last 4 min of the 6 min testing period, after 2 min habituation. Error bars indicate S.E.M.

Figure 15:
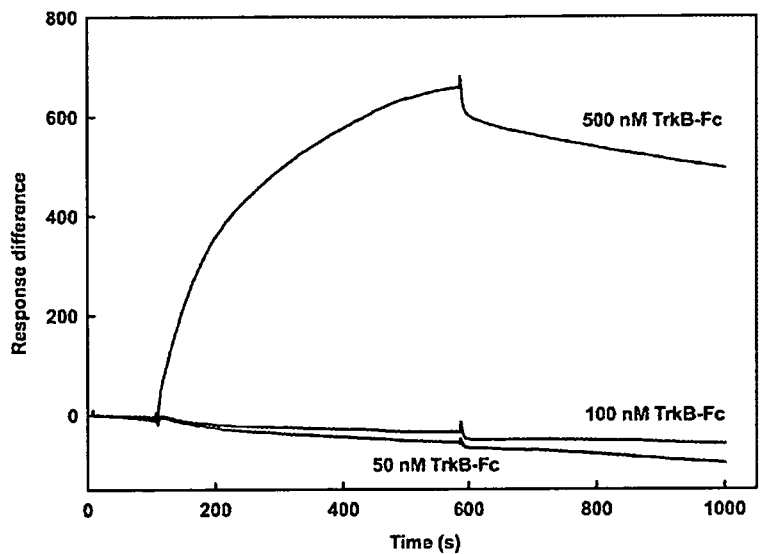
Figure 15:
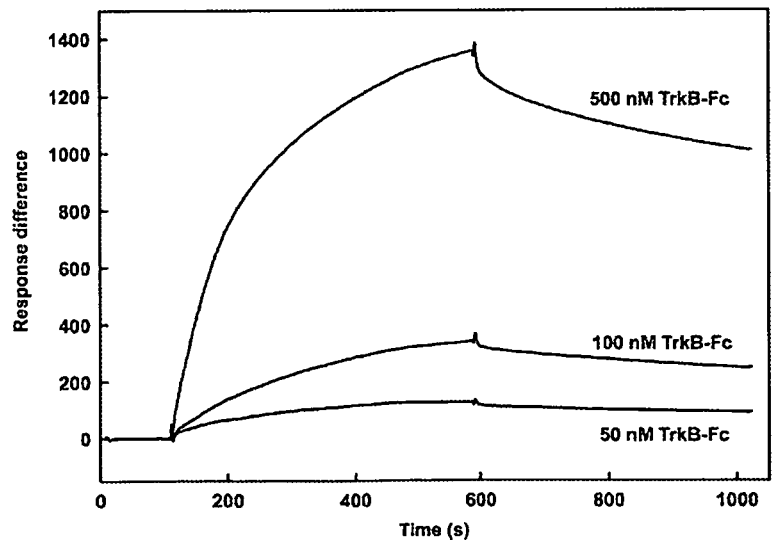
Figure 15:
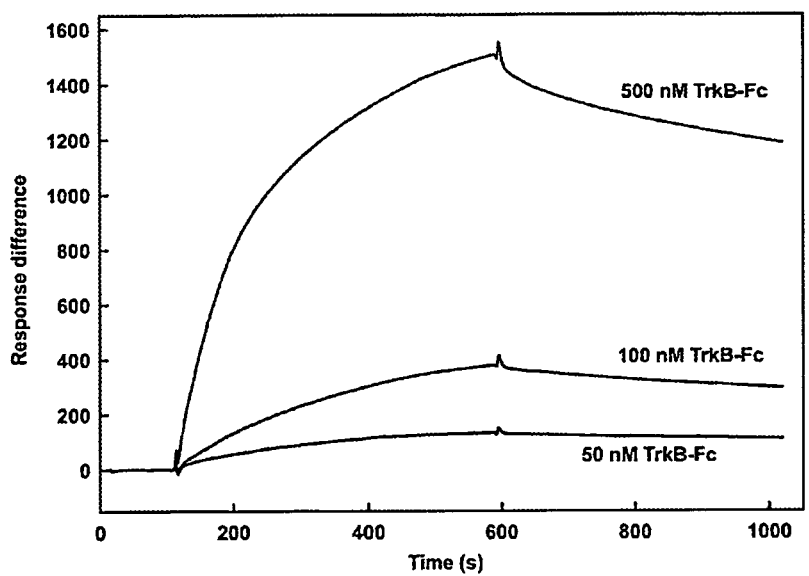

FIG. 15: The binding of the extracellular domain of TrkB to immobilized Sortilin, SorCS1, and SorCS2. A, TrkB-Fc chimera (R&D Systems) binding to immobilized soluble Sortilin analyzed by surface plasmon resonance (BIAcore). The TrkB-Fc chimera concentrations used were 500 nM, 100 nM, and 50 nM. The $K_d$ was estimated to 29 nM. B, a similar experiment showing TrkB-Fc chimera binding to immobilized soluble SorCS1. The $K_d$ was estimated to 9 nM. C, a similar experiment showing TrkB-Fc chimera binding to immobilized soluble SorCS2. The $K_d$ was estimated to 17 nM. No binding of the Fc fragment alone was observed to any of the Vps10p domain receptors (data not shown).

FIG. 16: SorCS2 −/− mice—open field test. A, Distance travelled during in an open field test as described above of 3-12 month old wt (n=6) and SorCS1 KO. Error bars indicate S.E.M.

FIG. 17: Sortilin −/− mice—elevated plus maze—passive avoidance. A, elevated plus maze test of 2-3 month old wt (n=14) and Sortilin KO (n=19) showing percentage of time spent in open arms and B, open arm entries (%). C, passive avoidance experiment of 2-3 month old wt (n=8) and Sortilin KO (n=13) as described above. Error bars indicate S.E.M.

FIG. 18: Sortilin −/−, BDNF +/−, Sortilin −/−/BDNF +/−, SorCS2 −/− mice—falls of an elevated plus maze. Falls of an elevated plus maze can be interpreted as a behavioural analogue in mice of activity-deficiency and hyperactivity disorder. Falls of the elevated plus maze were scored for the indicated genotypes.

Figure 19:
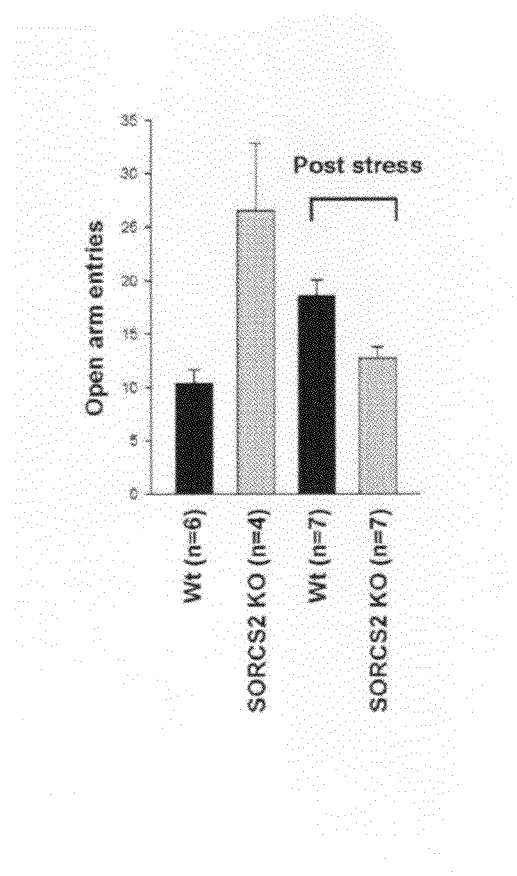

FIG. 19: SorCS2 −/− mice—elevated plus maze. Open arm entries of wt and SorCS2 KO mice were tested for 10 min in an elevated plus maze in a brightly lit room with or without being placed on an elevated platform (1 m) in transparent Plexiglas for 30 min prior to the experiment. This treatment has previously been shown accompany the facilitation of LTD in the hippocampus (Xu, L et al. Nature (387) 1997).

Figure 20:
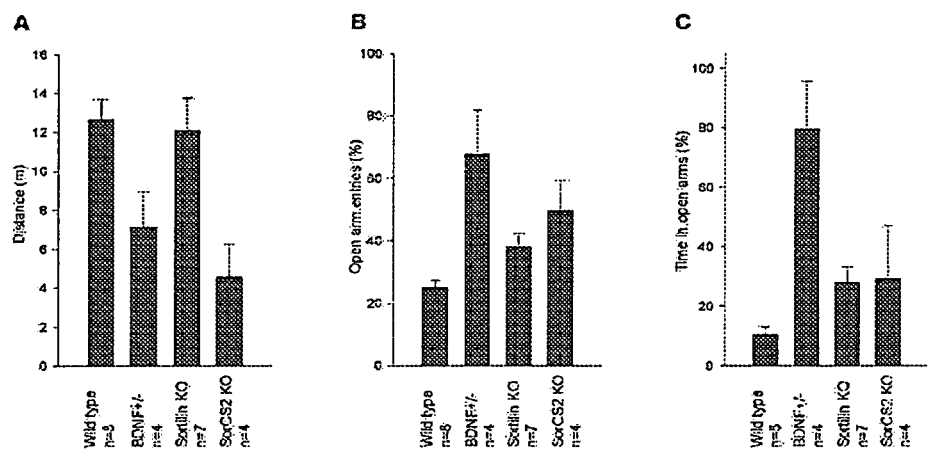

FIG. 20: BDNF +/−, Sortilin −/−, SorCS2 −/− mice—elevated plus maze. The behaviour of the indicated genotypes in an elevated plus maze after having received a foot shock (1 s, 0.8 mA) 24 h before. A, distance travelled. B, open arm entries (%). C, percentage of time spent in the open arms.

FIG. 21: Blockade of LTD in wild type mice by GST-Sortilin propeptide. LFS (1 Hz, 15 min) was applied to the Schaffer collaterals. Hippocampal slices were incubated in GST-Sortilin propeptide or control GST during recovery and were also present throughout the experiments as indicated.

Figure 22:
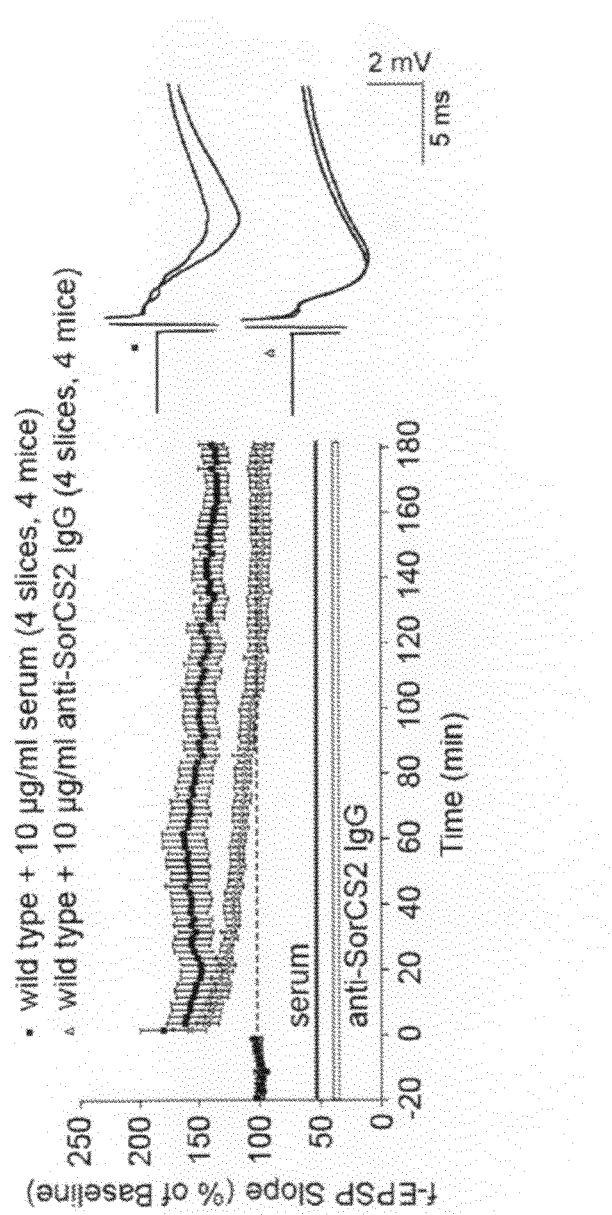

FIG. 22: Blockade of LTP in wild type mice by anti-SorCS2 IgG. Two trains of HFS (100 Hz, 1 s) were applied to the Schaeffer collaterals. Hippocampal slices were incubated in anti-SorCS2 IgG or control serum during recovery and were also present throughout the experiments as indicated. Sample traces are shown at baseline and 180 min after tetanus.

Figure 23:
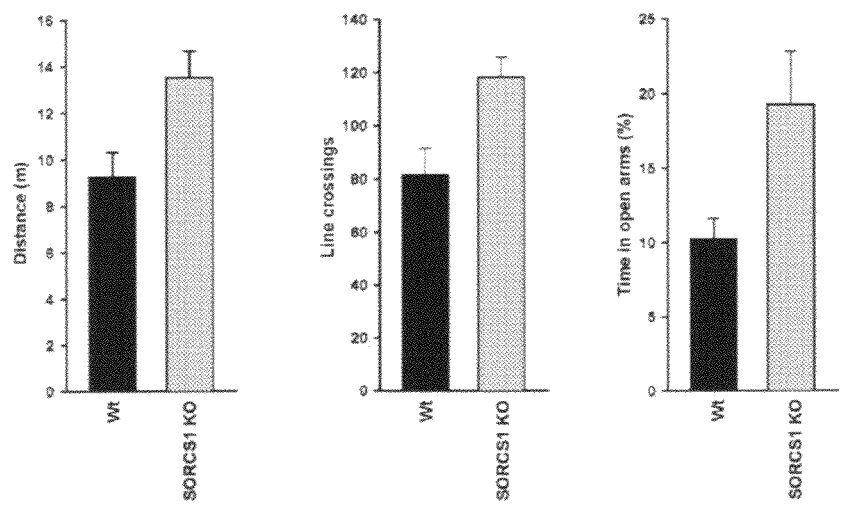

FIG. 23: SorCS1 −/− mice—elevated plus maze. 3 month old Wt (n=6) and SorCS1 KO (n=7) mice were tested in an elevated plus maze. The maze was raised 40 cm above the floor, and consisting of two opposite enclosed arms with 15 cm high opaque walls and two opposite open arms of the same size (35×5 cm). The elevated plus maze was set up in a dim lit room under a video camera connected to a computer under the control of the Any-maze tracking system. Testing sessions of 10 min were carried out for each mouse and measured (A) the distance travelled, (B) the number of line crossings between the open and closed arms, and (C) the percentage of time spent in the open arms. Error bars indicate S.E.M.

EXAMPLES

Example 1

Demonstration of a SorCS2:p75$^{NTR}$ Complex

HEK293 cells stably transfected with plasmids encoding SorCS2 and p75$^{NTR}$ were crosslinked with DSP (Pierce) and subsequently lysed. The cell lysate was incubated with antibody against SorCS2 bound to Gammabind beads (GE Healthcare). Precipitated complexes were eluted from the washed beads with SDS loading buffer. Western blot analysis revealed the presence of a SorCS2: p75$^{NTR}$ complex (FIG. 6A). The direct interaction of the extracellular domains of SorCS2 and p75$^{NTR}$ was also demonstrated using surface plasmon resonance (Biacore, Sweden) using CaHBS as standard running buffer (10 mM HEPES, pH 7.4, 140 mM NaCl, 2 mM CaCl2, 1 mM EGTA, 0.005% Tween-20). A biosensor chip from Biacore (CM5, cat. no. BR-1000-14) was activated using the NHS/EDC method as described by the supplier followed by coating with SorCS2 (FIG. 6B).

Example 2

Demonstration of a SorCS2:TrkB Complex

The direct interaction of the extracellular domains of SorCS2 and TrkB was demonstrated using surface plasmon resonance (Biacore, Sweden) using CaHBS as standard running buffer (10 mM HEPES, pH 7.4, 140 mM NaCl, 2 mM CaCl2, 1 mM EGTA, 0.005% Tween-20). A biosensor chip from Biacore (CM5, cat. no. BR-1000-14) was activated using the NHS/EDC method as described by the supplier followed by coating with SorCS2 (FIG. 15C). The SorCS2: TrkB complex is also demonstrated by co-immunoprecipitation. Cells expressing SorCS2 and TrkB, e.g. following transfection with plasmids encoding both receptors, respectively, are crosslinked with DSP (Pierce) and subsequently lysed. The cell lysate is incubated with antibody against SorCS2 bound to Gammabind beads (GE Healthcare). Precitated complexes are eluted from the washed beads with SDS loading buffer. Western blot analysis reveals the presence of a SorCS2:TrkB complex.

Example 3

Demonstration of the Interaction of SorCS2 with the BDNF Propeptide and with Mature BDNF The direct interaction of the extracellular domain of SorCS2 and with the BDNF propeptide and with mature BDNF was demonstrated using surface plasmon resonance (Biacore, Sweden) using CaHBS as standard running buffer (10 mM HEPES, pH 7.4, 140 mM NaCl, 2 mM CaCl2, 1 mM EGTA, 0.005% Tween-20). A biosensor chip from Biacore (CM5, cat. no. BR-1000-14) was activated using the NHS/EDC method as described by the supplier followed by coating with SorCS2 (FIG. 7).

Example 4

A Cell Based Screening Method for Identifying Receptor Antagonists/Agonists that Modulates the Signaling by Complexes Comprising SorCS2 and $p75^{NTR}$ or TrkB Determination of binding, internalization or signaling by members of the Vps10p domain receptor family can be performed in cellular systems. Cells expressing SorCS2, $p75^{NTR}$ and TrkB following e.g. transfection with plasmids encoding all three receptors, respectively, are incubated with a candidate agent (inhibitor/antagonist) compound. Said agent can e.g. represent an antibody against either one of the receptors, SorCS2 and TrkB binding ligands such as proBDNF, BDNF or, fragments of the respective receptors. After incubation, the cells are washed, protein complexes crosslinked with DSP (Pierce) and subsequently lysed. The cell lysate is incubated with antibody against SorCS2 covalently bound to sepharose beads. Precipitated complexes are eluted (eluate 1) from the washed beads (acidic buffer and subsequent neutralization) and subjected to another round of immunoprecipitation using anti-TrkB antibody and precipitated proteins eluted (eluate 2) with SDS loading buffer. Eluate 1 is composed of precipitated SorCS2 alone and/or SorCS2:TrkB, SorCS2:$p75^{NTR}$ and SorCS2:TrkB:$p75^{NTR}$ complexes whereas eluate 2 only contains SorCS2:TrkB and/or SorCS2:TrkB:$p75^{NTR}$ complexes. Western blot analysis of TrkB and $p75^{NTR}$ in eluate 1 reveals whether candidate compounds are able to inhibit SorCS2:TrkB and SorCS2:$p75^{NTR}$ complex formation, respectively. Western blot analysis of $p75^{NTR}$ in eluate 2 reveals whether candidate compounds are able to inhibit formation of the ternary SorCS2:TrkB:$p75^{NTR}$ complex.

Example 5

An In Vitro Assay for Identifying Agents Disrupting the Interaction of $p75^{NTR}$ and/or TrkB with SorCS2

Determination of direct binding of a ligand such as a small organic molecule, a peptide or a soluble receptor including but not limited to SorCS2, $p75^{NTR}$ and TrkB, to immobilized protein can be performed by e.g. surface plasmon resonance analysis (Biacore, Sweden) using CaHBS as standard running buffer (10 mM HEPES, pH 7.4, 140 mM NaCl, 2 mM CaCl2, 1 mM EGTA, and 0.005% Tween-20). A biosensor chip from Biacore (CM5, cat. no. BR-1000-14) is activated using the NHS/EDC method as described by supplier followed by coating with Sortilin or SorCS2. Several different approaches can be applied: Candidate agents can be identified by comparing the binding signal (response units) to a chip immobilized with one of the receptors and comparing this signal to an empty flow cell. In another approach, inhibition of an established ligand can be monitored in the absence or presence of putative inhibitors. The difference in the signal depicts the inhibitory potential of the antagonist. The data collected are analysed by fitting of sensorgrams for affinity estimations and inhibitory potential using the Biaevaluation version 3.1 program. The surface Plasmon resonance assay can easily be transform into other assays in which the Vps10p-domain receptor, the ligand or the putative inhibitor is immobilized on a solid phase. For instance, receptors can be immobilized in e.g. Maxisorp microtiter wells from Nunc (cat. no. 439454) by incubation for 16 h at 4° C. in 50 mM NaHCO₃, pH 9.6. After blocking using 5% bovine serum albumin (Sigma, cat. no. A9647) for 2 h at room temperature, the wells are washed three times with MB buffer (10 mM HEPES, pH 7.4, 140 mM NaCl, 2 20 mM $CaCl_2$, and 1 mM $MgCl_2$) before incubation with a labelled ligand (e.g. iodinated) in the absence or presence of a various concentrations of a candidate inhibitor. Following incubation (e.g. overnight at 4° C.) and washing with MB buffer, bound radioactivity is released by adding 10% SDS. Nonspecific binding of tracer to wells coated only with bovine serum albumin is determined and subtracted from the values determined in the binding experiments. The binding data point can be fitted to binding equations using the Prism software from GraphPad, version 4. Likewise, the antagonist can be labelled and binding to the immobilized receptor directly measured. In yet another setup, the receptor, ligand or antagonist can be immobilized on scintillation beads and binding measured in a scintillation proximity assay in which the receptor-binding molecule has been labelled using radioactivity.

Example 6

An In Vitro Assay for Identifying Agents Disrupting the Interaction of proBDNF with Sortilin or SorCS2

Determination of direct binding of a ligand such as a small organic molecule, a peptide or a soluble protein to immobilized protein can be performed by e.g. surface plasmon resonance analysis (Biacore, Sweden) using CaHBS as standard running buffer (10 mM HEPES, pH 7.4, 140 mM NaCl, 2 mM CaCl2, 1 mM EGTA, and 0.005% Tween-20). A biosensor chip from Biacore (CM5, cat. no. BR-1000-14) is activated using the NHS/EDC method as described by supplier followed by coating with Sortilin or SorCS2. Several different approaches can be applied: Candidate agents can be identified by comparing the binding signal (response units) to a chip immobilized with one of the receptors and comparing this signal to an empty flow cell. In another approach, inhibition of an established ligand can be monitored in the absence or presence of putative inhibitors. The difference in the signal depicts the inhibitory potential of the antagonist. The data collected are analysed by fitting of sensorgrams for affinity estimations and inhibitory potential using the Biaevaluation version 3.1 program. The surface Plasmon resonance assay can easily be transform into other assays in which the Vps10p-domain receptor, the ligand or the putative inhibitor is immobilized on a solid phase. For instance, receptors can be immobilized in e.g. Maxisorp microtiter wells from Nunc (cat. no. 439454) by incubation for 16 h at 4° C. in 50 mM NaHCO$_3$, pH 9.6. After blocking using 5% bovine serum albumin (Sigma, cat. no. A9647) for 2 h at room temperature, the wells are washed three times with MB buffer (10 mM HEPES, pH 7.4, 140 mM NaCl, 2 20 mM CaCl$_2$, and 1 mM MgCl$_2$) before incubation with a labelled ligand (e.g. iodinated) in the absence or presence of a various concentrations of a candidate inhibitor. Following incubation (e.g. overnight at 4° C.) and washing with MB buffer, bound radioactivity is released by adding 10% SDS. Nonspecific binding of tracer to wells coated only with bovine serum albumin is determined and subtracted from the values determined in the binding experiments. The binding data point can be fitted to binding equations using the Prism software from GraphPad, version 4. Likewise, the antagonist can be labelled and binding to the immobilized receptor directly measured. In yet another setup, the receptor, ligand or antagonist can be immobilized on scintillation beads and binding measured in a scintillation proximity assay in which the receptor-binding molecule has been labelled using radioactivity.

Example 7

An In Vitro Assay for Identifying Agents Disrupting the Interaction of proBDNF and/or BDNF with SorCS2

Determination of direct binding of a ligand such as a small organic molecule, a peptide or a soluble protein to immobilized protein can be performed by e.g. surface plasmon resonance analysis (Biacore, Sweden) using CaHBS as standard running buffer (10 mM HEPES, pH 7.4, 140 mM NaCl, 2 mM CaCl2, 1 mM EGTA, and 0.005% Tween-20). A biosensor chip from Biacore (CM5, cat. no. BR-1000-14) is activated using the NHS/EDC method as described by supplier followed by coating with SorCS2. Several different approaches can be applied: Candidate agents can be identified by comparing the binding signal (response units) to a chip immobilized with one of the receptors and comparing this signal to an empty flow cell. In another approach, inhibition of an established ligand can be monitered in the absence or presence of putative inhibitors. The difference in the signal depicts the inhibitory potential of the antagonist. The data collected are analysed by fitting of sensorgrams for affinity estimations and inhibitory potential using the Biaevaluation version 3.1 program. The surface Plasmon resonance assay can easily be transform into other assays in which the Vps10p-domain receptor, the ligand or the putative inhibitor is immobilized on a solid phase. For instance, receptors can be immobilized in e.g. Maxisorp microtiter wells from Nunc (cat. no. 439454) by incubation for 16 h at 4° C. in 50 mM NaHCO$_3$, pH 9.6. After blocking using 5% bovine serum albumin (Sigma, cat. no. A9647) for 2 h at room temperature, the wells are washed three times with MB buffer (10 mM HEPES, pH 7.4, 140 mM NaCl, 2 20 mM CaCl$_2$, and 1 mM MgCl$_2$) before incubation with a labelled ligand (e.g. iodinated) in the absence or presence of a various concentrations of a candidate inhibitor. Following incubation (e.g. overnight at 4° C.) and washing with MB buffer, bound radioactivity is released by adding 10% SDS. Nonspecific binding of tracer to wells coated only with bovine serum albumin is determined and subtracted from the values determined in the binding experiments. The binding data point can be fitted to binding equations using the Prism software from GraphPad, version 4. Likewise, the antagonist can be labelled and binding to the immobilized receptor directly measured. In yet another setup, the receptor, ligand or antagonist can be immobilized on scintillation beads and binding measured in a scintillation proximity assay in which the receptor-binding molecule has been labelled using radioactivity. These approaches can be used to screen for ligands that inhibit the binding proBDNF but not mature BDNF to SorCS2. Similarly, these approaches can be used to screen for other ligands that inhibit the binding of mature BDNF but not proBDNF to SorCS2.

Example 8

A Cell Based Screening Method for Identifying Agents Capable of Inhibiting a Vps10p-Domain Receptor An antagonist directed against an entity of the Vps10p-domain:p75$^{NTR}$:TrkB receptor complex may act as an inhibitor of the entire complex. Accordingly it is relevant to screen for agents capable of binding to e.g. the Vps10p-domain receptor entity. Such a method is described in the present example. Determination of binding, internalization or signalling by members of the Vps10pdomain receptor family can be performed in cellular systems. Cells expressing one of the receptors, either endogenously or following e.g. transfection with a plasmid containing the cDNA of the receptor, are incubated with a radio-labeled ligand, in the absence and the presence respectively, of a candidate inhibitor/antagonist compound. After incubation, the cells are washed to remove unspecific binding and subsequently harvested. The degree of binding of the candidate antagonist/linhibitor to the receptor is determined by using a conventional radioligand assay well known to those skilled in the art. See e.g. Bylund and Toews (1993) Am J. Physiol. 265(5 Pt 1):L421-9 entitled "Radioligand binding methods: practical guide and tips". Likewise, endocytosis/internalization may be determined as described in Nykjaer et al (1992) FEBS 300:13- and Nielsen et al (2001) EMBO J., 20:2180-.

Example 9

Electrophysiological Characterization of Hippocampal Synaptic Plasticity Using SorCS2-Deficient Mice or Polyclonal Anti-SorCS2 IgG SorCS2 −/− mice were backcrossed onto a C57BL/6 background for more than ten generations and wild type C57BL/6 mice were used as control. We prepared trans-verse hippocampal slices (400 µm) from wt and age-matched transgenic mice that were between P17 and P22. We maintained slices in a storage chamber bubbled with 95% O$_2$ and 5% CO$_2$. After a recovery period of at least two h, the slices were moved to an interface chamber exposed to a humidified atmosphere of 95% O$_2$ and 5% CO$_2$ and we recorded field Exitatory Post-Synaptic Potentials (f-EPSP) using an Axoclamp-2B amplifier (Axon Instruments) with an artificial cerebral spinal fluid (ACSF; in mM: 126 NaCl, 2.5 KCl, 1.25 NaH$_2$PO$_4$, 2.5 CaCl$_2$, 1.3 MgCl$_2$, 10 D-glucose)-filled glass microelectrode (10-15 MΩ) positioned in the stratum radiatum of hippocampal area CA1. During the experiments the slices were perfused in an ACSF that was heated to 33° C. We applied low frequency stimulation (LFS) after stable baseline was established. Stimulus intensity was adjusted to evoke f-EPSP approximately 40% of the maximum. We induced NMDA receptor dependent LTD by a low frequency stimulation at a rate of 1 Hz for 15 min. In WT hippocampal slices the application of LFS induced a CA1 synaptic depression to about 80% of the baseline level. In age-matched transgenic SorCS2 −/− mice the induction of NMDA receptor-dependent LTD was impaired and the efficacy of synaptic transmission 30 minutes after LFS were at the same level as baseline. To verify the integrity of SorCS2-deficient CA1 synapses, we applied polyclonal anti-SorCS2 IgG to wild type hippocampal slices, and the application abolished LTD (FIG. 4C).

Example 10a

In Vivo Electrophysiological Characterization of Hippocampal Long-Term Depression in Stressed Animals by the Injection of a SorCS2 Antagonist Male Wistar rats 200-300 g are implanted with ground, anchor and reference electrodes using previously described techniches (Doyle, Holscher et al. 1996). Recording and stimulating electrodes are places in the stratum radiatum of the CA1 region of the dorsal hippocampus using electrophysiological criteria and verified by post mortem examination. After surgery rats are housed individually (in home cage) having a 12 h light/dark cycle and thermoregulated environment. The rats are left undisturbed in their home cage during a two-week recovery period. Next, a protocol inducing mild naturalistic stress is used: The rats are moved from their home cage and placed in a brightly lit unfamiliar recording box. The ability to induce long-term depression (LTD) in rats treated with a low-molecular weight SorCS2 antagonist, able to cross the blood-brain barrier, is compared with control animals. A low frequency stimulation (LFS) protocol are applied to unhandled, recording-naïve rats 40 min after they are placed for the first time in the brightly lit unfamiliar recording box. In the control group a reliable stable homosynaptic LTD is elicited whereas the rats treated with a SorCS2 antagonist fail to induce LTD.

Example 10b

Treatment of an Animal Model for Depression with a SorCS2 Antagonist

Stress and anxiety-related behavior are tested in the open field and elevated plus maze. By using a chronic mild stress (CMS) protocol we test if stress and anxiety-related behavior is altered in experimentally depressed animals and if a SorCS2 antagonist can prevent this. 24 two-month-old wistar rats are divided into two groups. One group is treated with a SorCS2 antagonist and the control group is injected with Tween 80, 3% NaCl during the complete course of the stress protocol. The two groups are subjected to a stress regimen for three weeks as described in (Moreau et al. 1994). Immediately after the end of the CMS protocol animals are tested in the stress and anxiety-related behavioral open field and elevated plus maze tests.

Example 11

Restoration of Neuronal Hyperactivity in Sortilin Deficient Mice by Exogenous BDNF 3-4 week wildtype and Sortilin deficient mice were examined for neurophysiological in vitro correlates of anxiety/depression like behavior. In fresh 350 μm thick brain slices, inhibitory GABAergic synaptic input to hippocampal granule cells were quantified in living tissues. Electrophysiological patch-clamp recordings were carried out from acute brain slices from WT, Sortilin and Sorcs2 knockout (KO) mice. Following deep isoflurane anesthesia, male mice were sacrificed and the brain was carefully dissected out and cooled. 350 um thick brain slices were cut on a Vibratome 3000 Plus, and the tissue rested in O2/CO2 bubbled Ringer solution for at least 1 hour before experimentation (Drasbek and Jensen 2006). Whole-cell patch-clamp recordings were carried out at 33° C. from the soma of identified granule cells of the dentate gyrus (Jensen and Mody 2001). Under conditions of blocked glutamatergic excitation, GABAergic activity was apparent as spontaneous inhibitory postsynaptic currents (sIPSCs) that could be blocked by the $GABA_A$ receptor antagonist SR95531 (100 μM). For each cell, the frequency of sIPSCs was analyzed and frequencies were pooled within each experimental group. In rescue experiments, BDNF (brain-derived neurotrophic factor, 20 ng/ml) was perfused to the brain slice for at least 5 min and the GABAergic activity was assessed. In whole-cell patch-clamp recordings, Sortilin deficient mice showed an upregulation of the spontaneous activity of the synaptic input from 3.3±1.0 Hz to 6.7±1.6 Hz (by 103%). Subsequently, the pathophysiological neuronal activity was restored in Sortilin deficient mouse brain slices by administering exogenous brain-derived neurotrophic factor (BDNF 20 ng/ml) to the tissue bathing solution (FIG. 8B).

Example 12

Small Molecule Stimulation of SorCS2 Activity

SorCS2 deficient mice show a synaptic GABAergic hyperactivity in the hippocampus and depression-like behaviors in a forced-swim-test and a sucrose-preference-test (Maguire and Mody 2008). A small molecule ligand which stimulates SorCS2 activity is used to restore the synaptic activity back to normal levels. 10 mg/kg body weight of the ligand is injected subcutaneously. Subsequent behavioral analysis shows that the mice during this treatment have recovered from the depression-like symptoms. Also in vitro analysis of brain tissues during the treatment show that the synaptic GABAergic activity has recovered. Based on these animal experiments, the SorCS2 specific ligand can go into Phase I clinical trials for treatment of humans showing anxiety and depression disorders.

Example 13

Alteration of BDNF Secretion in Vps10p Domain Receptor Deficient or Overexpressing Primary Neuronal Cell Cultures Primary neuronal cultures are prepared from brains of Vps10p deficient or overexpressing mice. At postnatal day 0-2 (P0-P2) brains are dissected out, cells are dissociated and plated. Following maturation of the cultures of 2 weeks in vitro, whole-cell patch-clamp recordings are made from single neurons. In the presence of TTX to block action potentials, the neuron is depolarized to elicit the $Ca^{2+}$ dependent release of BDNF as described in (Magby, Bi et al. 2006). The frequency of miniature EPSCs (mEPSCs) will show the altered BDNF secretion from Vps10p deficient or overexpressing neurons.

Example 14

Modulation of BDNF Secretion in Primary Neuronal Cell Cultures by a Vps10p Domain Receptor Antagonist/Agonist Primary neuronal cultures are prepared from brains of WT mice. At postnatal day 0-2 (P0-P2) brains are dissected out, cells are dissociated and plated in the presence or absence of a Vps10p domain receptor antagonist or agonist. Following maturation of the cultures of 2 weeks in vitro, whole-cell patch-clamp recordings are made from single neurons. In the presence of TTX to block action potentials, the neuron is depolarized to elicit the $Ca^{2+}$ dependent release of BDNF as described in (Magby, Bi et al. 2006). The frequency of miniature EPSCs (mEPSCs) will show the altered BDNF secretion from neurons following treatment with a Vps10p domain receptor agonist or antagonist.

Example 15

Neuronal EEG Activity and its Restoration by Vps10p Domain Receptor Antagonists/Agonists In Vivo In vivo electrophysiology is carried out in WT adult mice, or Vps10p domain receptor-deficient or -overexpressing adult mice by implanting intracranial EEG electrodes in the hippocampus (Poisbeau, Williams et al. 1997). After at least 1 week of postsurgical recovery, EEG recordings are made daily at the same hour and in similar environmental conditions. 4-8 min long electrographic recordings are collected and stored on computer. Spectral analyses are made to examine the alterations in neuronal activity in Vps10p deficient or overexpressing mice, and to assess the modulation of neuronal activity by Vps10p domain receptor antagonists/agonists in vivo.

Example 16

The Use of SorCS2 as an Animal Model of Bipolar Disorder

Current animal models of bipolar disorder recreate either the behavioral homologue of mania or depression but not both. SorCS2 −/− mice were tested in an elevated plus maze raised 40 cm above the floor, and consisted of two opposite enclosed arms with 15 cm high opaque walls and two opposite open arms of the same size (35×5 cm). The elevated plus maze was set up in a dim lit room under a video camera connected to a computer under the control of the Any-maze tracking system. Testing sessions of 10 min were carried out for each mouse and measured the number of entries and the time spent in the open arms. The parameters measured were the distance traveled during the course of the experiment, the total number of line crossings between the different zones, the percentage of entries into the open arms (open arm entries/closed arm entries*100), and the percentage of time spent in the open arms. All these parameters were increased for the SorCS2 −/− mice compared to control wild-type mice. This behavioral phenotype suggests that the SorCS2 −/− mice are in a state of mania.

The SorCS2 −/− mice were also tested in a forced swim test, a well-described test for depressive behavior in rodents. The forced swim test employed was essentially similar to that described elsewhere (Porsolt, Le Pichon et al. 1977). Mice were dropped individually into glass cylinders (height: 30 cm, diameter: 15 cm) containing 20 cm water, maintained at 23-25° C., and remained there for 6 min while their movements were recorded using a digital video camera. A mouse was judged to be immobile when it floated in an upright position and made only small movements to keep its head above water. The time of immobility was scored during the last 4 min of the 6 min testing period, after 2 min habituation. The total time spent immobile was highly increased for SorCS2 −/− mice compared to control wild-type mice, suggesting that under these experimental circumstances the SorCS2 −/− mice are in a depressed state.

These findings encourage a pharmaceutical company interested in developing improved pharmaceutical agents for the treatment of bipolar disorder to employ the SorCS2 −/− mice as an animal model of bipolar disorder for testing for potential drug candidates. The drug candidates are mixed into the drinking water at a concentration of e.g. 600 mg/liter and given for e.g. 10 days. Control mice were given normal water. The behavior of the mice is subsequently tested in the elevated plus maze and the forced swim test.

Example 17

Modulation of Synaptic Plasticity by Soluble Sortilin

Lack of NMDA receptor dependent LTD in sortilin −/− hippocampal CA1 synapses by the application of LFS (1 Hz, 15 min) to the Schaffer collaterals was observed. In wt hippocampal CA1 synapses a LFS induced synaptic depression. The NMDA receptor-dependent LTD in Sortilin −/− hippocampal CA1 synapses was rescued by the incubation with 40 ng/ml purified soluble Sortilin for at least 1 h before recording, and present throughout the experiment as indicated. LFS (1 Hz, 15 min) was applied to the Schaffer collaterals. In Sortilin −/− hippocampal slices incubated with control vehicle the LTD was still impaired (FIG. 3C).

Example 18

The Application of Soluble Sortilin for the Treatment of Mental and Behavioural Disorders The soluble domain of human Sortilin is expressed recombinantly at a large scale in a mammalian cell culture and is subsequently purified by for example immunoaffinity chromatography. A device for passive delivery containing purified soluble Sortilin is surgically implanted into the brain of a patient suffering from a mental and behavioural disorder. Good effect is obtained and the patient is set on lifelong treatment.

Example 19

The Application of a Preformed Complex of Sortilin and proBDNF for the Treatment of Mental and Behavioural Disorders The soluble domain of human Sortilin is expressed recombinantly at a large scale in a mammalian cell culture and is subsequently purified by for example immunoaffinity chromatography. Similarly, proBDNF is expressed and purified at a large scale. Soluble Sortilin and proBDNF is incubated together to form a preformed Sortilin:proBDNF complex. A device for passive delivery containing purified preformed Sortilin:proBDNF is surgically implanted into the brain of a patient suffering from a mental and behavioural disorder. Good effect is obtained and the patient is set on lifelong treatment.

Example 20

Methods of Treatment

The resulting developed active agent of peptide/polypeptide nature (possible antibody based) either freeze-dried to be dissolved before use or as a ready to use solution so that it can be given for parenteral administration route (e.g. intravenously (I.V.), intramuscularly (I.M.) or subcutaneously (S.C.). Mucosal application of a solid dose form also represents a possibility in this case.

If the resulting developed active agent is of chemical nature a formulation for oral administration as well as a potential route is prepared e.g. for S.C. or I.M. use.

The developed medicament will either be used for prophylactic purpose or given chronically for long life treatment. In this case the active agent interferes with and thereby prevents the process of molecular events to take place that leads to the symptoms of the mental and behavioural disorders.

In case at that time a genetic test is developed to diagnose individuals predisposed to develop mental and behavioural disorders the medicament should be used were possible in connection with such a diagnostics.

Have a mental and behavioural disorder developed; chronic treatment with the medicament represents another possibility. The rationale is constantly to be able to suppress the molecular events leading to the symptoms of the disease.

Finally it will be possible to co-administer the medicament together with conventional treatments for mental and behavioural disorders e.g. with antidepressants and lithium.

Example 21

Identification of Psychiatric Patients that Will Benefit from Treatment with a Vps10p-Domain Receptor Agonist/Antagonist Patients are identified by the analysis of blood samples from patients suffering from mental and behavioural disorders are analyzed for altered levels of neurotrophic factors and/or Vps10p-domain receptors by enzyme-linked immunosorbent assay (ELISA) and/or by a genetic test. Based on the blood sample analysis, the patients are subsequently prescribed a Vps10p-domain receptor agonist or antagonist.

Example 22

Treatment of a Patient Suffering from Bipolar Disorder

A 27 year-old man is hospitalized in a psychiatric hospital with severe bipolar disorder. The patient has attempted to commit suicide and suffers from drug abuse. A blood sample from the patient is analyzed by ELISA using rabbit polyclonal SorCS2 antibodies for capture and mouse monoclonal antibody followed by horse radish peroxidase coupled swine anti-mouse secondary antibodies (DAKO, P0260) for detection. The analysis reveals that the patient has reduced SorCS2 levels. The patient is subsequently prescribed a SorCS2 agonist that is to be administered orally.

Example 23

Treatment of a Patient Suffering from Anxiety and Depression

A 35 year-old man suffers from anxiety and depression, and analysis of a tissue sample by ELISA reveals low levels of BDNF. The patient is subsequently administered a Sortilin antagonist that is to be administered orally.

Example 24

Screening for the Modulation of Vps10p Receptors Expressed in Cell Lines Using Live Cell Electrophysiology or Imaging Primary cultures are prepared from brains of Vps10p deficient or overexpressing mice. At postnatal day 0-2 (P0-P2) brains are dissected out, cells are dissociated and plated. Following maturation of the cultures of 2 weeks in vitro, whole-cell patch-clamp recordings are made from single neurons. In the presence of TTX to block action potentials, the neuron is depolarized to elicit the Ca2+ dependent release of BDNF (Plummer et al. 2006). The frequency of miniature EPSCs (mEPSCs) will show the altered BDNF secretion from VPS10p deficient or overexpressing neurons.

Example 25

Neurons in primary cell culture. Electrophysiological recordings from single neurons from wildtype mice where ligands are screened for modulation of Vps10p receptors. Electrophysiological recordings from single neurons in primary cultures from Vps10p receptor deficient or overexpressing mice, to examine neuronal excitability, synaptic function and synaptic plasticity (Plummer et al. 2006).

In vivo electrophysiology is carried out in Vps10p deficeit or overexpressing adult mice by implanting intracranial EEG electrodes in the hippocampus (Poisbeau et al (1997) J. Neurosci. 17(10):3467-75). After at least 1 week of postsurgical recovery, EEG recordings are made daily at the same hour and in similar environmental conditions. 4-8 min long electrographic recordings are collected and stored on computer. Spectral analyses are made to examine the alterations in neuronal activity in Vps10p deficient or overexpressing mice, and to assess the modulation of neuronal activity by Vps10p receptor ligands in vivo.

Other electrophysiological screening methods useful for identifying agents of the present invention are:

Brain slices—Intracellular electrophysiological recordings from neurons in slices from brains of Vps10p receptor deficient or overexpressing mice to examine neuronal excitability, synaptic function and synaptic plasticity. Extracellular electrophysiological recordings from brains of Vps10p receptor deficient or overexpressing mice, to examine neuronal excitability, synaptic function and synaptic plasticity.

In vivo electrophysiology—EEG recordings using intracranially implanted electrodes to record the pharmacological modulation of Vps10p receptors, and to examine neuronal activity in Vps10p receptor deficient or overexpressing mice. (Poisbeau et at (1997) J. Neurosci. 17(10):3467-75)

REFERENCES

Andersen, O. M., J. Reiche, et al. (2005). "Neuronal sorting protein-related receptor sorLA/LR11 regulates processing of the amyloid precursor protein." *Proc Natl Acad Sci USA* 102(38): 13461-6.

Baum, A. E., N. Akula, et al. (2008). "A genome-wide association study implicates diacylglycerol kinase eta (DGKH) and several other genes in the etiology of bipolar disorder." *Mol Psychiatry* 13(2): 197-207.

Ben-Ari, Y. and R. Cossart (2000). "Kainate, a double agent that generates seizures: two decades of progress." *Trends Neurosci* 23(11): 580-7.

Buzsaki, G. and A. Draguhn (2004). "Neuronal oscillations in cortical networks." *Science* 304(5679): 1926-9.

Chalon, P., N. Vita, et al. (1996). "Molecular cloning of a levocabastine-sensitive neurotensin binding site." *FEBS Lett* 386(2-3): 91-4.

Chen, B., D. Dowlatshahi, et al. (2001). "Increased hippocampal BDNF immunoreactivity in subjects treated with antidepressant medication." *Biol Psychiatry* 50(4): 260-5.

Chen, Z. Y., A. Ieraci, et al. (2005). "Sortilin controls intracellular sorting of brain-derived neurotrophic factor to the regulated secretory pathway." *J Neurosci* 25(26): 6156-66.

Chen, Z. Y., D. Jing, et al. (2006). "Genetic variant BDNF (Val66Met) polymorphism alters anxiety-related behavior." *Science* 314(5796): 140-3.

Ciechanowski, P. S., W. J. Katon, et al. (2000). "Depression and diabetes: impact of depressive symptoms on adherence, function, and costs." *Arch Intern Med* 160(21): 3278-85.

Clee, S. M., B. S. Yandell, et al. (2006). "Positional cloning of Sorcs1, a type 2 diabetes quantitative trait locus." *Nat Genet.* 38(6): 688-93.

Coyle, J. T. (2007). "What can a clock mutation in mice tell us about bipolar disorder?" *Proc Natl Acad Sci USA* 104(15): 6097-8.

Dodson, S. E., M. Gearing, et al. (2006). "LR11/SorLA expression is reduced in sporadic Alzheimer disease but not in familial Alzheimer disease." *J Neuropathol Exp Neurol* 65(9): 866-72.

Doyle, C., C. Holscher, et al. (1996). "The selective neuronal NO synthase inhibitor 7-nitro-indazole blocks both long-term potentiation and depotentiation of field EPSPs in rat hippocampal CA1 in vivo." *J Neurosci* 16(1): 418-24.

Drasbek, K. R. and K. Jensen (2006). "THIP, a hypnotic and antinociceptive drug, enhances an extrasynaptic GABAA receptor-mediated conductance in mouse neocortex." *Cereb Cortex* 16(8): 1134-41.

Duman, R. S. and L. M. Monteggia (2006). "A neurotrophic model for stress-related mood disorders." *Biol Psychiatry* 59(12): 1116-27.

Egan, M. F., M. Kojima, et al. (2003). "The BDNF val66met polymorphism affects activity-dependent secretion of BDNF and human memory and hippocampal function." *Cell* 112(2): 257-69.

Einat, H. and H. K. Manji (2006). "Cellular plasticity cascades: genes-to-behavior pathways in animal models of bipolar disorder." *Biol Psychiatry* 59(12): 1160-71.

Farrant, M. and Z. Nusser (2005). "Variations on an inhibitory theme: phasic and tonic activation of GABA(A) receptors." *Nat Rev Neurosci* 6(3): 215-29.

Frerking, M., R. C. Malenka, et al. (1998). "Brain-derived neurotrophic factor (BDNF) modulates inhibitory, but not excitatory, transmission in the CA1 region of the hippocampus." *J Neurophysiol* 80(6): 3383-6.

Gama, C. S., A. C. Andreazza, et al. (2007). "Serum levels of brain-derived neurotrophic factor in patients with schizophrenia and bipolar disorder." *Neurosci Lett* 420(1): 45-48.

Goodarzi, M. O., D. M. Lehman, et al. (2007). "SORCS1: a novel human type 2 diabetes susceptibility gene suggested by the mouse." *Diabetes* 56(7): 1922-9.

Granhall, C., H. B. Park, et al. (2006). "High-resolution quantitative trait locus analysis reveals multiple diabetes susceptibility loci mapped to intervals <800 kb in the species-conserved Niddm1i of the GK rat." *Genetics* 174(3): 1565-72.

Henneberger, C., R. Juttner, et al. (2002). "Postsynaptic action of BDNF on GABAergic synaptic transmission in the superficial layers of the mouse superior colliculus." *J Neurophysiol* 88(2): 595-603.

Hermans-Borgmeyer, I., G. Hermey, et al. (1999). "Expression of the 100-kDa neurotensin receptor sortilin during mouse embryonal development." *Brain Res Mol Brain Res* 65(2): 216-9.

Hermey, G., S. J. Keat, et al. (2003). "Characterization of sorCS1, an alternatively spliced receptor with completely different cytoplasmic domains that mediate different trafficking in cells." *J Biol Chem* 278(9): 7390-6.

Hermey, G., N. Plath, et al. (2004). "The three sorCS genes are differentially expressed and regulated by synaptic activity." *J Neurochem* 88(6): 1470-6.

Hermey, G., I. B. Riedel, et al. (1999). "Identification and characterization of SorCS, a third member of a novel receptor family." *Biochem Biophys Res Commun* 266(2): 347-51.

Hermey, G., I. B. Riedel, et al. (2001). "SorCS1, a member of the novel sorting receptor family, is localized in somata and dendrites of neurons throughout the murine brain." *Neurosci Lett* 313(1-2): 83-7.

Hermey, G., H. C. Schaller, et al. (2001). "Transient expression of SorCS in developing telencephalic and mesencephalic structures of the mouse." *Neuroreport* 12(1): 29-32.

Hermey, G., S. S. Sjogaard, et al. (2006). "Tumour necrosis factor alpha-converting enzyme mediates ectodomain shedding of Vps10p-domain receptor family members." *Biochem J* 395(2): 285-93.

Hewitt, S. A. and J. S. Bains (2006). "Brain-derived neurotrophic factor silences GABA synapses onto hypothalamic neuroendocrine cells through a postsynaptic dynamin-mediated mechanism." *J Neurophysiol* 95(4): 2193-8.

Holderbach, R., K. Clark, et al. (2007). "Enhanced long-term synaptic depression in an animal model of depression." *Biol Psychiatry* 62(1): 92-100.

Jacobsen, L., P. Madsen, et al. (2001). "Activation and functional characterization of the mosaic receptor SorLA/LR11." *J Biol Chem* 276(25): 22788-96.

Jacobsen, L., P. Madsen, et al. (1996). "Molecular characterization of a novel human hybrid-type receptor that binds the alpha2-macroglobulin receptor-associated protein." *J Biol Chem* 271(49): 31379-83.

Jansen, P., K. Giehl, et al. (2007). "Roles for the pro-neurotrophin receptor sortilin in neuronal development, aging and brain injury." *Nat Neurosci* 10(11): 1449-57.

Jensen, K. and I. Mody (2001). "L-type Ca2+ channel-mediated short-term plasticity of GABAergic synapses." *Nat Neurosci* 4(10): 975-6.

Kaila, K. (1994). "Ionic basis of GABAA receptor channel function in the nervous system." *Prog Neurobiol* 42(4): 489-537.

Kanaki, T., H. Bujo, et al. (1998). "Developmental regulation of LR11 expression in murine brain." *DNA Cell Biol* 17(8): 647-57.

Kemp, A. and D. Manahan-Vaughan (2007). "Hippocampal long-term depression: master or minion in declarative memory processes?" *Trends Neurosci* 30(3): 111-8.

Kupfer, D. J. (2005). "The increasing medical burden in bipolar disorder." *Jama* 293(20): 2528-30.

Lewis, D. A., T. Hashimoto, et al. (2005). "Cortical inhibitory neurons and schizophrenia." *Nat Rev Neurosci* 6(4): 312-24.

Lopez, A. D. and C. C. Murray (1998). "The global burden of disease, 1990-2020." *Nat Med* 4(11): 1241-3.

Lu, B. and K. Martinowich (2008). "Cell biology of BDNF and its relevance to schizophrenia." *Novartis Found Symp* 289: 119-29; discussion 129-35, 193-5.

Lu, B., P. T. Pang, et al. (2005). "The yin and yang of neurotrophin action." *Nat Rev Neurosci* 6(8): 603-14.

Magby, J. P., C. Bi, et al. (2006). "Single-cell characterization of retrograde signaling by brain-derived neurotrophic factor." *J Neurosci* 26(52): 13531-6.

Maguire, J. and I. Mody (2008). "GABA(A)R plasticity during pregnancy: relevance to postpartum depression." *Neuron* 59(2): 207-13.

Manji, H. K., W. C. Drevets, et al. (2001). "The cellular neurobiology of depression." *Nat Med* 7(5): 541-7.

Marcusson, E. G., B. F. Horazdovsky, et al. (1994). "The sorting receptor for yeast vacuolar carboxypeptidase Y is encoded by the VPS10 gene." *Cell* 77(4): 579-86.

Martinowich, K., H. Manji, et al. (2007). "New insights into BDNF function in depression and anxiety." *Nat Neurosci* 10(9): 1089-93.

Mazella, J., N. Zsurger, et al. (1998). "The 100-kDa neurotensin receptor is gp95/sortilin, a non-G-protein-coupled receptor." *J Biol Chem* 273(41): 26273-6.

Michelson, D., C. Stratakis, et al. (1996). "Bone mineral density in women with depression." *N Engl J Med* 335(16): 1176-81.

Motoi, Y., T. Aizawa, et al. (1999). "Neuronal localization of a novel mosaic apolipoprotein E receptor, LR11, in rat and human brain." *Brain Res* 833(2): 209-15.

Munck Petersen, C., M. S. Nielsen, et al. (1999). "Propeptide cleavage conditions sortilin/neurotensin receptor-3 for ligand binding." *Embo J* 18(3): 595-604.

Musselman, D. L., D. L. Evans, et al. (1998). "The relationship of depression to cardiovascular disease: epidemiology, biology, and treatment." *Arch Gen Psychiatry* 55(7): 580-92.

Nagappan, G. and B. Lu (2005). "Activity-dependent modulation of the BDNF receptor TrkB: mechanisms and implications." *Trends Neurosci* 28(9): 464-71.

Nakamura, K., K. Namekata, et al. (2007). "Intracellular sortilin expression pattern regulates proNGF-induced naturally occurring cell death during development." *Cell Death Differ* 14(8): 1552-4.

Neves-Pereira, M., E. Mundo, et al. (2002). "The brain-derived neurotrophic factor gene confers susceptibility to bipolar disorder: evidence from a family-based association study." *Am J Hum Genet* 71(3): 651-5.

Nielsen, M. S., C. Jacobsen, et al. (1999). "Sortilin/neurotensin receptor-3 binds and mediates degradation of lipoprotein lipase." *J Biol Chem* 274(13): 8832-6.

Nykjaer, A., R. Lee, et al. (2004). "Sortilin is essential for proNGF-induced neuronal cell death." *Nature* 427(6977): 843-8.

Offe, K., S. E. Dodson, et al. (2006). "The lipoprotein receptor LR11 regulates amyloid beta production and amyloid precursor protein traffic in endosomal compartments." *J Neurosci* 26(5): 1596-603.

Olofsdotter, K., O. Lindvall, et al. (2000). "Increased synaptic inhibition in dentate gyrus of mice with reduced levels of endogenous brain-derived neurotrophic factor." *Neuroscience* 101(3): 531-9.

Pang, P. T., H. K. Teng, et al. (2004). "Cleavage of proBDNF by tPA/plasmin is essential for long-term hippocampal plasticity." *Science* 306(5695): 487-91.

Petersen, C. M., M. S. Nielsen, et al. (1997). "Molecular identification of a novel candidate sorting receptor purified from human brain by receptor-associated protein affinity chromatography." *J Biol Chem* 272(6): 3599-605.

Poisbeau, P., S. R. Williams, et al. (1997). "Silent GABAA synapses during flurazepam withdrawal are region-specific in the hippocampal formation." *J Neurosci* 17(10): 3467-75.

Poo, M. M. (2001). "Neurotrophins as synaptic modulators." *Nat Rev Neurosci* 2(1): 24-32.

Porsolt, R. D., M. Le Pichon, et al. (1977). "Depression: a new animal model sensitive to antidepressant treatments." *Nature* 266(5604): 730-2.

Rezgaoui, M., G. Hermey, et al. (2001). "Identification of SorCS2, a novel member of the VPS10 domain containing receptor family, prominently expressed in the developing mouse brain." *Mech Dev* 100(2): 335-8.

Rivera, C., H. Li, et al. (2002). "BDNF-induced TrkB activation down-regulates the K+-Cl− cotransporter KCC2 and impairs neuronal Cl− extrusion." *J Cell Biol* 159(5): 747-52.

Rogaeva, E., Y. Meng, et al. (2007). "The neuronal sortilin-related receptor SORL1 is genetically associated with Alzheimer disease." *Nat Genet.* 39(2): 168-77.

Roybal, K., D. Theobold, et al. (2007). "Mania-like behavior induced by disruption of CLOCK." *Proc Natl Acad Sci USA* 104(15): 6406-11.

Sager, K. L., J. Wuu, et al. (2007). "Neuronal LR11/sorLA expression is reduced in mild cognitive impairment." *Ann Neurol* 62(6): 640-7.

Scherzer, C. R., K. Offe, et al. (2004). "Loss of apolipoprotein E receptor LR11 in Alzheimer disease." *Arch Neurol* 61(8): 1200-5.

Schulz, R., S. R. Beach, et al. (2000). "Association between depression and mortality in older adults: the Cardiovascular Health Study." *Arch Intern Med* 160(12): 1761-8.

Schumacher, J., R. A. Jamra, et al. (2005). "Evidence for a relationship between genetic variants at the brain-derived neurotrophic factor (BDNF) locus and major depression." *Biol Psychiatry* 58(4): 307-14.

Shirayama, Y., A. C. Chen, et al. (2002). "Brain-derived neurotrophic factor produces antidepressant effects in behavioral models of depression." *J Neurosci* 22(8): 3251-61.

Siuciak, J. A., D. R. Lewis, et al. (1997). "Antidepressant-like effect of brain-derived neurotrophic factor (BDNF)." *Pharmacol Biochem Behav* 56(1): 131-7.

Somogyi, P., G. Tamas, et al. (1998). "Salient features of synaptic organisation in the cerebral cortex." *Brain Res Brain Res Rev* 26(2-3): 113-35.

Spoelgen, R., C. A. von Arnim, et al. (2006). "Interaction of the cytosolic domains of sorLA/LR11 with the amyloid precursor protein (APP) and beta-secretase beta-site APP-cleaving enzyme." *J Neurosci* 26(2): 418-28.

Tanaka, K., M. Masu, et al. (1990). "Structure and functional expression of the cloned rat neurotensin receptor." *Neuron* 4(6): 847-54.

Teng, H. K., K. K. Teng, et al. (2005). "ProBDNF induces neuronal apoptosis via activation of a receptor complex of p75NTR and sortilin." *J Neurosci* 25(22): 5455-63.

Vincent, J. P., J. Mazella, et al. (1999). "Neurotensin and neurotensin receptors." *Trends Pharmacol Sci* 20(7): 302-9.

Westergaard, U. B., K. Kirkegaard, et al. (2005). "SorCS3 does not require propeptide cleavage to bind nerve growth factor." *FEBS Lett* 579(5): 1172-6.

Westergaard, U. B., E. S. Sorensen, et al. (2004). "Functional organization of the sortilin Vps10p domain." *J Biol Chem* 279(48): 50221-9.

Willnow, T. E., Herz, J. (1994). "Homologous recombination for gene replacement in mouse cell lines." *Methods in Cell Biology* 43: 305-334

Woo, N. H., H. K. Teng, et al. (2005). "Activation of p75NTR by proBDNF facilitates hippocampal long-term depression." *Nat Neurosci* 8(8): 1069-77.

Xu, L., R. Anwyl, et al. (1997). "Behavioural stress facilitates the induction of long-term depression in the hippocampus." *Nature* 387(6632): 497-500.

```
Sequence list
SEQ ID NO 1: Homo sapiens Sortilin
Swiss Prot primary accession number: Q99523
Secondary accession number: Q8IZ49
MERPWGAADGLSRWPHGLGLLLLLQLLPPSTLSQDRLDAPPPPAAPLPRW

SGPIGVSWGLRAAAAGGAFPRGGRWRRSAPGEDEECGRVRDFVAKLANNT

HQHVFDDLRGSVSLSWVGDSTGVILVLTTFHVPLVIMTFGQSKLYRSEDY

GKNFKDITDLINNTFIRTEFGMAIGPENSGKVVLTAEVSGGSRGGRIFRS

SDFAKNFVQTDLPFHPLTQMMYSPQNSDYLLALSTENGLWVSKNFGGKWE

EIHKAVCLAKWGSDNTIFFTTYANGSCKADLGALELWRTSDLGKSFKTIG

VKIYSFGLGGRFLFASVMADKDTTRRIHVSTDQGDTWSMAQLPSVGQEQF

YSILAANDDMVFMHVDEPGDTGFGTIFTSDDRGIVYSKSLDRHLYTTTGG

ETDFTNVTSLRGVYITSVLSEDNSIQTMITFDQGGRWTHLRKPENSECDA

TAKNKNECSLHIHASYSISQKLNVPMAPLSEPNAVGIVIAHGSVGDAISV

MVPDVYISDDGGYSWTKMLEGPHYYTILDSGGIIVAIEHSSRPINVIKFS

TDEGQCWQTYTFTRDPIYFTGLASEPGARSMNISIWGFTESFLTSQWVSY

TIDFKDILERNCEEKDYTIWLAHSTDPEDYEDGCILGYKEQFLRLRKSSV

CQNGRDYVVTKQPSICLCSLEDFLCDFGYYRPENDSKCVEQPELKGHDLE

FCLYGREEHLTTNGYRKIPGDKCQGGVNPVREVKDLKKKCTSNFLSPEKQ

NSKSNSVPIILAIVGLMLVTVVAGVLIVKKYVCGGRFLVHRYSVLQQHAE

ANGVDGVDALDTASHTNKSGYHDDSDEDLLE

SEQ ID NO 2: Homo sapiens SorLA polypeptide
Swiss Prot primary accession number: Q92673
Secondary accession number: Q92856
MATRSSRRESRLPFLFTLVALLPPGALCEVWTQRLHGGSAPLPQDRGFLV

VQGDPRELRLWARGDARGASRADEKPLRRKRSAALQPEPIKVYGQVSLND

SHNQMVVHWAGEKSNVIVALARDSLALARPKSSDVYVSYDYGKSFKKISD

KLNFGLGNRSEAVIAQFYHSPADNKRYIFADAYAQYLWITFDFCNTLQGF

SIPFRAADLLLHSKASNLLLGFDRSHPNKQLWKSDDFGQTWIMIQEHVKS

FSWGIDPYDKPNTIYIERHEPSGYSTVFRSTDFFQSRENQEVILEEVRDF

QLRDKYMFATKVVHLLGSEQQSSVQLWVSFGRKPMRAAQFVTRHPINEYY

IADASEDQVFVCVSHSNNRTNLYISEAEGLKFSLSLENVLYYSPGGAGSD

TLVRYFANEPFADFHRVEGLQGVYIATLINGSMNEENMRSVITFDKGGTW

EFLQAPAFTGYGEKINCELSQGCSLHLAQRLSQLLNLQLRRMPILSKESA

PGLIIATGSVGKNLASKINVYISSSAGARWREALPGPHYYTWGDHGGIIT

AIAQGMETNELKYSTNEGETWKTFIFSEKPVFVYGLLTEPGEKSTVFTIF

GSNKENVHSWLILQVNATDALGVPCTENDYKLWSPSDERGNECLLGHKTV

FKRRTPHATCFNGEDFDRPVVVSNCSCTREDYECDFGFKMSEDLSLEVCV

PDPEFSGKSYSPPVPCPVGSTYRRTRGYRKISGDTCSGGDVEARLEGELV

PCPLAEENEFILYAVRKSIYRYDLASGATEQLPLTGLRAAVALDFDYEHN

CLYWSDLALDVIQRLCLNGSTGQEVIINSGLETVEALAFEPLSQLLYWVD

AGFKKIEVANPDGDFRLTIVNSSVLDRPRALVLVPQEGVMFWTDWGDLKP

GIYRSNMDGSAAYHLVSEDVKWPNGISVDDQWIYWTDAYLECIERITFSG

QQRSVILDNLPHPYAIAVFKNEIYWDDWSQLSIFRASKYSGSQMEILANQ

LTGLMDMKIFYKGKNTGSNACVPRPCSLLCLPKANNSRSCRCPEDVSSSV

LPSGDLMCDCPQGYQLKNNTCVKEENTCLRNQYRCSNGNCINSIWWCDFD

NDCGDMSDERNCPTTICDLDTQFRCQESGTCIPLSYKCDLEDDCGDNSDE

SHCEMHQCRSDEYNCSSGMCIRSSWVCDGDNDCRDWSDEANCTAIYHTCE

ASNFQCRNGHCIPQRWACDGDTDCQDGSDEDPVNCEKKCNGFRCPNGTCI

PSSKHCDGLRDCSDGSDEQHCEPLCTHFMDFVCKNRQQCLFHSMVCDGII

QCRDGSDEDAAFAGCSQDPEFHKVCDEFGFQCQNGVCISLIWKCDGMDDC

GDYSDEANCENPTEAPNCSRYFQFRCENGHCIPNRWKCDRENDCGDWSDE

KDCGDSHILPFSTPGPSTCLPNYYRCSSGTCVMDTWVCDGYRDCADGSDE

EACPLLANVTAASTPTQLGRCDRFEFECHQPKTCIPNWKRCDGHQDCQDG

RDEANCPTHSTLTCMSREFQCEDGEACIVLSERCDGFLDCSDESDEKACS

DELTVYKVQNLQWTADFSGDVTLTWMRPKKMPSASCVYNVYYRVVGESIW

KTLETHSNKTNTVLKVLKPDTTYQVKVQVQCLSKAHNTNDFVTLRTPEGL

PDAPRNLQLSLPREAEGVIVGHWAPPIHTHGLIREYIVEYSRSGSKMWAS

QRAASNFTEIKNLLVNTLYTVRVAAVTSRGIGNWSDSKSITTIKGKVIPP

PDIHIDSYGENYLSFTLTMESDIKVNGYVVNLFWAFDTHKQERRTLNFRG

SILSHKVGNLTAHTSYEISAWAKTDLGDSPLAFEHVMTRGVRPPAPSLKA

KAINQTAVECTWTGPRNVVYGIFYATSFLDLYRNPKSLITSLHNKTVIVS

KDEQYLFLVRVVVPYQGPSSDYVVVKMIPDSRLPPRHLHVVHTGKTSVVI

KWESPYDSPDQDLLYAIAVKDLIRKTDRSYKVKSRNSTVEYTLNKLEPGG

KYHIIVQLGNMSKDSSIKITTVSLSAPDALKIITENDHVLLFWKSLALKE

KHFNESRGYEIHMFDSAMNITAYLGNTTDNFFKISNLKMGHNYTFTVQAR

CLFGNQICGEPAILLYDELGSGADASATQAARSTDVAAVVVPILFLILLS

LGVGFAILYTKHRRLQSSFTAFANSHYSSRLGSAIFSSGDDLGEDDEDAP

MITGFSDDVPMVIA

SEQ ID NO 3: Homo sapiens SorCS1
Swiss Prot primary accession number: Q8WY21
Secondary accession numbers: Q59GG7 Q5JVT7
Q5JVT8 Q5VY14 Q86WQ1 Q86WQ2 Q9H1Y1 Q9H1Y2
MGKVGAGGGSQARLSALLAGAGLLILCAPGVCGGGSCCPSPHPSSAPRSA

STPRGFSHQGRPGRAPATPLPLVVRPLFSVAPGDRALSLERARGTGASMA

VAARSGRRRRSGADQEKAERGEGASRSPRGVLRDGGQQEPGTRERDPDKA

TRFRMEELRLTSTTFALTGDSAHNQAMVHWSGHNSSVILILTKLYDYNLG

SITESSLWRSTDYGTTYEKLNDKVGLKTILSYLYVCPTNKRKIMLLTDPE

IESSLLISSDEGATYQKYRLNFYIQSLLFHPKQEDWILAYSQDQKLYSSA

EFGRRWQLIQEGVVPNRFYWSVMGSNKEPDLVHLEARTVDGHSHYLTCRM
```

QNCTEANRNQPFPGYIDPDSLIVQDHYVFVQLTSGGRPHYYVSYRRNAFA

QMKLPKYALPKDMHVISTDENQVFAAVQEWNQNDTYNLYISDTRGVYFTL

ALENVQSSRGPEGNIMIDLYEVAGIKGMFLANKKIDNQVKTFITYNKGRD

WRLLQAPDTDLRGDPVHCLLPYCSLHLHLKVSENPYTSGIIASKDTAPSI

IVASGNIGSELSDTDISMFVSSDAGNTWRQIFEEEHSVLYLDQGGVLVAM

KHTSLPIRHLWLSFDEGRSWSKYSFTSIPLFVDGVLGEPGEETLIMTVFG

HFSHRSEWQLVKVDYKSIFDRRCAEEDYRPWQLHSQGEACIMGAKRIYKK

RKSERKCMQGKYAGAMESEPCVCTEADFDCDYGYERHSNGQCLPAFWFNP

SSLSKDCSLGQSYLNSTGYRKVVSNNCTDGVREQYTAKPQKCPGKAPRGL

RIVTADGKLTAEQGHNVTLMVQLEEGDVQRTLIQVDFGDGIAVSYVNLSS

MEDGIKHVYQNVGIFRVTVQVDNSLGSDSAVLYLHVTCPLEHVHLSLPFV

TTKNKEVNATAVLWPSQVGTLTYVWWYGNNTEPLITLEGSISFRFTSEGM

NTITVQVSAGNAILQDTKTIAVYEEFRSLRLSFSPNLDDYNPDIPEWRRD

IGRVIKKSLVEATGVPGQHILVAVLPGLPTTAELFVLPYQDPAGENKRST

DDLEQISELLIHTLNQNSVHFELKPGVRVLVHAAHLTAAPLVDLTPTHSG

SAMLMLLSVVFVGLAVFVIYKFKRRVALPSPPSPSTQPGDSSLRLQRARH

ATPPSTPKRGSA-

GAQYAI

SEQ ID NO 4: *Homo sapiens* SorCS2
Swiss Prot primary accession number: Q96PQ0
Secondary accession number: Q9P2L7
MAHRGPSRASKGPGPTARAPSPGAPPPPRSPRSRPLLLLLLLLGACGAAG

RSPEPGRLGPHAQLTRVPRSPPAGRAEPGGGEDRQARGTEPGAPGPSPGP

APGPGEDGAPAAGYRRWERAAPLAGVASRAQVSLISTSFVLKGDATHNQA

MVHWTGENSSVILILTKYYHADMGKVLESSLWRSSDFGTSYTKLTLQPGV

TTVIDNFYICPTNKRKVILVSSSLSDRDQSLFLSADEGATFQKQPIPFFV

ETLIFHPKEEDKVLAYTKESKLYVSSDLGKKWTLLQERVTKDHVFWSVSG

VDADPDLVHVEAQDLGGDFRYVTCAIHNCSEKMLTAPFAGPIDHGSLTVQ

DDYIFFKATSANQTKYYVSYRRNEFVLMKLPKYALPKDLQIISTDESQVF

VAVQEWYQMDTYNLYQSDPRGVRYALVLQDVRSSRQAEESVLIDILEVRG

VKGVFLANQKIDGKVMTLITYNKGRDWDYLRPPSMDMNGKPTNCKPPDCH

LHLHLRWADNPYVSGTVHTKDTAPGLIMGAGNLGSQLVEYKEEMYITSDC

GHTWRQVFEEEHHILYLDHGGVIVAIKDTSIPLKILKFSVDEGLTWSTHN

FTSTSVFVDGLLSEPGDETLVMTVFGHISFRSDWELVKVDFRPSFSRQCG

EEDYSSWELSNLQGDRCIMGQQRSFRKRKSTSWCIKGRSFTSALTSRVCE

CRDSDFLCDYGFERSPSSESSTNKCSANFWFNPLSPPDDCALGQTYTSSL

GYRKVVSNVCEGGVDMQQSQVQLQCPLTPPRGLQVSIQGEAVAVRPGEDV

LFVVRQEQGDVLTTKYQVDLGDGFKAMYVNLTLTGEPIRHRYESPGIYRV

SVRAENTAGHDEAVLFVQVNSPLQALYLEVVPVIGLNQEVNLTAVLLPLN

PNLTVFYWWIGHSLQPLLSLDNSVTTRFSDTGDVRVTVQAACGNSVLQDS

RVLRVLDQFQVMPLQFSKELDAYNPNTPEWREDVGLVVTRLLSKETSVPQ

ELLVTVVKPGLPTLADLYVLLPPPRPTRKRSLSSDKRLAAIQQVLNAQKI

SFLLRGGVRVLVALRDTGTGAEQLGGGGGYWAVVVLFVIGLFAAGAFILY

KFKRKRPGRTVYAQMHNEKEQEMTSPVSHSEDVQGAVQGNHSGVVLSINS

REMHSYLVS

SEQ ID NO 5: *Homo sapiens* SorCS3
Swiss Prot primary accession number: Q9UPU3
Secondary accession numbers: Q5VXF9 Q9NQJ2
MEAARTERPAGRPGAPLVRTGLLLLSTWVLAGAEITWDATGGPGRPAAPA

SRPPALSPLSPRAVASQWPEELASARRAAVLGRRAGPELLPQQGGGRGGE

MQVEAGGTSPAGERRGRGIPAPAKLGGAARRSRRAQPPITQERGDAWATAP

ADGSRGSRPLAKGSREEVKAPRAGGSAAEDLRLPSTSFALTGDSAHNQAM

VHWSGHNSSVILILTKLYDFNLGSVTESSLWRSTDYGTTYEKLNDKVGLK

TVLSYLYVNPTNKRKIMLLSDPEMESSILISSDEGATYQKYRLTFYIQSL

LFHPKQEDWVLAYSLDQKLYSSMDFGRRWQLMHERITPNRFYWSVAGLDK

EADLVHMEVRTTDGYAHYLTCRIQECAETTRSGPFARSIDISSLVVQDEY

IFIQVTTSGRASYYVSYRREAFAQIKLPKYSLPKDMHIISTDENQVFAAV

QEWNQNDTYNLYISDTRGIYFTLAMENIKSSRGLMGNIIIELYEVAGIKG

IFLANKKVDDQVKTYITYNKGRDWRLLQAPDVDLRGSPVHCLLPFCSLHL

HLQLSENPYSSGRISSKETAPGLVVATGNIGPELSYTDIGVFISSDGGNT

WRQIFDEEYNVWFLDWGGALVAMKHTPLPVRHLWVSFDEGHSWDKYGFTS

VPLFVDGALVEAGMETHIMTVFGHFSLRSEWQLVKVDYKSIFSRHCTKED

YQTWHLLNQGEPCVMGERKIFKKRKPGAQCALGRDHSGSVVSEPCVCANW

DFECDYGYERHGESQCVPAF-

WYNPASPSKD

CSLGQSYLNSTGYRRIVSNNCTDGLREKYTAKAQMCPGKAPRGLHVVTTD

GRL-

VAEQGHN

ATFIILMEEGDLQRTNIQLDFGDGIAVSYANFSPIEDGIKHVYKSAGIFQ

VTA-

YAENNLG

SDTAVLFLHVVCPVEHVHLRVPFVAIRNKEVNISAVVWPSQLGTLTYFWW

FGNST-

KPLIT

LDSSISFTFLAEGTDTITVQVAAGNALIQDTKEIAVHEYFQSQLLSFSPN

LDYHNP-

DIPE

WRKDIGNVIKRALVKVTSVPEDQILIAVFPGLPTSAELFILPPKNLTERR

KGNEG-

DLEQI

VETLFNALNQNLVQFELKPGVQVIVYVTQLTLAPLVDSSAGHSSSAMLML

LSV-

VFVGLAV

FLIYKFKRKIPWINIYAQVQHDKEQEMIGSVSQSENAPKITLSDFTEPEE

LL-

DKELDTRV

IGGIATIANSESTKEIPNCTSV

SEQ ID NO 6: *Homo sapiens* pre-pro-BDNF
polypeptide
Swiss-Prot primary accession number: P23560
MTILFLTMVISYFGCMKAAPMKEANIRGQGGLAYPGVRTHGTLESVN-

GPKAGSRGLTSLADTFEHVIEELLDEDQKVRPNEENNKDADLYTSRVM-

LSSQVPLEPPLLFLLEEYKNYLDAANMSMRVRRHSDPARRGELSVCDSIS

EWV-

TAADKKTAVDMSGGIVTVLEKVPVSKGQLKQYFYETKCNPMGYTKEGCR-

GIDKRHWNSQCRTTQSYVRALTMDSKKRIGWRFIRIDTSCVCTLTIKRGR

SEQ ID NO 7: *Homo sapiens* TrkA
Swiss Prot primary accession number P04629
Secondary accession numbers P08119 Q15655
Q15656 Q5D056 Q5VZS2 Q7Z5C3 Q9UIU7
MLRGGRRGQLGWHSWAAGPGSLLAWLILASAGAAPCDACCPHGSSGLRC

TRDGALDSLHHLPGAENLTELYIENQQHLQHLELRDLRGLGELRNLTIVK

SGLRFVAPDAFHFTPRLSRLNLSFNALESLSWKTVQGLSLQELVLSGNPL

HCSCALRWLQRWEEEGLGGVPEQKLQCHGQGPLAHMPNASCGVPTLKVQV

PNASVDVGDDVLLRCQVEGRGLEQAGWILTELEQSATVMKSGGLPSLGLT

LANVTSDLNRKNVTCWAENDVGRAEVSVQVNVSFPASVQLHTAVEMHHWC

IPFSVDGQPAPSLRWLFNGSVLNETSFIFTEFLEPAANETVRHGCLRLNQ

PTHVNNGNYTLLAANPFGQASASIMAAFMDNPFEFNPEDPIPVSFSPVDT

NSTSGDPVEKKDETPFGVSVAVGLAVFACLFLSTLLLVLNKCGRRNKFGI

NRPAVLAPEDGLAMSLHFMTLGGSSLSPTEGKGSGLQGHIIENPQYFSDA

CVHHIKRRDIVLKWELGEGAFGKVFLAECHNLLPEQDKMLVAVKALKEAS

ESARQDFQREAELLTMLQHQHIVRFFGVCTEGRPLLMVFEYMRHGDLNRF

LRSHGPDAKLLAGGEDVAPGPLGLGQLLAVASQVAAGMVYLAGLHFVHRD

LATRNCLVGQGLVVKIGDFGMSRDIYSTDYYRVGGRTMLPIRWMPPESIL

YRKFTTESDVWSFGVVLWEIFTYGKQPWYQLSNTEAIDCITQGRELERPR

ACPPEVYAIMRGCWQREPQQRHSIKDVHARLQALAQAPPVYLDVLG

SEQ ID NO 8: *Homo sapiens* TrkB
Swiss Prot primary accession number Q16620
Secondary accession numbers Q16675 Q8WXJ6
MSSWIRWHGPAMARLWGFCWLVVGFWRAAFACPTSCKCSASRIWCSDPSP

GIVAFPRLEPNSVDPENITEIFIANQKRLEIINEDDVEAYVGLRNLTIVD

SGLKFVAHKAFLKNSNLQHINFTRNKLTSLSRKHFRHLDLSELILVGNPF

TCSCDIMWIKTLQEAKSSPDTQDLYCLNESSKNIPLANLQIPNCGLPSAN

LAAPNLTVEEGKSITLSCSVAGDPVPNMYWDVGNLVSKHMNETSHTQGSL

RITNISSDDSGKQISCVAENLVGEDQDSVNLTVHFAPTITFLESPTSDHH

WCIPFTVKGNPKPALQWFYNGAILNESKYICTKIHVTNHTEYHGCLQLDN

PTHMNNGDYTLIAKNEYGKDEKQISAHFMGWPGIDDGANPNYPDVIYEDY

GTAANDIGDTTNRSNEIPSTDVTDKTGREHLSVYAVVVIASVVGFCLLVM

LFLLKLARHSKFGMKGPASVISNDDDSASPLHHISNGSNTPSSSEGGPDA

VIIGMTKIPVIENPQYFGITNSQLKPDTFVQHIKRHNIVLKRELGEGAFG

KVFLAECYNLCPEQDKILVAVKTLKDASDNARKDFHREAELLTNLQHEHI

VKFYGVCVEGDPLIMVFEYMKHGDLNKFLRAHGPDAVLMAEGNPPTELTQ

SQMLHIAQQIAAGMVYLASQHFVHRDLATRNCLVGENLLVKIGDFGMSRD

VYSTDYYRVGGHTMLPIRWMPPESIMYRKFTTESDVWSLGVVLWEIFTYG

KQPWYQLSNNEVIECITQGRVLQRPRTCPQEVYELMLGCWQREPHMRKNI

KGIHTLLQNLAKASPVYLDILG

SEQ ID NO 9: *Homo sapiens* TrkC
Swiss Prot primary accession number Q16288
Secondary accession numbers O75682 Q12827 Q16289
MDVSLCPAKCSFWRIFLLGSVWLDYVGSVLACPANCVCSKTEINCRRPDD

GNLFPLLEGQDSGNSNGNASINITDISRNITSIHIENWRSLHTLNAVDME

LYTGLQKLTIKNSGLRSIQPRAFAKNPHLRYINLSSNRLTTLSWQLFQTL

SLRELQLEQNFFNCSCDIRWMQLWQEQGEAKLNSQNLYCINADGSQLPLF

RMNISQCDLPEISVSHVNLTVREGDNAVITCNGSGSPLPDVDWIVTGLQS

INTHQTNLNWTNVHAINLTLVNVTSEDNGFTLTCIAENVVGMSNASVALT

VYYPPRVVSLEEPELRLEHCIEFVVRGNPPPTLHWLHNGQPLRESKIIHV

EYYQEGEISEGCLLFNKPTHYNNGNYTLIAKNPLGTANQTINGHFLKEPF

PESTDNFILFDEVSPTPPITVTHKPEEDTFGVSIAVGLAAFACVLLVVLF

VMINKYGRRSKFGMKGPVAVISGEEDSASPLHHINHGITTPSSLDAGPDT

VVIGMTRIPVIENPQYFRQGHNCHKPDTYVQHIKRRDIVLKRELGEGAFG

KVFLAECYNLSPTKDKMLVAVKALKDPTLAARKDFQREAELLTNLQHEHI

VKFYGVCGDGDPLIMVFEYMKHGDLNKFLRAHGPDAMILVDGQPRQAKGE

LGLSQMLHIASQIASGMVYLASQHFVHRDLATRNCLVGANLLVKIGDFGM

SRDVYSTDYYRLFNPSGNDFCIWCEVGGHTMLPIRWMPPESIMYRKFTTE

SDVWSFGVILWEIFTYGKQPWFQLSNTEVIECITQGRVLERPRVCPKEVY

DVMLGCWQREPQQRLNIKEIYKILHALGKATPIYLDILG

SEQ ID NO 10: *Homo sapiens* p75$^{NTR}$
Swiss Prot P08138
MGAGATGRAMDGPRLLLLLLLGVSLGGAKEACPTGLYTHSGECCKACNLG

EGVAQPCGANQTVCEPCLDSVTFSDVVSATEPCKPCTECVGLQSMSAPCV

EADDAVCRCAYGYYQDETTGRCEACRVCEAGSGLVFSCQDKQNTVCEECP

DGTYSDEANHVDPCLPCTVCEDTERQLRECTRWADAECEEIPGRWITRST

PPEGSDSTAPSTQEPEAPPEQDLIASTVAGVVTTVMGSSQPVVTRGTTDN

LIPVYCSILAAVVVGLVAYIAFKRWNSCKQNKQGANSRPVNQTPPPEGEK

LHSDSGISVDSQSLHDQQPHTQTASGQALKGDGGLYSSLPPAKREEVEKL

LNGSAGDTWRHLAGELGYQPEHIDSFTHEACPVRALLASWATQDSATLDA

LLAALRRIQRADLVESLCSESTATSPV

The invention claimed is:

1. A method for treating a disorder selected from the group consisting of anxiety and stress in an individual in need thereof, said method comprising administering to said individual, a therapeutically effective amount of a sortilin-related Vps10p domain-containing receptor 2 (SorCS2) modulator or a Sortilin modulator, wherein:
   (A) the SorCS2 modulator is an anti-SorCS2 polyclonal antibody or a fragment thereof which binds to SorCS2, or is an anti-SorCS2 monoclonal antibody or a fragment thereof which binds to SorCS2; and
   (B) the Sortilin modulator is an anti-Sortilin polyclonal antibody or a fragment thereof which binds to Sortilin, or is an anti-Sortilin monoclonal antibody or a fragment thereof which binds to Sortilin.

2. The method of claim 1, wherein said method comprises administering said SorCS2 modulator.

3. The method of claim 2, wherein the antibody is a polyclonal anti-SorCS2 IgG, or said fragment thereof.

4. The method of claim 1, wherein said method comprises administering said Sortilin modulator.

5. The method of claim 4, wherein said monoclonal or polyclonal antibody inhibits interaction between the extracellular domain of Sortilin and the extracellular domain of a Tyrosine Kinase receptor selected from the group consisting of the neurotrophic tyrosine kinase receptor type 1 (TrkA), the neurotrophic tyrosine kinase receptor type 2 (TrkB) and the neurotrophic tyrosine kinase receptor type 3 (TrkC).

6. The method of claim 1, wherein said monoclonal or polyclonal antibody modulates the interaction between SorCS2 and an interaction partner selected from the group consisting of the p75 neurotrophin receptor (p75$^{NTR}$), the neurotrophic tyrosine kinase receptor type 2 (TrkB), a p75NTR:TrkB binary complex, the propeptide of brain-derived neurotrophic factor (proBDNF), mature brain-derived neurotrophic factor (mature BDNF), glutamate receptor (GluR), α-amino-3-hydroxy-5-methyl-4-isoxazole-propionic acid receptor (AMPA-R) and the N-methyl-D-aspartate receptor (NMDA-receptor).

7. The method of claim 6, wherein said antibody inhibits interaction between SorCS2 and the p75NTR:TrkB binary complex.

8. The method of claim 1, wherein said antibody modulates the interaction between SorCS2 and a ligand selected from the group consisting of p75NTR, TrkB, the propeptide of proBDNF, and mature BDNF.

* * * * *

UNITED STATES PATENT AND TRADEMARK OFFICE
CERTIFICATE OF CORRECTION

PATENT NO. : 8,703,125 B2
APPLICATION NO. : 13/140515
DATED : April 22, 2014
INVENTOR(S) : Pedersen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 170 days.

Signed and Sealed this
Twenty-ninth Day of September, 2015

Michelle K. Lee
*Director of the United States Patent and Trademark Office*

SEQUENCE LISTING

<160> NUMBER OF SEQ ID NOS: 10

<210> SEQ ID NO 1
<211> LENGTH: 831
<212> TYPE: PRT
<213> ORGANISM: Homo sapiens

<400> SEQUENCE: 1

```
Met Glu Arg Pro Trp Gly Ala Ala Asp Gly Leu Ser Arg Trp Pro His
 1               5                  10                  15

Gly Leu Gly Leu Leu Leu Leu Gln Leu Leu Pro Pro Ser Thr Leu
                20                  25                  30

Ser Gln Asp Arg Leu Asp Ala Pro Pro Pro Ala Ala Pro Leu Pro
                35                  40                  45

Arg Trp Ser Gly Pro Ile Gly Val Ser Trp Gly Leu Arg Ala Ala Ala
        50                  55                  60

Ala Gly Gly Ala Phe Pro Arg Gly Gly Arg Trp Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
                100                 105                 110

Ser Leu Ser Trp Val Gly Asp Ser Thr Gly Val Ile Leu Val Leu Thr
                115                 120                 125

Thr Phe His Val Pro Leu Val Ile Met Thr Phe Gly Gln Ser Lys Leu
            130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
                180                 185                 190

Arg Gly Gly Arg Ile Phe Arg Ser Ser Asp Phe Ala Lys Asn Phe Val
            195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365
```

```
Gly Asp Thr Gly Phe Gly Thr Ile Phe Thr Ser Asp Arg Gly Ile
    370                 375                 380

Val Tyr Ser Lys Ser Leu Asp Arg His Leu Tyr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
                420                 425                 430

Gln Gly Gly Arg Trp Thr His Leu Arg Lys Pro Glu Asn Ser Glu Cys
            435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
                500                 505                 510

Tyr Ser Trp Thr Lys Met Leu Glu Gly Pro His Tyr Thr Ile Leu
            515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
                595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Val Pro Ile Ile Leu Ala Ile Val Gly Leu Met Leu
        755                 760                 765

Val Thr Val Val Ala Gly Val Leu Ile Val Lys Lys Tyr Val Cys Gly
770                 775                 780
```

```
Gly Arg Phe Leu Val His Arg Tyr Ser Val Leu Gln Gln His Ala Glu
785                 790                 795                 800

Ala Asn Gly Val Asp Gly Val Asp Ala Leu Asp Thr Ala Ser His Thr
            805                 810                 815

Asn Lys Ser Gly Tyr His Asp Asp Ser Asp Glu Asp Leu Leu Glu
        820                 825                 830

<210> SEQ ID NO 2
<211> LENGTH: 2214
<212> TYPE: PRT
<213> ORGANISM: Homo sapiens

<400> SEQUENCE: 2

Met Ala Thr Arg Ser Ser Arg Arg Glu Ser Arg Leu Pro Phe Leu Phe
1               5                   10                  15

Thr Leu Val Ala Leu Leu Pro Pro Gly Ala Leu Cys Glu Val Trp Thr
            20                  25                  30

Gln Arg Leu His Gly Gly Ser Ala Pro Leu Pro Gln Asp Arg Gly Phe
        35                  40                  45

Leu Val Val Gln Gly Asp Pro Arg Glu Leu Arg Leu Trp Ala Arg Gly
    50                  55                  60

Asp Ala Arg Gly Ala Ser Arg Ala Asp Glu Lys Pro Leu Arg Arg Lys
65                  70                  75                  80

Arg Ser Ala Ala Leu Gln Pro Glu Pro Ile Lys Val Tyr Gly Gln Val
                85                  90                  95

Ser Leu Asn Asp Ser His Asn Gln Met Val Val His Trp Ala Gly Glu
            100                 105                 110

Lys Ser Asn Val Ile Val Ala Leu Ala Arg Asp Ser Leu Ala Leu Ala
        115                 120                 125

Arg Pro Lys Ser Ser Asp Val Tyr Val Ser Tyr Asp Tyr Gly Lys Ser
    130                 135                 140

Phe Lys Lys Ile Ser Asp Lys Leu Asn Phe Gly Leu Gly Asn Arg Ser
145                 150                 155                 160

Glu Ala Val Ile Ala Gln Phe Tyr His Ser Pro Ala Asp Asn Lys Arg
                165                 170                 175

Tyr Ile Phe Ala Asp Ala Tyr Ala Gln Tyr Leu Trp Ile Thr Phe Asp
            180                 185                 190

Phe Cys Asn Thr Leu Gln Gly Phe Ser Ile Pro Phe Arg Ala Ala Asp
        195                 200                 205

Leu Leu Leu His Ser Lys Ala Ser Asn Leu Leu Leu Gly Phe Asp Arg
    210                 215                 220

Ser His Pro Asn Lys Gln Leu Trp Lys Ser Asp Asp Phe Gly Gln Thr
225                 230                 235                 240

Trp Ile Met Ile Gln Glu His Val Lys Ser Phe Ser Trp Gly Ile Asp
                245                 250                 255

Pro Tyr Asp Lys Pro Asn Thr Ile Tyr Ile Glu Arg His Glu Pro Ser
            260                 265                 270

Gly Tyr Ser Thr Val Phe Arg Ser Thr Asp Phe Phe Gln Ser Arg Glu
        275                 280                 285

Asn Gln Glu Val Ile Leu Glu Glu Val Arg Asp Phe Gln Leu Arg Asp
    290                 295                 300

Lys Tyr Met Phe Ala Thr Lys Val Val His Leu Leu Gly Ser Glu Gln
305                 310                 315                 320

Gln Ser Ser Val Gln Leu Trp Val Ser Phe Gly Arg Lys Pro Met Arg
                325                 330                 335
```

-continued

Ala Ala Gln Phe Val Thr Arg His Pro Ile Asn Glu Tyr Tyr Ile Ala
            340                 345                 350

Asp Ala Ser Glu Asp Gln Val Phe Val Cys Val Ser His Ser Asn Asn
        355                 360                 365

Arg Thr Asn Leu Tyr Ile Ser Glu Ala Glu Gly Leu Lys Phe Ser Leu
    370                 375                 380

Ser Leu Glu Asn Val Leu Tyr Tyr Ser Pro Gly Gly Ala Gly Ser Asp
385                 390                 395                 400

Thr Leu Val Arg Tyr Phe Ala Asn Glu Pro Phe Ala Asp Phe His Arg
                405                 410                 415

Val Glu Gly Leu Gln Gly Val Tyr Ile Ala Thr Leu Ile Asn Gly Ser
            420                 425                 430

Met Asn Glu Glu Asn Met Arg Ser Val Ile Thr Phe Asp Lys Gly Gly
        435                 440                 445

Thr Trp Glu Phe Leu Gln Ala Pro Ala Phe Thr Gly Tyr Gly Glu Lys
    450                 455                 460

Ile Asn Cys Glu Leu Ser Gln Gly Cys Ser Leu His Leu Ala Gln Arg
465                 470                 475                 480

Leu Ser Gln Leu Leu Asn Leu Gln Leu Arg Arg Met Pro Ile Leu Ser
                485                 490                 495

Lys Glu Ser Ala Pro Gly Leu Ile Ile Ala Thr Gly Ser Val Gly Lys
            500                 505                 510

Asn Leu Ala Ser Lys Thr Asn Val Tyr Ile Ser Ser Ser Ala Gly Ala
        515                 520                 525

Arg Trp Arg Glu Ala Leu Pro Gly Pro His Tyr Tyr Thr Trp Gly Asp
    530                 535                 540

His Gly Gly Ile Ile Thr Ala Ile Ala Gln Gly Met Glu Thr Asn Glu
545                 550                 555                 560

Leu Lys Tyr Ser Thr Asn Glu Gly Glu Thr Trp Lys Thr Phe Ile Phe
                565                 570                 575

Ser Glu Lys Pro Val Phe Val Tyr Gly Leu Leu Thr Glu Pro Gly Glu
            580                 585                 590

Lys Ser Thr Val Phe Thr Ile Phe Gly Ser Asn Lys Glu Asn Val His
        595                 600                 605

Ser Trp Leu Ile Leu Gln Val Asn Ala Thr Asp Ala Leu Gly Val Pro
    610                 615                 620

Cys Thr Glu Asn Asp Tyr Lys Leu Trp Ser Pro Ser Asp Glu Arg Gly
625                 630                 635                 640

Asn Glu Cys Leu Leu Gly His Lys Thr Val Phe Lys Arg Arg Thr Pro
                645                 650                 655

His Ala Thr Cys Phe Asn Gly Glu Asp Phe Asp Arg Pro Val Val Val
            660                 665                 670

Ser Asn Cys Ser Cys Thr Arg Glu Asp Tyr Glu Cys Asp Phe Gly Phe
        675                 680                 685

Lys Met Ser Glu Asp Leu Ser Leu Glu Val Cys Val Pro Asp Pro Glu
    690                 695                 700

Phe Ser Gly Lys Ser Tyr Ser Pro Pro Val Pro Cys Pro Val Gly Ser
705                 710                 715                 720

Thr Tyr Arg Arg Thr Arg Gly Tyr Arg Lys Ile Ser Gly Asp Thr Cys
                725                 730                 735

Ser Gly Gly Asp Val Glu Ala Arg Leu Glu Gly Glu Leu Val Pro Cys
            740                 745                 750

Pro Leu Ala Glu Glu Asn Glu Phe Ile Leu Tyr Ala Val Arg Lys Ser
        755                 760                 765

```
Ile Tyr Arg Tyr Asp Leu Ala Ser Gly Ala Thr Glu Gln Leu Pro Leu
    770                 775                 780

Thr Gly Leu Arg Ala Ala Val Ala Leu Asp Phe Asp Tyr Glu His Asn
785                 790                 795                 800

Cys Leu Tyr Trp Ser Asp Leu Ala Leu Asp Val Ile Gln Arg Leu Cys
                805                 810                 815

Leu Asn Gly Ser Thr Gly Gln Glu Val Ile Ile Asn Ser Gly Leu Glu
                820                 825                 830

Thr Val Glu Ala Leu Ala Phe Glu Pro Leu Ser Gln Leu Leu Tyr Trp
            835                 840                 845

Val Asp Ala Gly Phe Lys Lys Ile Glu Val Ala Asn Pro Asp Gly Asp
    850                 855                 860

Phe Arg Leu Thr Ile Val Asn Ser Ser Val Leu Asp Arg Pro Arg Ala
865                 870                 875                 880

Leu Val Leu Val Pro Gln Glu Gly Val Met Phe Trp Thr Asp Trp Gly
                885                 890                 895

Asp Leu Lys Pro Gly Ile Tyr Arg Ser Asn Met Asp Gly Ser Ala Ala
                900                 905                 910

Tyr His Leu Val Ser Glu Asp Val Lys Trp Pro Asn Gly Ile Ser Val
            915                 920                 925

Asp Asp Gln Trp Ile Tyr Trp Thr Asp Ala Tyr Leu Glu Cys Ile Glu
    930                 935                 940

Arg Ile Thr Phe Ser Gly Gln Gln Arg Ser Val Ile Leu Asp Asn Leu
945                 950                 955                 960

Pro His Pro Tyr Ala Ile Ala Val Phe Lys Asn Glu Ile Tyr Trp Asp
                965                 970                 975

Asp Trp Ser Gln Leu Ser Ile Phe Arg Ala Ser Lys Tyr Ser Gly Ser
                980                 985                 990

Gln Met Glu Ile Leu Ala Asn Gln Leu Thr Gly Leu Met Asp Met Lys
            995                 1000                1005

Ile Phe Tyr Lys Gly Lys Asn  Thr Gly Ser Asn Ala  Cys Val Pro
    1010                1015                1020

Arg Pro Cys Ser Leu Leu Cys  Leu Pro Lys Ala Asn  Asn Ser Arg
    1025                1030                1035

Ser Cys Arg Cys Pro Glu Asp  Val Ser Ser Val  Leu Pro Ser
    1040                1045                1050

Gly Asp Leu Met Cys Asp Cys  Pro Gln Gly Tyr Gln  Leu Lys Asn
    1055                1060                1065

Asn Thr Cys Val Lys Glu Glu  Asn Thr Cys Leu Arg  Asn Gln Tyr
    1070                1075                1080

Arg Cys Ser Asn Gly Asn Cys  Ile Asn Ser Ile Trp  Trp Cys Asp
    1085                1090                1095

Phe Asp Asn Asp Cys Gly Asp  Met Ser Asp Glu Arg  Asn Cys Pro
    1100                1105                1110

Thr Thr Ile Cys Asp Leu Asp  Thr Gln Phe Arg Cys  Gln Glu Ser
    1115                1120                1125

Gly Thr Cys Ile Pro Leu Ser  Tyr Lys Cys Asp Leu  Glu Asp Asp
    1130                1135                1140

Cys Gly Asp Asn Ser Asp Glu  Ser His Cys Glu Met  His Gln Cys
    1145                1150                1155

Arg Ser Asp Glu Tyr Asn Cys  Ser Ser Gly Met Cys  Ile Arg Ser
    1160                1165                1170
```

-continued

```
Ser Trp Val Cys Asp Gly Asp Asn Asp Cys Arg Asp Trp Ser Asp
1175                1180                1185

Glu Ala Asn Cys Thr Ala Ile Tyr His Thr Cys Glu Ala Ser Asn
1190                1195                1200

Phe Gln Cys Arg Asn Gly His Cys Ile Pro Gln Arg Trp Ala Cys
1205                1210                1215

Asp Gly Asp Thr Asp Cys Gln Asp Gly Ser Asp Glu Asp Pro Val
1220                1225                1230

Asn Cys Glu Lys Lys Cys Asn Gly Phe Arg Cys Pro Asn Gly Thr
1235                1240                1245

Cys Ile Pro Ser Ser Lys His Cys Asp Gly Leu Arg Asp Cys Ser
1250                1255                1260

Asp Gly Ser Asp Glu Gln His Cys Glu Pro Leu Cys Thr His Phe
1265                1270                1275

Met Asp Phe Val Cys Lys Asn Arg Gln Gln Cys Leu Phe His Ser
1280                1285                1290

Met Val Cys Asp Gly Ile Ile Gln Cys Arg Asp Gly Ser Asp Glu
1295                1300                1305

Asp Ala Ala Phe Ala Gly Cys Ser Gln Asp Pro Glu Phe His Lys
1310                1315                1320

Val Cys Asp Glu Phe Gly Phe Gln Cys Gln Asn Gly Val Cys Ile
1325                1330                1335

Ser Leu Ile Trp Lys Cys Asp Gly Met Asp Asp Cys Gly Asp Tyr
1340                1345                1350

Ser Asp Glu Ala Asn Cys Glu Asn Pro Thr Glu Ala Pro Asn Cys
1355                1360                1365

Ser Arg Tyr Phe Gln Phe Arg Cys Glu Asn Gly His Cys Ile Pro
1370                1375                1380

Asn Arg Trp Lys Cys Asp Arg Glu Asn Asp Cys Gly Asp Trp Ser
1385                1390                1395

Asp Glu Lys Asp Cys Gly Asp Ser His Ile Leu Pro Phe Ser Thr
1400                1405                1410

Pro Gly Pro Ser Thr Cys Leu Pro Asn Tyr Tyr Arg Cys Ser Ser
1415                1420                1425

Gly Thr Cys Val Met Asp Thr Trp Val Cys Asp Gly Tyr Arg Asp
1430                1435                1440

Cys Ala Asp Gly Ser Asp Glu Glu Ala Cys Pro Leu Leu Ala Asn
1445                1450                1455

Val Thr Ala Ala Ser Thr Pro Thr Gln Leu Gly Arg Cys Asp Arg
1460                1465                1470

Phe Glu Phe Glu Cys His Gln Pro Lys Thr Cys Ile Pro Asn Trp
1475                1480                1485

Lys Arg Cys Asp Gly His Gln Asp Cys Gln Asp Gly Arg Asp Glu
1490                1495                1500

Ala Asn Cys Pro Thr His Ser Thr Leu Thr Cys Met Ser Arg Glu
1505                1510                1515

Phe Gln Cys Glu Asp Gly Glu Ala Cys Ile Val Leu Ser Glu Arg
1520                1525                1530

Cys Asp Gly Phe Leu Asp Cys Ser Asp Glu Ser Asp Glu Lys Ala
1535                1540                1545

Cys Ser Asp Glu Leu Thr Val Tyr Lys Val Gln Asn Leu Gln Trp
1550                1555                1560

Thr Ala Asp Phe Ser Gly Asp Val Thr Leu Thr Trp Met Arg Pro
1565                1570                1575
```

```
Lys Lys Met Pro Ser Ala Ser Cys Val Tyr Asn Val Tyr Tyr Arg
    1580            1585                1590

Val Val Gly Glu Ser Ile Trp Lys Thr Leu Glu Thr His Ser Asn
    1595            1600                1605

Lys Thr Asn Thr Val Leu Lys Val Leu Lys Pro Asp Thr Thr Tyr
    1610            1615                1620

Gln Val Lys Val Gln Val Gln Cys Leu Ser Lys Ala His Asn Thr
    1625            1630                1635

Asn Asp Phe Val Thr Leu Arg Thr Pro Glu Gly Leu Pro Asp Ala
    1640            1645                1650

Pro Arg Asn Leu Gln Leu Ser Leu Pro Arg Glu Ala Glu Gly Val
    1655            1660                1665

Ile Val Gly His Trp Ala Pro Pro Ile His Thr His Gly Leu Ile
    1670            1675                1680

Arg Glu Tyr Ile Val Glu Tyr Ser Arg Ser Gly Ser Lys Met Trp
    1685            1690                1695

Ala Ser Gln Arg Ala Ala Ser Asn Phe Thr Glu Ile Lys Asn Leu
    1700            1705                1710

Leu Val Asn Thr Leu Tyr Thr Val Arg Val Ala Ala Val Thr Ser
    1715            1720                1725

Arg Gly Ile Gly Asn Trp Ser Asp Ser Lys Ser Ile Thr Thr Ile
    1730            1735                1740

Lys Gly Lys Val Ile Pro Pro Asp Ile His Ile Asp Ser Tyr
    1745            1750                1755

Gly Glu Asn Tyr Leu Ser Phe Thr Leu Thr Met Glu Ser Asp Ile
    1760            1765                1770

Lys Val Asn Gly Tyr Val Val Asn Leu Phe Trp Ala Phe Asp Thr
    1775            1780                1785

His Lys Gln Glu Arg Arg Thr Leu Asn Phe Arg Gly Ser Ile Leu
    1790            1795                1800

Ser His Lys Val Gly Asn Leu Thr Ala His Thr Ser Tyr Glu Ile
    1805            1810                1815

Ser Ala Trp Ala Lys Thr Asp Leu Gly Asp Ser Pro Leu Ala Phe
    1820            1825                1830

Glu His Val Met Thr Arg Gly Val Arg Pro Pro Ala Pro Ser Leu
    1835            1840                1845

Lys Ala Lys Ala Ile Asn Gln Thr Ala Val Glu Cys Thr Trp Thr
    1850            1855                1860

Gly Pro Arg Asn Val Val Tyr Gly Ile Phe Tyr Ala Thr Ser Phe
    1865            1870                1875

Leu Asp Leu Tyr Arg Asn Pro Lys Ser Leu Thr Thr Ser Leu His
    1880            1885                1890

Asn Lys Thr Val Ile Val Ser Lys Asp Glu Gln Tyr Leu Phe Leu
    1895            1900                1905

Val Arg Val Val Val Pro Tyr Gln Gly Pro Ser Ser Asp Tyr Val
    1910            1915                1920

Val Val Lys Met Ile Pro Asp Ser Arg Leu Pro Pro Arg His Leu
    1925            1930                1935

His Val Val His Thr Gly Lys Thr Ser Val Val Ile Lys Trp Glu
    1940            1945                1950

Ser Pro Tyr Asp Ser Pro Asp Gln Asp Leu Leu Tyr Ala Ile Ala
    1955            1960                1965
```

-continued

Val Lys Asp Leu Ile Arg Lys Thr Asp Arg Ser Tyr Lys Val Lys
    1970                1975                1980

Ser Arg Asn Ser Thr Val Glu Tyr Thr Leu Asn Lys Leu Glu Pro
    1985                1990                1995

Gly Gly Lys Tyr His Ile Ile Val Gln Leu Gly Asn Met Ser Lys
    2000                2005                2010

Asp Ser Ser Ile Lys Ile Thr Thr Val Ser Leu Ser Ala Pro Asp
    2015                2020                2025

Ala Leu Lys Ile Ile Thr Glu Asn Asp His Val Leu Leu Phe Trp
    2030                2035                2040

Lys Ser Leu Ala Leu Lys Glu Lys His Phe Asn Glu Ser Arg Gly
    2045                2050                2055

Tyr Glu Ile His Met Phe Asp Ser Ala Met Asn Ile Thr Ala Tyr
    2060                2065                2070

Leu Gly Asn Thr Thr Asp Asn Phe Phe Lys Ile Ser Asn Leu Lys
    2075                2080                2085

Met Gly His Asn Tyr Thr Phe Thr Val Gln Ala Arg Cys Leu Phe
    2090                2095                2100

Gly Asn Gln Ile Cys Gly Glu Pro Ala Ile Leu Leu Tyr Asp Glu
    2105                2110                2115

Leu Gly Ser Gly Ala Asp Ala Ser Ala Thr Gln Ala Ala Arg Ser
    2120                2125                2130

Thr Asp Val Ala Ala Val Val Val Pro Ile Leu Phe Leu Ile Leu
    2135                2140                2145

Leu Ser Leu Gly Val Gly Phe Ala Ile Leu Tyr Thr Lys His Arg
    2150                2155                2160

Arg Leu Gln Ser Ser Phe Thr Ala Phe Ala Asn Ser His Tyr Ser
    2165                2170                2175

Ser Arg Leu Gly Ser Ala Ile Phe Ser Ser Gly Asp Asp Leu Gly
    2180                2185                2190

Glu Asp Asp Glu Asp Ala Pro Met Ile Thr Gly Phe Ser Asp Asp
    2195                2200                2205

Val Pro Met Val Ile Ala
    2210

<210> SEQ ID NO 3
<211> LENGTH: 1168
<212> TYPE: PRT
<213> ORGANISM: Homo sapiens

<400> SEQUENCE: 3

Met Gly Lys Val Gly Ala Gly Gly Ser Gln Ala Arg Leu Ser Ala
1               5                   10                  15

Leu Leu Ala Gly Ala Gly Leu Leu Ile Leu Cys Ala Pro Gly Val Cys
                20                  25                  30

Gly Gly Gly Ser Cys Cys Pro Ser Pro His Pro Ser Ser Ala Pro Arg
            35                  40                  45

Ser Ala Ser Thr Pro Arg Gly Phe Ser His Gln Gly Arg Pro Gly Arg
    50                  55                  60

Ala Pro Ala Thr Pro Leu Pro Leu Val Val Arg Pro Leu Phe Ser Val
65                  70                  75                  80

Ala Pro Gly Asp Arg Ala Leu Ser Leu Glu Arg Ala Arg Gly Thr Gly
                85                  90                  95

Ala Ser Met Ala Val Ala Ala Arg Ser Gly Arg Arg Arg Ser Gly
            100                 105                 110

-continued

```
Ala Asp Gln Glu Lys Ala Glu Arg Gly Glu Gly Ala Ser Arg Ser Pro
        115                 120                 125
Arg Gly Val Leu Arg Asp Gly Gln Gln Glu Pro Gly Thr Arg Glu
130                 135                 140
Arg Asp Pro Asp Lys Ala Thr Arg Phe Arg Met Glu Glu Leu Arg Leu
145                 150                 155                 160
Thr Ser Thr Thr Phe Ala Leu Thr Gly Asp Ser Ala His Asn Gln Ala
                165                 170                 175
Met Val His Trp Ser Gly His Asn Ser Ser Val Ile Leu Ile Leu Thr
            180                 185                 190
Lys Leu Tyr Asp Tyr Asn Leu Gly Ser Ile Thr Glu Ser Ser Leu Trp
        195                 200                 205
Arg Ser Thr Asp Tyr Gly Thr Thr Tyr Glu Lys Leu Asn Asp Lys Val
210                 215                 220
Gly Leu Lys Thr Ile Leu Ser Tyr Leu Tyr Val Cys Pro Thr Asn Lys
225                 230                 235                 240
Arg Lys Ile Met Leu Leu Thr Asp Pro Glu Ile Glu Ser Ser Leu Leu
                245                 250                 255
Ile Ser Ser Asp Glu Gly Ala Thr Tyr Gln Lys Tyr Arg Leu Asn Phe
            260                 265                 270
Tyr Ile Gln Ser Leu Leu Phe His Pro Lys Gln Glu Asp Trp Ile Leu
        275                 280                 285
Ala Tyr Ser Gln Asp Gln Lys Leu Tyr Ser Ser Ala Glu Phe Gly Arg
    290                 295                 300
Arg Trp Gln Leu Ile Gln Glu Gly Val Val Pro Asn Arg Phe Tyr Trp
305                 310                 315                 320
Ser Val Met Gly Ser Asn Lys Glu Pro Asp Leu Val His Leu Glu Ala
                325                 330                 335
Arg Thr Val Asp Gly His Ser His Tyr Leu Thr Cys Arg Met Gln Asn
            340                 345                 350
Cys Thr Glu Ala Asn Arg Asn Gln Pro Phe Pro Gly Tyr Ile Asp Pro
        355                 360                 365
Asp Ser Leu Ile Val Gln Asp His Tyr Val Phe Val Gln Leu Thr Ser
    370                 375                 380
Gly Gly Arg Pro His Tyr Tyr Val Ser Tyr Arg Arg Asn Ala Phe Ala
385                 390                 395                 400
Gln Met Lys Leu Pro Lys Tyr Ala Leu Pro Lys Asp Met His Val Ile
                405                 410                 415
Ser Thr Asp Glu Asn Gln Val Phe Ala Ala Val Gln Glu Trp Asn Gln
            420                 425                 430
Asn Asp Thr Tyr Asn Leu Tyr Ile Ser Asp Thr Arg Gly Val Tyr Phe
        435                 440                 445
Thr Leu Ala Leu Glu Asn Val Gln Ser Ser Arg Gly Pro Glu Gly Asn
    450                 455                 460
Ile Met Ile Asp Leu Tyr Glu Val Ala Gly Ile Lys Gly Met Phe Leu
465                 470                 475                 480
Ala Asn Lys Lys Ile Asp Asn Gln Val Lys Thr Phe Ile Thr Tyr Asn
                485                 490                 495
Lys Gly Arg Asp Trp Arg Leu Leu Gln Ala Pro Asp Thr Asp Leu Arg
            500                 505                 510
Gly Asp Pro Val His Cys Leu Leu Pro Tyr Cys Ser Leu His Leu His
        515                 520                 525
Leu Lys Val Ser Glu Asn Pro Tyr Thr Ser Gly Ile Ile Ala Ser Lys
    530                 535                 540
```

```
Asp Thr Ala Pro Ser Ile Ile Val Ala Ser Gly Asn Ile Gly Ser Glu
545                 550                 555                 560

Leu Ser Asp Thr Asp Ile Ser Met Phe Val Ser Ser Asp Ala Gly Asn
                565                 570                 575

Thr Trp Arg Gln Ile Phe Glu Glu His Ser Val Leu Tyr Leu Asp
            580                 585                 590

Gln Gly Gly Val Leu Val Ala Met Lys His Thr Ser Leu Pro Ile Arg
        595                 600                 605

His Leu Trp Leu Ser Phe Asp Glu Gly Arg Ser Trp Ser Lys Tyr Ser
    610                 615                 620

Phe Thr Ser Ile Pro Leu Phe Val Asp Gly Val Leu Gly Glu Pro Gly
625                 630                 635                 640

Glu Glu Thr Leu Ile Met Thr Val Phe Gly His Phe Ser His Arg Ser
                645                 650                 655

Glu Trp Gln Leu Val Lys Val Asp Tyr Lys Ser Ile Phe Asp Arg Arg
            660                 665                 670

Cys Ala Glu Glu Asp Tyr Arg Pro Trp Gln Leu His Ser Gln Gly Glu
        675                 680                 685

Ala Cys Ile Met Gly Ala Lys Arg Ile Tyr Lys Lys Arg Lys Ser Glu
690                 695                 700

Arg Lys Cys Met Gln Gly Lys Tyr Ala Gly Ala Met Glu Ser Glu Pro
705                 710                 715                 720

Cys Val Cys Thr Glu Ala Asp Phe Asp Cys Asp Tyr Gly Tyr Glu Arg
                725                 730                 735

His Ser Asn Gly Gln Cys Leu Pro Ala Phe Trp Phe Asn Pro Ser Ser
            740                 745                 750

Leu Ser Lys Asp Cys Ser Leu Gly Gln Ser Tyr Leu Asn Ser Thr Gly
        755                 760                 765

Tyr Arg Lys Val Val Ser Asn Asn Cys Thr Asp Gly Val Arg Glu Gln
770                 775                 780

Tyr Thr Ala Lys Pro Gln Lys Cys Pro Gly Lys Ala Pro Arg Gly Leu
785                 790                 795                 800

Arg Ile Val Thr Ala Asp Gly Lys Leu Thr Ala Glu Gln Gly His Asn
                805                 810                 815

Val Thr Leu Met Val Gln Leu Glu Glu Gly Asp Val Leu Arg Thr Leu
            820                 825                 830

Ile Gln Val Asp Phe Gly Asp Gly Ile Ala Val Ser Tyr Val Asn Leu
        835                 840                 845

Ser Ser Met Glu Asp Gly Ile Lys His Val Tyr Gln Asn Val Gly Ile
850                 855                 860

Phe Arg Val Thr Val Gln Val Asp Asn Ser Leu Gly Ser Asp Ser Ala
865                 870                 875                 880

Val Leu Tyr Leu His Val Thr Cys Pro Leu Glu His Val His Leu Ser
                885                 890                 895

Leu Pro Phe Val Thr Thr Lys Asn Lys Glu Val Asn Ala Thr Ala Val
            900                 905                 910

Leu Trp Pro Ser Gln Val Gly Thr Leu Thr Tyr Val Trp Trp Tyr Gly
        915                 920                 925

Asn Asn Thr Glu Pro Leu Ile Thr Leu Glu Gly Ser Ile Ser Phe Arg
930                 935                 940

Phe Thr Ser Glu Gly Met Asn Thr Ile Thr Val Gln Val Ser Ala Gly
945                 950                 955                 960
```

-continued

Asn Ala Ile Leu Gln Asp Thr Lys Thr Ile Ala Val Tyr Glu Glu Phe
        965                 970                 975

Arg Ser Leu Arg Leu Ser Phe Ser Pro Asn Leu Asp Asp Tyr Asn Pro
        980                 985                 990

Asp Ile Pro Glu Trp Arg Arg Asp Ile Gly Arg Val Ile Lys Lys Ser
        995                 1000                1005

Leu Val Glu Ala Thr Gly Val Pro Gly Gln His Ile Leu Val Ala
    1010                1015                1020

Val Leu Pro Gly Leu Pro Thr Thr Ala Glu Leu Phe Val Leu Pro
    1025                1030                1035

Tyr Gln Asp Pro Ala Gly Glu Asn Lys Arg Ser Thr Asp Asp Leu
    1040                1045                1050

Glu Gln Ile Ser Glu Leu Leu Ile His Thr Leu Asn Gln Asn Ser
    1055                1060                1065

Val His Phe Glu Leu Lys Pro Gly Val Arg Val Leu Val His Ala
    1070                1075                1080

Ala His Leu Thr Ala Ala Pro Leu Val Asp Leu Thr Pro Thr His
    1085                1090                1095

Ser Gly Ser Ala Met Leu Met Leu Leu Ser Val Val Phe Val Gly
    1100                1105                1110

Leu Ala Val Phe Val Ile Tyr Lys Phe Lys Arg Arg Val Ala Leu
    1115                1120                1125

Pro Ser Pro Pro Ser Pro Ser Thr Gln Pro Gly Asp Ser Ser Leu
    1130                1135                1140

Arg Leu Gln Arg Ala Arg His Ala Thr Pro Pro Ser Thr Pro Lys
    1145                1150                1155

Arg Gly Ser Ala Gly Ala Gln Tyr Ala Ile
    1160                1165

<210> SEQ ID NO 4
<211> LENGTH: 1159
<212> TYPE: PRT
<213> ORGANISM: Homo sapiens

<400> SEQUENCE: 4

Met Ala His Arg Gly Pro Ser Arg Ala Ser Lys Gly Pro Gly Pro Thr
1                 5                   10                  15

Ala Arg Ala Pro Ser Pro Gly Ala Pro Pro Pro Arg Ser Pro Arg
            20                  25                  30

Ser Arg Pro Leu Leu Leu Leu Leu Leu Leu Gly Ala Cys Gly Ala
            35                  40                  45

Ala Gly Arg Ser Pro Glu Pro Gly Arg Leu Gly Pro His Ala Gln Leu
        50                  55                  60

Thr Arg Val Pro Arg Ser Pro Ala Gly Arg Ala Glu Pro Gly Gly
65                  70                  75                  80

Gly Glu Asp Arg Gln Ala Arg Gly Thr Glu Pro Gly Ala Pro Gly Pro
            85                  90                  95

Ser Pro Gly Pro Ala Pro Gly Pro Gly Glu Asp Gly Ala Pro Ala Ala
            100                 105                 110

Gly Tyr Arg Arg Trp Glu Arg Ala Ala Pro Leu Ala Gly Val Ala Ser
            115                 120                 125

Arg Ala Gln Val Ser Leu Ile Ser Thr Ser Phe Val Leu Lys Gly Asp
        130                 135                 140

Ala Thr His Asn Gln Ala Met Val His Trp Thr Gly Glu Asn Ser Ser
145                 150                 155                 160

-continued

Val Ile Leu Ile Leu Thr Lys Tyr Tyr His Ala Asp Met Gly Lys Val
            165                 170                 175

Leu Glu Ser Ser Leu Trp Arg Ser Ser Asp Phe Gly Thr Ser Tyr Thr
        180                 185                 190

Lys Leu Thr Leu Gln Pro Gly Val Thr Val Ile Asp Asn Phe Tyr
    195                 200                 205

Ile Cys Pro Thr Asn Lys Arg Lys Val Ile Leu Val Ser Ser Ser Leu
    210                 215                 220

Ser Asp Arg Asp Gln Ser Leu Phe Leu Ser Ala Asp Glu Gly Ala Thr
225                 230                 235                 240

Phe Gln Lys Gln Pro Ile Pro Phe Phe Val Glu Thr Leu Ile Phe His
                245                 250                 255

Pro Lys Glu Glu Asp Lys Val Leu Ala Tyr Thr Lys Glu Ser Lys Leu
            260                 265                 270

Tyr Val Ser Ser Asp Leu Gly Lys Lys Trp Thr Leu Leu Gln Glu Arg
        275                 280                 285

Val Thr Lys Asp His Val Phe Trp Ser Val Ser Gly Val Asp Ala Asp
    290                 295                 300

Pro Asp Leu Val His Val Glu Ala Gln Asp Leu Gly Gly Asp Phe Arg
305                 310                 315                 320

Tyr Val Thr Cys Ala Ile His Asn Cys Ser Glu Lys Met Leu Thr Ala
                325                 330                 335

Pro Phe Ala Gly Pro Ile Asp His Gly Ser Leu Thr Val Gln Asp Asp
            340                 345                 350

Tyr Ile Phe Phe Lys Ala Thr Ser Ala Asn Gln Thr Lys Tyr Tyr Val
        355                 360                 365

Ser Tyr Arg Arg Asn Glu Phe Val Leu Met Lys Leu Pro Lys Tyr Ala
    370                 375                 380

Leu Pro Lys Asp Leu Gln Ile Ile Ser Thr Asp Glu Ser Gln Val Phe
385                 390                 395                 400

Val Ala Val Gln Glu Trp Tyr Gln Met Asp Thr Tyr Asn Leu Tyr Gln
                405                 410                 415

Ser Asp Pro Arg Gly Val Arg Tyr Ala Leu Val Leu Gln Asp Val Arg
            420                 425                 430

Ser Ser Arg Gln Ala Glu Glu Ser Val Leu Ile Asp Ile Leu Glu Val
        435                 440                 445

Arg Gly Val Lys Gly Val Phe Leu Ala Asn Gln Lys Ile Asp Gly Lys
    450                 455                 460

Val Met Thr Leu Ile Thr Tyr Asn Lys Gly Arg Asp Trp Asp Tyr Leu
465                 470                 475                 480

Arg Pro Pro Ser Met Asp Met Asn Gly Lys Pro Thr Asn Cys Lys Pro
                485                 490                 495

Pro Asp Cys His Leu His Leu His Leu Arg Trp Ala Asp Asn Pro Tyr
            500                 505                 510

Val Ser Gly Thr Val His Thr Lys Asp Thr Ala Pro Gly Leu Ile Met
        515                 520                 525

Gly Ala Gly Asn Leu Gly Ser Gln Leu Val Glu Tyr Lys Glu Glu Met
    530                 535                 540

Tyr Ile Thr Ser Asp Cys Gly His Thr Trp Arg Gln Val Phe Glu Glu
545                 550                 555                 560

Glu His His Ile Leu Tyr Leu Asp His Gly Gly Val Ile Val Ala Ile
                565                 570                 575

Lys Asp Thr Ser Ile Pro Leu Lys Ile Leu Lys Phe Ser Val Asp Glu
            580                 585                 590

```
Gly Leu Thr Trp Ser Thr His Asn Phe Thr Ser Thr Ser Val Phe Val
            595                 600                 605

Asp Gly Leu Leu Ser Glu Pro Gly Asp Glu Thr Leu Val Met Thr Val
        610                 615                 620

Phe Gly His Ile Ser Phe Arg Ser Asp Trp Glu Leu Val Lys Val Asp
625                 630                 635                 640

Phe Arg Pro Ser Phe Ser Arg Gln Cys Gly Glu Glu Asp Tyr Ser Ser
                645                 650                 655

Trp Glu Leu Ser Asn Leu Gln Gly Asp Arg Cys Ile Met Gly Gln Gln
            660                 665                 670

Arg Ser Phe Arg Lys Arg Lys Ser Thr Ser Trp Cys Ile Lys Gly Arg
        675                 680                 685

Ser Phe Thr Ser Ala Leu Thr Ser Arg Val Cys Glu Cys Arg Asp Ser
    690                 695                 700

Asp Phe Leu Cys Asp Tyr Gly Phe Glu Arg Ser Pro Ser Ser Glu Ser
705                 710                 715                 720

Ser Thr Asn Lys Cys Ser Ala Asn Phe Trp Phe Asn Pro Leu Ser Pro
                725                 730                 735

Pro Asp Asp Cys Ala Leu Gly Gln Thr Tyr Thr Ser Ser Leu Gly Tyr
            740                 745                 750

Arg Lys Val Val Ser Asn Val Cys Glu Gly Val Asp Met Gln Gln
        755                 760                 765

Ser Gln Val Gln Leu Gln Cys Pro Leu Thr Pro Pro Arg Gly Leu Gln
    770                 775                 780

Val Ser Ile Gln Gly Glu Ala Val Ala Val Arg Pro Gly Glu Asp Val
785                 790                 795                 800

Leu Phe Val Val Arg Gln Glu Gln Gly Asp Val Leu Thr Thr Lys Tyr
                805                 810                 815

Gln Val Asp Leu Gly Asp Gly Phe Lys Ala Met Tyr Val Asn Leu Thr
            820                 825                 830

Leu Thr Gly Glu Pro Ile Arg His Arg Tyr Glu Ser Pro Gly Ile Tyr
        835                 840                 845

Arg Val Ser Val Arg Ala Glu Asn Thr Ala Gly His Asp Glu Ala Val
    850                 855                 860

Leu Phe Val Gln Val Asn Ser Pro Leu Gln Ala Leu Tyr Leu Glu Val
865                 870                 875                 880

Val Pro Val Ile Gly Leu Asn Gln Glu Val Asn Leu Thr Ala Val Leu
                885                 890                 895

Leu Pro Leu Asn Pro Asn Leu Thr Val Phe Tyr Trp Trp Ile Gly His
            900                 905                 910

Ser Leu Gln Pro Leu Leu Ser Leu Asp Asn Ser Val Thr Thr Arg Phe
        915                 920                 925

Ser Asp Thr Gly Asp Val Arg Val Thr Val Gln Ala Ala Cys Gly Asn
    930                 935                 940

Ser Val Leu Gln Asp Ser Arg Val Leu Arg Val Leu Asp Gln Phe Gln
945                 950                 955                 960

Val Met Pro Leu Gln Phe Ser Lys Glu Leu Asp Ala Tyr Asn Pro Asn
                965                 970                 975

Thr Pro Glu Trp Arg Glu Asp Val Gly Leu Val Val Thr Arg Leu Leu
            980                 985                 990

Ser Lys Glu Thr Ser Val Pro Gln  Glu Leu Leu Val Thr  Val Val Lys
        995                 1000                1005
```

Pro Gly Leu Pro Thr Leu Ala Asp Leu Tyr Val Leu Leu Pro Pro
    1010                1015                1020

Pro Arg Pro Thr Arg Lys Arg Ser Leu Ser Ser Asp Lys Arg Leu
    1025                1030                1035

Ala Ala Ile Gln Gln Val Leu Asn Ala Gln Lys Ile Ser Phe Leu
    1040                1045                1050

Leu Arg Gly Gly Val Arg Val Leu Val Ala Leu Arg Asp Thr Gly
    1055                1060                1065

Thr Gly Ala Glu Gln Leu Gly Gly Gly Gly Tyr Trp Ala Val
    1070                1075                1080

Val Val Leu Phe Val Ile Gly Leu Phe Ala Ala Gly Ala Phe Ile
    1085                1090                1095

Leu Tyr Lys Phe Lys Arg Lys Arg Pro Gly Arg Thr Val Tyr Ala
    1100                1105                1110

Gln Met His Asn Glu Lys Glu Gln Glu Met Thr Ser Pro Val Ser
    1115                1120                1125

His Ser Glu Asp Val Gln Gly Ala Val Gln Gly Asn His Ser Gly
    1130                1135                1140

Val Val Leu Ser Ile Asn Ser Arg Glu Met His Ser Tyr Leu Val
    1145                1150                1155

Ser

<210> SEQ ID NO 5
<211> LENGTH: 1222
<212> TYPE: PRT
<213> ORGANISM: Homo sapiens

<400> SEQUENCE: 5

Met Glu Ala Ala Arg Thr Glu Arg Pro Ala Gly Arg Pro Gly Ala Pro
1               5                   10                  15

Leu Val Arg Thr Gly Leu Leu Leu Leu Ser Thr Trp Val Leu Ala Gly
                20                  25                  30

Ala Glu Ile Thr Trp Asp Ala Thr Gly Gly Pro Gly Arg Pro Ala Ala
            35                  40                  45

Pro Ala Ser Arg Pro Pro Ala Leu Ser Pro Leu Ser Pro Arg Ala Val
        50                  55                  60

Ala Ser Gln Trp Pro Glu Glu Leu Ala Ser Ala Arg Arg Ala Ala Val
65                  70                  75                  80

Leu Gly Arg Arg Ala Gly Pro Glu Leu Leu Pro Gln Gln Gly Gly Gly
                85                  90                  95

Arg Gly Gly Glu Met Gln Val Glu Ala Gly Gly Thr Ser Pro Ala Gly
            100                 105                 110

Glu Arg Arg Gly Arg Gly Ile Pro Ala Pro Ala Lys Leu Gly Gly Ala
        115                 120                 125

Arg Arg Ser Arg Arg Ala Gln Pro Pro Ile Thr Gln Glu Arg Gly Asp
130                 135                 140

Ala Trp Ala Thr Ala Pro Ala Asp Gly Ser Arg Gly Ser Arg Pro Leu
145                 150                 155                 160

Ala Lys Gly Ser Arg Glu Glu Val Lys Ala Pro Arg Ala Gly Gly Ser
                165                 170                 175

Ala Ala Glu Asp Leu Arg Leu Pro Ser Thr Ser Phe Ala Leu Thr Gly
            180                 185                 190

Asp Ser Ala His Asn Gln Ala Met Val His Trp Ser Gly His Asn Ser
        195                 200                 205

-continued

Ser Val Ile Leu Ile Leu Thr Lys Leu Tyr Asp Phe Asn Leu Gly Ser
    210                 215                 220

Val Thr Glu Ser Ser Leu Trp Arg Ser Thr Asp Tyr Gly Thr Thr Tyr
225                 230                 235                 240

Glu Lys Leu Asn Asp Lys Val Gly Leu Lys Thr Val Leu Ser Tyr Leu
                245                 250                 255

Tyr Val Asn Pro Thr Asn Lys Arg Lys Ile Met Leu Leu Ser Asp Pro
            260                 265                 270

Glu Met Glu Ser Ser Ile Leu Ile Ser Ser Asp Glu Gly Ala Thr Tyr
        275                 280                 285

Gln Lys Tyr Arg Leu Thr Phe Tyr Ile Gln Ser Leu Leu Phe His Pro
    290                 295                 300

Lys Gln Glu Asp Trp Val Leu Ala Tyr Ser Leu Asp Gln Lys Leu Tyr
305                 310                 315                 320

Ser Ser Met Asp Phe Gly Arg Arg Trp Gln Leu Met His Glu Arg Ile
                325                 330                 335

Thr Pro Asn Arg Phe Tyr Trp Ser Val Ala Gly Leu Asp Lys Glu Ala
            340                 345                 350

Asp Leu Val His Met Glu Val Arg Thr Thr Asp Gly Tyr Ala His Tyr
        355                 360                 365

Leu Thr Cys Arg Ile Gln Glu Cys Ala Glu Thr Thr Arg Ser Gly Pro
370                 375                 380

Phe Ala Arg Ser Ile Asp Ile Ser Ser Leu Val Val Gln Asp Glu Tyr
385                 390                 395                 400

Ile Phe Ile Gln Val Thr Thr Ser Gly Arg Ala Ser Tyr Tyr Val Ser
                405                 410                 415

Tyr Arg Arg Glu Ala Phe Ala Gln Ile Lys Leu Pro Lys Tyr Ser Leu
            420                 425                 430

Pro Lys Asp Met His Ile Ile Ser Thr Asp Glu Asn Gln Val Phe Ala
        435                 440                 445

Ala Val Gln Glu Trp Asn Gln Asn Asp Thr Tyr Asn Leu Tyr Ile Ser
    450                 455                 460

Asp Thr Arg Gly Ile Tyr Phe Thr Leu Ala Met Glu Asn Ile Lys Ser
465                 470                 475                 480

Ser Arg Gly Leu Met Gly Asn Ile Ile Glu Leu Tyr Glu Val Ala
                485                 490                 495

Gly Ile Lys Gly Ile Phe Leu Ala Asn Lys Lys Val Asp Asp Gln Val
            500                 505                 510

Lys Thr Tyr Ile Thr Tyr Asn Lys Gly Arg Asp Trp Arg Leu Leu Gln
        515                 520                 525

Ala Pro Asp Val Asp Leu Arg Gly Ser Pro Val His Cys Leu Leu Pro
    530                 535                 540

Phe Cys Ser Leu His Leu His Leu Gln Leu Ser Glu Asn Pro Tyr Ser
545                 550                 555                 560

Ser Gly Arg Ile Ser Ser Lys Glu Thr Ala Pro Gly Leu Val Val Ala
                565                 570                 575

Thr Gly Asn Ile Gly Pro Glu Leu Ser Tyr Thr Asp Ile Gly Val Phe
            580                 585                 590

Ile Ser Ser Asp Gly Gly Asn Thr Trp Arg Gln Ile Phe Asp Glu Glu
        595                 600                 605

Tyr Asn Val Trp Phe Leu Asp Trp Gly Gly Ala Leu Val Ala Met Lys
    610                 615                 620

His Thr Pro Leu Pro Val Arg His Leu Trp Val Ser Phe Asp Glu Gly
625                 630                 635                 640

```
His Ser Trp Asp Lys Tyr Gly Phe Thr Ser Val Pro Leu Phe Val Asp
                645                 650                 655
Gly Ala Leu Val Glu Ala Gly Met Glu Thr His Ile Met Thr Val Phe
            660                 665                 670
Gly His Phe Ser Leu Arg Ser Glu Trp Gln Leu Val Lys Val Asp Tyr
        675                 680                 685
Lys Ser Ile Phe Ser Arg His Cys Thr Lys Glu Asp Tyr Gln Thr Trp
    690                 695                 700
His Leu Leu Asn Gln Gly Glu Pro Cys Val Met Gly Glu Arg Lys Ile
705                 710                 715                 720
Phe Lys Lys Arg Lys Pro Gly Ala Gln Cys Ala Leu Gly Arg Asp His
                725                 730                 735
Ser Gly Ser Val Val Ser Glu Pro Cys Val Cys Ala Asn Trp Asp Phe
            740                 745                 750
Glu Cys Asp Tyr Gly Tyr Glu Arg His Gly Glu Ser Gln Cys Val Pro
        755                 760                 765
Ala Phe Trp Tyr Asn Pro Ala Ser Pro Ser Lys Asp Cys Ser Leu Gly
    770                 775                 780
Gln Ser Tyr Leu Asn Ser Thr Gly Tyr Arg Arg Ile Val Ser Asn Asn
785                 790                 795                 800
Cys Thr Asp Gly Leu Arg Glu Lys Tyr Thr Ala Lys Ala Gln Met Cys
                805                 810                 815
Pro Gly Lys Ala Pro Arg Gly Leu His Val Val Thr Thr Asp Gly Arg
            820                 825                 830
Leu Val Ala Glu Gln Gly His Asn Ala Thr Phe Ile Ile Leu Met Glu
        835                 840                 845
Glu Gly Asp Leu Gln Arg Thr Asn Ile Gln Leu Asp Phe Gly Asp Gly
    850                 855                 860
Ile Ala Val Ser Tyr Ala Asn Phe Ser Pro Ile Glu Asp Gly Ile Lys
865                 870                 875                 880
His Val Tyr Lys Ser Ala Gly Ile Phe Gln Val Thr Ala Tyr Ala Glu
                885                 890                 895
Asn Asn Leu Gly Ser Asp Thr Ala Val Leu Phe Leu His Val Val Cys
            900                 905                 910
Pro Val Glu His Val His Leu Arg Val Pro Phe Val Ala Ile Arg Asn
        915                 920                 925
Lys Glu Val Asn Ile Ser Ala Val Val Trp Pro Ser Gln Leu Gly Thr
    930                 935                 940
Leu Thr Tyr Phe Trp Trp Phe Gly Asn Ser Thr Lys Pro Leu Ile Thr
945                 950                 955                 960
Leu Asp Ser Ser Ile Ser Phe Thr Phe Leu Ala Glu Gly Thr Asp Thr
                965                 970                 975
Ile Thr Val Gln Val Ala Ala Gly Asn Ala Leu Ile Gln Asp Thr Lys
            980                 985                 990
Glu Ile Ala Val His Glu Tyr Phe Gln Ser Gln Leu Leu Ser Phe Ser
        995                 1000                1005
Pro Asn Leu Asp Tyr His Asn Pro Asp Ile Pro Glu Trp Arg Lys
    1010                1015                1020
Asp Ile Gly Asn Val Ile Lys Arg Ala Leu Val Lys Val Thr Ser
    1025                1030                1035
Val Pro Glu Asp Gln Ile Leu Ile Ala Val Phe Pro Gly Leu Pro
    1040                1045                1050
```

```
Thr Ser Ala Glu Leu Phe Ile Leu Pro Pro Lys Asn Leu Thr Glu
1055                1060                1065

Arg Arg Lys Gly Asn Glu Gly Asp Leu Glu Gln Ile Val Glu Thr
1070                1075                1080

Leu Phe Asn Ala Leu Asn Gln Asn Leu Val Gln Phe Glu Leu Lys
1085                1090                1095

Pro Gly Val Gln Val Ile Val Tyr Val Thr Gln Leu Thr Leu Ala
1100                1105                1110

Pro Leu Val Asp Ser Ser Ala Gly His Ser Ser Ser Ala Met Leu
1115                1120                1125

Met Leu Leu Ser Val Val Phe Val Gly Leu Ala Val Phe Leu Ile
1130                1135                1140

Tyr Lys Phe Lys Arg Lys Ile Pro Trp Ile Asn Ile Tyr Ala Gln
1145                1150                1155

Val Gln His Asp Lys Glu Gln Glu Met Ile Gly Ser Val Ser Gln
1160                1165                1170

Ser Glu Asn Ala Pro Lys Ile Thr Leu Ser Asp Phe Thr Glu Pro
1175                1180                1185

Glu Glu Leu Leu Asp Lys Glu Leu Asp Thr Arg Val Ile Gly Gly
1190                1195                1200

Ile Ala Thr Ile Ala Asn Ser Glu Ser Thr Lys Glu Ile Pro Asn
1205                1210                1215

Cys Thr Ser Val
1220

<210> SEQ ID NO 6
<211> LENGTH: 247
<212> TYPE: PRT
<213> ORGANISM: Homo sapiens

<400> SEQUENCE: 6

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
        50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
                100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
        130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
                180                 185                 190
```

```
Lys Glu Gly Cys Arg Gly Ile Asp Lys Arg His Trp Asn Ser Gln Cys
            195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245

<210> SEQ ID NO 7
<211> LENGTH: 796
<212> TYPE: PRT
<213> ORGANISM: Homo sapiens

<400> SEQUENCE: 7

Met Leu Arg Gly Gly Arg Arg Gly Gln Leu Gly Trp His Ser Trp Ala
1               5                   10                  15

Ala Gly Pro Gly Ser Leu Leu Ala Trp Leu Ile Leu Ala Ser Ala Gly
            20                  25                  30

Ala Ala Pro Cys Pro Asp Ala Cys Cys Pro His Gly Ser Ser Gly Leu
        35                  40                  45

Arg Cys Thr Arg Asp Gly Ala Leu Asp Ser Leu His His Leu Pro Gly
    50                  55                  60

Ala Glu Asn Leu Thr Glu Leu Tyr Ile Glu Asn Gln Gln His Leu Gln
65                  70                  75                  80

His Leu Glu Leu Arg Asp Leu Arg Gly Leu Gly Glu Leu Arg Asn Leu
                85                  90                  95

Thr Ile Val Lys Ser Gly Leu Arg Phe Val Ala Pro Asp Ala Phe His
            100                 105                 110

Phe Thr Pro Arg Leu Ser Arg Leu Asn Leu Ser Phe Asn Ala Leu Glu
        115                 120                 125

Ser Leu Ser Trp Lys Thr Val Gln Gly Leu Ser Leu Gln Glu Leu Val
    130                 135                 140

Leu Ser Gly Asn Pro Leu His Cys Ser Cys Ala Leu Arg Trp Leu Gln
145                 150                 155                 160

Arg Trp Glu Glu Glu Gly Leu Gly Gly Val Pro Glu Gln Lys Leu Gln
                165                 170                 175

Cys His Gly Gln Gly Pro Leu Ala His Met Pro Asn Ala Ser Cys Gly
            180                 185                 190

Val Pro Thr Leu Lys Val Gln Val Pro Asn Ala Ser Val Asp Val Gly
        195                 200                 205

Asp Asp Val Leu Leu Arg Cys Gln Val Glu Gly Arg Gly Leu Glu Gln
    210                 215                 220

Ala Gly Trp Ile Leu Thr Glu Leu Glu Gln Ser Ala Thr Val Met Lys
225                 230                 235                 240

Ser Gly Gly Leu Pro Ser Leu Gly Leu Thr Leu Ala Asn Val Thr Ser
                245                 250                 255

Asp Leu Asn Arg Lys Asn Val Thr Cys Trp Ala Glu Asn Asp Val Gly
            260                 265                 270

Arg Ala Glu Val Ser Val Gln Val Asn Val Ser Phe Pro Ala Ser Val
        275                 280                 285

Gln Leu His Thr Ala Val Glu Met His His Trp Cys Ile Pro Phe Ser
    290                 295                 300

Val Asp Gly Gln Pro Ala Pro Ser Leu Arg Trp Leu Phe Asn Gly Ser
305                 310                 315                 320
```

```
Val Leu Asn Glu Thr Ser Phe Ile Phe Thr Glu Phe Leu Glu Pro Ala
            325                 330                 335

Ala Asn Glu Thr Val Arg His Gly Cys Leu Arg Leu Asn Gln Pro Thr
            340                 345                 350

His Val Asn Asn Gly Asn Tyr Thr Leu Leu Ala Ala Asn Pro Phe Gly
            355                 360                 365

Gln Ala Ser Ala Ser Ile Met Ala Ala Phe Met Asp Asn Pro Phe Glu
            370                 375                 380

Phe Asn Pro Glu Asp Pro Ile Pro Val Ser Phe Ser Pro Val Asp Thr
385                 390                 395                 400

Asn Ser Thr Ser Gly Asp Pro Val Glu Lys Lys Asp Glu Thr Pro Phe
            405                 410                 415

Gly Val Ser Val Ala Val Gly Leu Ala Val Phe Ala Cys Leu Phe Leu
            420                 425                 430

Ser Thr Leu Leu Leu Val Leu Asn Lys Cys Gly Arg Arg Asn Lys Phe
            435                 440                 445

Gly Ile Asn Arg Pro Ala Val Leu Ala Pro Glu Asp Gly Leu Ala Met
            450                 455                 460

Ser Leu His Phe Met Thr Leu Gly Gly Ser Ser Leu Ser Pro Thr Glu
465                 470                 475                 480

Gly Lys Gly Ser Gly Leu Gln Gly His Ile Ile Glu Asn Pro Gln Tyr
            485                 490                 495

Phe Ser Asp Ala Cys Val His His Ile Lys Arg Arg Asp Ile Val Leu
            500                 505                 510

Lys Trp Glu Leu Gly Glu Gly Ala Phe Gly Lys Val Phe Leu Ala Glu
            515                 520                 525

Cys His Asn Leu Leu Pro Glu Gln Asp Lys Met Leu Val Ala Val Lys
            530                 535                 540

Ala Leu Lys Glu Ala Ser Glu Ser Ala Arg Gln Asp Phe Gln Arg Glu
545                 550                 555                 560

Ala Glu Leu Leu Thr Met Leu Gln His Gln His Ile Val Arg Phe Phe
            565                 570                 575

Gly Val Cys Thr Glu Gly Arg Pro Leu Leu Met Val Phe Glu Tyr Met
            580                 585                 590

Arg His Gly Asp Leu Asn Arg Phe Leu Arg Ser His Gly Pro Asp Ala
            595                 600                 605

Lys Leu Leu Ala Gly Gly Glu Asp Val Ala Pro Gly Pro Leu Gly Leu
            610                 615                 620

Gly Gln Leu Leu Ala Val Ala Ser Gln Val Ala Ala Gly Met Val Tyr
625                 630                 635                 640

Leu Ala Gly Leu His Phe Val His Arg Asp Leu Ala Thr Arg Asn Cys
            645                 650                 655

Leu Val Gly Gln Gly Leu Val Val Lys Ile Gly Asp Phe Gly Met Ser
            660                 665                 670

Arg Asp Ile Tyr Ser Thr Asp Tyr Tyr Arg Val Gly Gly Arg Thr Met
            675                 680                 685

Leu Pro Ile Arg Trp Met Pro Glu Ser Ile Leu Tyr Arg Lys Phe
            690                 695                 700

Thr Thr Glu Ser Asp Val Trp Ser Phe Gly Val Val Leu Trp Glu Ile
705                 710                 715                 720

Phe Thr Tyr Gly Lys Gln Pro Trp Tyr Gln Leu Ser Asn Thr Glu Ala
            725                 730                 735

Ile Asp Cys Ile Thr Gln Gly Arg Glu Leu Glu Arg Pro Arg Ala Cys
            740                 745                 750
```

```
Pro Pro Glu Val Tyr Ala Ile Met Arg Gly Cys Trp Gln Arg Glu Pro
        755                 760                 765

Gln Gln Arg His Ser Ile Lys Asp Val His Ala Arg Leu Gln Ala Leu
        770                 775                 780

Ala Gln Ala Pro Pro Val Tyr Leu Asp Val Leu Gly
785                 790                 795

<210> SEQ ID NO 8
<211> LENGTH: 822
<212> TYPE: PRT
<213> ORGANISM: Homo sapiens

<400> SEQUENCE: 8

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
                20                  25                  30

Pro Thr Ser Cys Lys Cys Ser Ala Ser Arg Ile Trp Cys Ser Asp Pro
            35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335
```

```
Thr Asn His Thr Glu Tyr His Gly Cys Leu Gln Leu Asp Asn Pro Thr
            340                 345                 350
His Met Asn Asn Gly Asp Tyr Thr Leu Ile Ala Lys Asn Glu Tyr Gly
            355                 360                 365
Lys Asp Glu Lys Gln Ile Ser Ala His Phe Met Gly Trp Pro Gly Ile
            370                 375                 380
Asp Asp Gly Ala Asn Pro Asn Tyr Pro Asp Val Ile Tyr Glu Asp Tyr
385                 390                 395                 400
Gly Thr Ala Ala Asn Asp Ile Gly Asp Thr Thr Asn Arg Ser Asn Glu
            405                 410                 415
Ile Pro Ser Thr Asp Val Thr Asp Lys Thr Gly Arg Glu His Leu Ser
            420                 425                 430
Val Tyr Ala Val Val Ile Ala Ser Val Val Gly Phe Cys Leu Leu
            435                 440                 445
Val Met Leu Phe Leu Leu Lys Leu Ala Arg His Ser Lys Phe Gly Met
            450                 455                 460
Lys Gly Pro Ala Ser Val Ile Ser Asn Asp Asp Ser Ala Ser Pro
465                 470                 475                 480
Leu His His Ile Ser Asn Gly Ser Asn Thr Pro Ser Ser Glu Gly
            485                 490                 495
Gly Pro Asp Ala Val Ile Ile Gly Met Thr Lys Ile Pro Val Ile Glu
            500                 505                 510
Asn Pro Gln Tyr Phe Gly Ile Thr Asn Ser Gln Leu Lys Pro Asp Thr
            515                 520                 525
Phe Val Gln His Ile Lys Arg His Asn Ile Val Leu Lys Arg Glu Leu
            530                 535                 540
Gly Glu Gly Ala Phe Gly Lys Val Phe Leu Ala Glu Cys Tyr Asn Leu
545                 550                 555                 560
Cys Pro Glu Gln Asp Lys Ile Leu Val Ala Val Lys Thr Leu Lys Asp
            565                 570                 575
Ala Ser Asp Asn Ala Arg Lys Asp Phe His Arg Glu Ala Glu Leu Leu
            580                 585                 590
Thr Asn Leu Gln His Glu His Ile Val Lys Phe Tyr Gly Val Cys Val
            595                 600                 605
Glu Gly Asp Pro Leu Ile Met Val Phe Glu Tyr Met Lys His Gly Asp
            610                 615                 620
Leu Asn Lys Phe Leu Arg Ala His Gly Pro Asp Ala Val Leu Met Ala
625                 630                 635                 640
Glu Gly Asn Pro Pro Thr Glu Leu Thr Gln Ser Gln Met Leu His Ile
            645                 650                 655
Ala Gln Gln Ile Ala Ala Gly Met Val Tyr Leu Ala Ser Gln His Phe
            660                 665                 670
Val His Arg Asp Leu Ala Thr Arg Asn Cys Leu Val Gly Glu Asn Leu
            675                 680                 685
Leu Val Lys Ile Gly Asp Phe Gly Met Ser Arg Asp Val Tyr Ser Thr
            690                 695                 700
Asp Tyr Tyr Arg Val Gly Gly His Thr Met Leu Pro Ile Arg Trp Met
705                 710                 715                 720
Pro Pro Glu Ser Ile Met Tyr Arg Lys Phe Thr Thr Glu Ser Asp Val
            725                 730                 735
Trp Ser Leu Gly Val Val Leu Trp Glu Ile Phe Thr Tyr Gly Lys Gln
            740                 745                 750
```

```
Pro Trp Tyr Gln Leu Ser Asn Glu Val Ile Glu Cys Ile Thr Gln
        755                 760                 765
Gly Arg Val Leu Gln Arg Pro Arg Thr Cys Pro Gln Glu Val Tyr Glu
770                 775                 780
Leu Met Leu Gly Cys Trp Gln Arg Glu Pro His Met Arg Lys Asn Ile
785                 790                 795                 800
Lys Gly Ile His Thr Leu Leu Gln Asn Leu Ala Lys Ala Ser Pro Val
                805                 810                 815
Tyr Leu Asp Ile Leu Gly
                820

<210> SEQ ID NO 9
<211> LENGTH: 839
<212> TYPE: PRT
<213> ORGANISM: Homo sapiens

<400> SEQUENCE: 9

Met Asp Val Ser Leu Cys Pro Ala Lys Cys Ser Phe Trp Arg Ile Phe
1               5                   10                  15
Leu Leu Gly Ser Val Trp Leu Asp Tyr Val Gly Ser Val Leu Ala Cys
                20                  25                  30
Pro Ala Asn Cys Val Cys Ser Lys Thr Glu Ile Asn Cys Arg Arg Pro
            35                  40                  45
Asp Asp Gly Asn Leu Phe Pro Leu Leu Glu Gly Gln Asp Ser Gly Asn
        50                  55                  60
Ser Asn Gly Asn Ala Ser Ile Asn Ile Thr Asp Ile Ser Arg Asn Ile
65                  70                  75                  80
Thr Ser Ile His Ile Glu Asn Trp Arg Ser Leu His Thr Leu Asn Ala
                85                  90                  95
Val Asp Met Glu Leu Tyr Thr Gly Leu Gln Lys Leu Thr Ile Lys Asn
                100                 105                 110
Ser Gly Leu Arg Ser Ile Gln Pro Arg Ala Phe Ala Lys Asn Pro His
            115                 120                 125
Leu Arg Tyr Ile Asn Leu Ser Ser Asn Arg Leu Thr Thr Leu Ser Trp
        130                 135                 140
Gln Leu Phe Gln Thr Leu Ser Leu Arg Glu Leu Gln Leu Glu Gln Asn
145                 150                 155                 160
Phe Phe Asn Cys Ser Cys Asp Ile Arg Trp Met Gln Leu Trp Gln Glu
                165                 170                 175
Gln Gly Glu Ala Lys Leu Asn Ser Gln Asn Leu Tyr Cys Ile Asn Ala
                180                 185                 190
Asp Gly Ser Gln Leu Pro Leu Phe Arg Met Asn Ile Ser Gln Cys Asp
            195                 200                 205
Leu Pro Glu Ile Ser Val Ser His Val Asn Leu Thr Val Arg Glu Gly
        210                 215                 220
Asp Asn Ala Val Ile Thr Cys Asn Gly Ser Gly Ser Pro Leu Pro Asp
225                 230                 235                 240
Val Asp Trp Ile Val Thr Gly Leu Gln Ser Ile Asn Thr His Gln Thr
                245                 250                 255
Asn Leu Asn Trp Thr Asn Val His Ala Ile Asn Leu Thr Leu Val Asn
                260                 265                 270
Val Thr Ser Glu Asp Asn Gly Phe Thr Leu Thr Cys Ile Ala Glu Asn
            275                 280                 285
Val Val Gly Met Ser Asn Ala Ser Val Ala Leu Thr Val Tyr Tyr Pro
        290                 295                 300
```

```
Pro Arg Val Val Ser Leu Glu Glu Pro Glu Leu Arg Leu Glu His Cys
305                 310                 315                 320

Ile Glu Phe Val Val Arg Gly Asn Pro Pro Thr Leu His Trp Leu
            325                 330                 335

His Asn Gly Gln Pro Leu Arg Glu Ser Lys Ile Ile His Val Glu Tyr
            340                 345                 350

Tyr Gln Glu Gly Glu Ile Ser Glu Gly Cys Leu Leu Phe Asn Lys Pro
            355                 360                 365

Thr His Tyr Asn Asn Gly Asn Tyr Thr Leu Ile Ala Lys Asn Pro Leu
            370                 375                 380

Gly Thr Ala Asn Gln Thr Ile Asn Gly His Phe Leu Lys Glu Pro Phe
385                 390                 395                 400

Pro Glu Ser Thr Asp Asn Phe Ile Leu Phe Asp Glu Val Ser Pro Thr
            405                 410                 415

Pro Pro Ile Thr Val Thr His Lys Pro Glu Glu Asp Thr Phe Gly Val
            420                 425                 430

Ser Ile Ala Val Gly Leu Ala Ala Phe Ala Cys Val Leu Leu Val Val
            435                 440                 445

Leu Phe Val Met Ile Asn Lys Tyr Gly Arg Arg Ser Lys Phe Gly Met
450                 455                 460

Lys Gly Pro Val Ala Val Ile Ser Gly Glu Glu Asp Ser Ala Ser Pro
465                 470                 475                 480

Leu His His Ile Asn His Gly Ile Thr Thr Pro Ser Ser Leu Asp Ala
            485                 490                 495

Gly Pro Asp Thr Val Val Ile Gly Met Thr Arg Ile Pro Val Ile Glu
            500                 505                 510

Asn Pro Gln Tyr Phe Arg Gln Gly His Asn Cys His Lys Pro Asp Thr
            515                 520                 525

Tyr Val Gln His Ile Lys Arg Arg Asp Ile Val Leu Lys Arg Glu Leu
            530                 535                 540

Gly Glu Gly Ala Phe Gly Lys Val Phe Leu Ala Glu Cys Tyr Asn Leu
545                 550                 555                 560

Ser Pro Thr Lys Asp Lys Met Leu Val Ala Val Lys Ala Leu Lys Asp
                565                 570                 575

Pro Thr Leu Ala Ala Arg Lys Asp Phe Gln Arg Glu Ala Glu Leu Leu
            580                 585                 590

Thr Asn Leu Gln His Glu His Ile Val Lys Phe Tyr Gly Val Cys Gly
            595                 600                 605

Asp Gly Asp Pro Leu Ile Met Val Phe Glu Tyr Met Lys His Gly Asp
610                 615                 620

Leu Asn Lys Phe Leu Arg Ala His Gly Pro Asp Ala Met Ile Leu Val
625                 630                 635                 640

Asp Gly Gln Pro Arg Gln Ala Lys Gly Glu Leu Gly Leu Ser Gln Met
            645                 650                 655

Leu His Ile Ala Ser Gln Ile Ala Ser Gly Met Val Tyr Leu Ala Ser
            660                 665                 670

Gln His Phe Val His Arg Asp Leu Ala Thr Arg Asn Cys Leu Val Gly
            675                 680                 685

Ala Asn Leu Leu Val Lys Ile Gly Asp Phe Gly Met Ser Arg Asp Val
            690                 695                 700

Tyr Ser Thr Asp Tyr Tyr Arg Leu Phe Asn Pro Ser Gly Asn Asp Phe
705                 710                 715                 720

Cys Ile Trp Cys Glu Val Gly Gly His Thr Met Leu Pro Ile Arg Trp
            725                 730                 735
```

```
Met Pro Pro Glu Ser Ile Met Tyr Arg Lys Phe Thr Thr Glu Ser Asp
            740                 745                 750

Val Trp Ser Phe Gly Val Ile Leu Trp Glu Ile Phe Thr Tyr Gly Lys
            755                 760                 765

Gln Pro Trp Phe Gln Leu Ser Asn Thr Glu Val Ile Glu Cys Ile Thr
770                 775                 780

Gln Gly Arg Val Leu Glu Arg Pro Arg Val Cys Pro Lys Glu Val Tyr
785                 790                 795                 800

Asp Val Met Leu Gly Cys Trp Gln Arg Glu Pro Gln Gln Arg Leu Asn
            805                 810                 815

Ile Lys Glu Ile Tyr Lys Ile Leu His Ala Leu Gly Lys Ala Thr Pro
            820                 825                 830

Ile Tyr Leu Asp Ile Leu Gly
            835

<210> SEQ ID NO 10
<211> LENGTH: 427
<212> TYPE: PRT
<213> ORGANISM: Homo sapiens

<400> SEQUENCE: 10

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
            35                  40                  45

Leu Gly Glu Gly Val Ala Gln Pro Cys Gly Ala Asn Gln Thr Val Cys
        50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
            115                 120                 125

Glu Ala Gly Ser Gly Leu Val Phe Ser Cys Gln Asp Lys Gln Asn Thr
130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
            195                 200                 205

Ala Pro Ser Thr Gln Glu Pro Glu Ala Pro Pro Glu Gln Asp Leu Ile
        210                 215                 220

Ala Ser Thr Val Ala Gly Val Val Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270
```

-continued

```
Lys Arg Trp Asn Ser Cys Lys Gln Asn Lys Gln Gly Ala Asn Ser Arg
        275                 280                 285

Pro Val Asn Gln Thr Pro Pro Pro Glu Gly Glu Lys Leu His Ser Asp
        290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
            340                 345                 350

Gly Ser Ala Gly Asp Thr Trp Arg His Leu Ala Gly Glu Leu Gly Tyr
        355                 360                 365

Gln Pro Glu His Ile Asp Ser Phe Thr His Glu Ala Cys Pro Val Arg
        370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
            405                 410                 415

Leu Cys Ser Glu Ser Thr Ala Thr Ser Pro Val
                420                 425
```